(12) United States Patent
Konya et al.

(10) Patent No.: US 6,792,979 B2
(45) Date of Patent: Sep. 21, 2004

(54) METHODS FOR CREATING WOVEN DEVICES

(75) Inventors: Andras Konya, Houston, TX (US); Hideki Hyodoh, Nishino Nishiku Sapporo (JP); Kenneth C. Wright, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/244,333

(22) Filed: Sep. 16, 2002

(65) Prior Publication Data

US 2003/0149475 A1 Aug. 7, 2003

Related U.S. Application Data

(62) Division of application No. 09/496,243, filed on Feb. 1, 2000.
(60) Provisional application No. 60/118,211, filed on Feb. 1, 1999, and provisional application No. 60/125,191, filed on Mar. 18, 1999.

(51) Int. Cl.[7] .............................................. B21F 27/02
(52) U.S. Cl. ..................................... 140/92.1; 623/1.15
(58) Field of Search ............................. 623/1.15, 1.22; 140/92.1; 87/9, 34

(56) References Cited

U.S. PATENT DOCUMENTS

| | | | | |
|---|---|---|---|---|
| 1,945,195 A | * | 1/1934 | Kellems | 140/92.1 |
| 2,836,181 A | | 5/1958 | Tapp | 128/334 |
| 2,936,257 A | | 5/1960 | Nailler et al. | 154/2.22 |
| 3,463,197 A | | 8/1969 | Slade | 138/125 |
| 3,620,218 A | | 11/1971 | Schmitt | 128/334 R |

(List continued on next page.)

FOREIGN PATENT DOCUMENTS

| | | |
|---|---|---|
| DE | 19703482 | 8/1998 |
| EP | 0701800 A1 | 3/1996 ............ A61F/2/06 |
| EP | 0782841 A2 | 7/1997 |
| EP | 0804909 | 11/1997 |
| EP | 893108 | 1/1999 |

(List continued on next page.)

OTHER PUBLICATIONS

Didcott, "Oesophageal strictures: treatment by slow continuous dilation," *Ann. Roy. Coll. Surg. Engl.*, 53:112–126, 1973.

(List continued on next page.)

*Primary Examiner*—Lowell A. Larson
(74) *Attorney, Agent, or Firm*—Fulbright & Jaworski L.L.P.

(57) ABSTRACT

Self-expandable, woven intravascular devices for use as stents (both straight and tapered), filters (both temporary and permanent) and occluders for insertion and implantation into a variety of anatomical structures. The devices may be formed from shape memory metals such as nitinol. The devices may also be formed from biodegradable materials. Delivery systems for the devices include two hollow tubes that operate coaxially. A device is secured to the tubes prior to the implantation and delivery of the device by securing one end of the device to the outside of the inner tube and by securing the other end of the device to the outside of the outer tube. The stents may be partially or completely covered by graft materials, but may also be bare. The devices may be formed from a single wire. The devices may be formed by either hand or machine weaving. The devices may be created by bending shape memory wires around tabs projecting from a template, and weaving the ends of the wires to create the body of the device such that the wires cross each other to form a plurality of angles, at least one of the angles being obtuse. The value of the obtuse angle may be increased by axially compressing the body.

22 Claims, 41 Drawing Sheets

U.S. PATENT DOCUMENTS

| | | |
|---|---|---|
| 4,503,569 A | 3/1985 | Dotter .................... 3/1.4 |
| 4,580,568 A | 4/1986 | Gianturco ................ 128/345 |
| 4,619,246 A | 10/1986 | Molgaard-Nielsen et al. .. 128/1 |
| 4,655,771 A | 4/1987 | Wallsten ................ 623/1 |
| 4,733,665 A | 3/1988 | Palmaz ................ 128/343 |
| 4,739,762 A | 4/1988 | Palmaz ................ 128/343 |
| 4,776,337 A | 10/1988 | Palmaz ................ 128/343 |
| 4,850,999 A | 7/1989 | Planck .................. 623/1 |
| 4,893,543 A * | 1/1990 | Phillips ................ 87/34 |
| 4,954,126 A | 9/1990 | Wallsten ................ 600/36 |
| 4,969,458 A | 11/1990 | Wiktor ................ 606/194 |
| 5,026,377 A | 6/1991 | Burton et al. ........... 606/108 |
| 5,061,275 A | 10/1991 | Wallsten et al. ......... 623/1 |
| 5,102,417 A | 4/1992 | Palmaz ................ 606/195 |
| 5,104,404 A | 4/1992 | Wolff .................. 623/1 |
| 5,135,536 A | 8/1992 | Hillstead .............. 606/195 |
| 5,219,355 A | 6/1993 | Parodi et al. ........... 606/191 |
| 4,733,665 A | 1/1994 | Palmaz ................ 606/108 |
| 5,350,398 A | 9/1994 | Pavcnik et al. ......... 606/200 |
| 5,360,443 A | 11/1994 | Barone et al. .......... 623/1 |
| 5,389,106 A | 2/1995 | Tower ................ 606/198 |
| 5,395,390 A | 3/1995 | Simon et al. ........... 606/198 |
| 5,411,549 A | 5/1995 | Peters ................ 623/1 |
| 5,419,231 A | 5/1995 | Earle, III et al. ........ 87/1 |
| D359,802 S | 6/1995 | Fontaine .............. D24/155 |
| 5,425,739 A | 6/1995 | Jessen ................ 606/155 |
| 5,425,984 A | 6/1995 | Kennedy et al. ........ 428/229 |
| 5,443,458 A | 8/1995 | Eury ................ 604/891.1 |
| 5,478,355 A | 12/1995 | Muth et al. ........... 606/230 |
| 5,485,774 A | 1/1996 | Osborne .............. 87/6 |
| 5,507,769 A | 4/1996 | Marin et al. .......... 606/198 |
| 4,954,126 A | 5/1996 | Wallsten ............. 600/36 |
| 5,527,282 A | 6/1996 | Segal ................ 604/104 |
| 5,527,324 A | 6/1996 | Krantz et al. .......... 606/155 |
| 4,655,771 A | 9/1996 | Wallsten ............. 623/1 |
| 5,551,954 A | 9/1996 | Buscemi et al. ........ 623/1 |
| 5,591,195 A | 1/1997 | Taberi et al. .......... 606/194 |
| 5,597,378 A | 1/1997 | Jervis ................ 606/78 |
| 5,632,771 A | 5/1997 | Boatman et al. ........ 623/1 |
| 5,643,339 A | 7/1997 | Kavteladze et al. ..... 623/1 |
| 5,669,936 A | 9/1997 | Lazarus .............. 623/1 |
| 5,670,161 A | 9/1997 | Healy et al. .......... 424/426 |
| 5,674,277 A | 10/1997 | Freitag .............. 623/1 |
| 5,679,400 A | 10/1997 | Tuch ................ 427/2.14 |
| 5,683,411 A | 11/1997 | Kavteladze et al. ..... 606/200 |
| 5,695,469 A | 12/1997 | Segal ................ 604/104 |
| 5,707,376 A | 1/1998 | Kavteladze et al. ..... 606/108 |
| 5,709,701 A | 1/1998 | Parodi ............... 606/194 |
| 5,713,917 A | 2/1998 | Leonhardt et al. ...... 606/194 |
| 5,716,396 A | 2/1998 | Williams, Jr. .......... 623/1 |
| 5,720,735 A | 2/1998 | Dorros ............... 604/284 |
| 5,733,327 A | 3/1998 | Igaki et al. ........... 623/1 |
| 5,755,708 A | 5/1998 | Segal ................ 604/109 |
| 5,766,710 A | 6/1998 | Turnlund et al. ....... 428/36.1 |
| 5,769,882 A | 6/1998 | Fogarty et al. ........ 623/1 |
| 5,772,668 A | 6/1998 | Summers et al. ....... 606/108 |
| 5,800,519 A * | 9/1998 | Sandock ............. 623/1.22 |
| 4,739,762 A | 10/1998 | Palmaz .............. 606/108 |
| 5,824,053 A | 10/1998 | Khosravi et al. ....... 623/1 |
| 5,830,229 A | 11/1998 | Kónya et al. ......... 606/198 |
| 5,851,217 A | 12/1998 | Wolff et al. .......... 623/1 |
| 5,860,998 A | 1/1999 | Robinson et al. ...... 606/194 |
| 5,876,432 A | 3/1999 | Lau et al. ............ 623/1 |
| 5,891,191 A | 4/1999 | Stinson .............. 623/1 |
| 5,902,332 A | 5/1999 | Schatz ............... 623/1 |
| 5,913,896 A | 6/1999 | Boyle et al. .......... 623/1 |
| 5,928,279 A | 7/1999 | Shannon et al. ....... 623/1 |
| 5,944,738 A | 8/1999 | Amplatz et al. ....... 606/213 |
| 5,968,088 A | 10/1999 | Hansen et al. ........ 623/1 |
| 6,007,574 A * | 12/1999 | Pulnev et al. ......... 623/1.15 |
| 6,059,752 A | 5/2000 | Segal ................ 604/107 |
| 6,237,460 B1 * | 5/2001 | Frid ................. 623/1.22 |
| 2001/0003801 A1 | 6/2001 | Strecker ............. 623/1.11 |

FOREIGN PATENT DOCUMENTS

| | | |
|---|---|---|
| GB | 1183497 | 3/1970 |
| GB | 1205743 | 9/1970 |
| GB | 2135585 | 9/1984 |
| WO | WO 91/17789 | 5/1991 |
| WO | WO 96/01591 | 1/1996 |
| WO | WO 97/16133 | 5/1997 |
| WO | WO 98/29043 | 12/1997 |
| WO | WO 98/11847 | 3/1998 |
| WO | WO 98/19630 | 5/1998 |
| WO | WO 99/32051 | 7/1998 |
| WO | WO 98/33454 | 8/1998 |
| WO | WO 98/46168 | 10/1998 |
| WO | WO 00/09059 | 8/1999 |
| WO | WO 00/44308 | 8/2000 |

OTHER PUBLICATIONS

"Wallstent Endoprosthesis" marketing material, Boston Scientific Vascular, 1998.

Reexamination file history for B1–4,954,126.

Reexamination file history for B1–4,655,771.

Dotter, "Transluminally–placed coilspring endarterial tube grafts," *Investigative Radiology*, 4:329–332, 1969.

Seven photographs taken by Hideki Hyodob of stents displayed during a Japanese metallic stentgraft meeting, Feb. 22, 1999.

*JVIR Supplement*, vol. 10, No. 2, Part 2: 284, 287, Feb. 1999.

Photgraph taken by András Kónya of stent at SCVIR meeting in Orlando, Florida, Mar. 20–25, 1999.

Three photographs taken by András Kónya of poster authored by Hideki Hyodoh, András Kónya, and Kenneth C. Wright at SCVIR meeting in Orlando, Florida, Mar. 20–25, 1999.

Fallone et al., "Elastic characteristics of the self–expanding metallic stents," *Invest. Radiol.*, 23:370–376, 1988.

Gillams et al., "Self–expandable stainless steel braided endoprosthesis for biliary strictures," *Radiology*, 174:137–140, 1990.

Günther et al., "Venous stenoses in dialysis shunts: Treatment with self–expanding metallic stents," *Radiology*, 170:401405, 1989.

Milroy et al., "A new stent for the treatment of urethral strictures," *Br. J. Urol.*, 63:392–396, 1989.

Murayama et al., "Nonadhesive liquid embolic agent for cerebral arteriovenous malformations: Preliminary histopathological studies in swine rete mirabile," *Neurosurgery*, 43:1164–1175, 1998.

Nashef et al., "Expanding wire stents in benign tracheobronchial disease: Indications and complications," *Ann. Thorac. Surg.*, 54:937–940, 1992.

Palmaz, "Balloon–expandable intravascular stent," *AJR*, 150:1263–1269, 1988.

Peterson et al., "Gianturco–Rosch Z stents in tracheobronchial stenoses," *JVIR*, 6:925–931, 1995.

Schampaert, "The V–stent: a novel technique for coronary bifurcation stenting," *Cathet. Cardiovasc. Diagn.*, 39(3):320–326, 1996.

Shurman et al., "Neointimal hyperplasia in low–profile nitinol stents, Palmaz stents, and Wallstents: a comparative experimental study," *Cardiovasc. Intervent. Radiol.*, 19:248–254, 1996.

Taki et al., "A new liquid material for embolization of arteriovenous malformations," AJNR, 11:163–168, 1990.

Terada et al., "Embolization of arteriovenous malformations with peripheral aneurysms using ethylene vinyl alcohol copolymer," J. Neurosurg., 75:655–660, 1991.

Wallace et al., "Tracheobronchial tree: Expandable metallic stents used in experimental and clinical applications," Radiology, 158:309–312, 1986.

Ben–Menachem et al., "Hemorrhage associated with pelvic fractures: causes, diagnosis, and emergent management," AJR, 157:1005–1014, 1991.

Bing et al.."Percutaneous ureteral occlusion with use of Gianturco coils and gelatine sponge, Part I. Swine model" JVIR; 3:313–317, 1992 (a).

Bing et al. "Percutaneous ureteral occlusion with use of Gianturco coils and gelatine sponge, Part II. Clinical Experience," JVIR; 3:319–321, 1992 (b).

Cambier et al., "Percutaneous closure of the small (<2.5 mm) patent dutus arteriosus using coil embolization," Am. J. Cardiol., 69:815–816, 1992.

Crochet et al., "Vena Tech–LGM filter: long–term results of a prospective study," Radiology, 188:857–860, 1993.

Dorfman, "Percutaneous inferior vena cava filters," Radiology, 174:987–992, 1990.

Dutton et al., "Pulmonary arteriovenous malformations: results of treatment with coil embolization in 53 patients," AJR, 165:1119–1125, 1995.

Fischell et al., "The β–particle–emitting radiosotope stent (Isostent): animal studies and planned clinical trials," Am. J. Cardiol., 78(Suppl 3A):45–50, 1996.

Fursue et al., "Hepatocellular carcinoma with portal vein tumor thrombus: embolization of arterioportal shunts," Radiology, 204:787–790, 1997.

Gianturco et al., "Mechanical device for arterial occlusion," AJR, 124:428–435, 1975.

Grassi, "Inferior vena caval filters: Analysis of five currently available devices," AJR, 156:813–821, 1991.

Grifka et al., "Transcatheter patent ductus arteriosus closure in an infant using the Gianturco Grifka vascular occlusion device," Am. J. Cardiol., 78:721–723, 1996.

Guglielme et al., "Highflow, small–hole arteriovenous fistulas: treatment with electrodetachable coils," AJNR, 16:325–328, 1995.

Hammer et al., "In vitro evaluation of vena cava filters," JVIR, 5:869–876, 1994.

Hendrickx et al., "Long–term survival after embolization of potentially lethal bleeding malignant pelvic turnouts," Br. J. Radial., 68:1336–1343, 1995.

Hijazi and Geggel, "Results of anterograde transcatheter closure of patent ductus arteriosus using single or multiple Gianturco coils," Am. J. Cardiol., 74:925–929, 1994.

Hijazi and Geggel, "Transcatheter closure of patent ductus arteriosus using coils," Am. J. Cardiol., 79:1279–1280, 1997.

Hosking et al., "Transcatheter occlusion of the persistently patent ductus arteriosus," Circulation, 84:2313–2317, 1991.

Jaeger et al., "In vitro model for evaluation of inferior vena cava filters: effect of experimental parameters on thrombus–capturing efficacy of the Vena Tech–LGM filter," JVIR, 9:295–304, 1998.

Kato et al., "Use of a self–expanding vascular occluder for embolization during endovascular aortic aneurysm repair," JVIR, 8:27–33, 1997.

Katsamouris et al., "Inferior vena cava filters: In vitro comparison of clot trapping and flow dynamics," Radiology, 166:361–366, 1988.

Kónya et al., "Anchoring coil embolization in a high–flow arterial model," JVIR, 9:249–254, 1998.

Kónya and Wright, Preliminary results with a new vascular basket occluder in swine. JVIR, 10:1043–1049, 1999.

Korbin et al., "Comparison of filters in an oversized vena caval phantom: intracaval placement of a Bird's Nest filter versus biiliac placement of Greenfield, Vena–Tech–LGM, and Simon nitinol filters," JVIR, 3:559–564, 1992.

Krichenko et al., "Angiographic classification of the isolated, persistently patent ductus arteriosus and implications for percutaneous catheter occlusion," Am. J. Cardiol., 63:877–880, 1989.

Latson, "Residual shunts after transcatheter closure of patent ductus arteriosus," Circulation, 84:2591–2593, 1991.

Levey et al., "Safety and efficacy of transcatheter embolization of auxiliary and shoulder arterial injuries," JVIR, 2:99–104, 1991.

Lipton et al., "Percutaneous Retrieval of two Wallstent endoprostheses from the heart through a single jugular sheath," JVIR, 6:469–472, 1995.

Lloyd et al., "Transcatheter occlusion of patent ductus arteriosus with Gianturco coils," Circulation, 88:1412–1420, 1993.

Magal et al., "A new device for transcatheter closure of patent ductus arteriosus: a feasibility study in dogs," Invest. Radiol., 24:272–276, 1989.

Marks et al., "A mechanically detachable coil for the treatment of aneurysms and occlusion of blood vessels," AJNR, 15:821–827, 1994.

Masura et al., "Catheter closure of moderate to large sized patent ductus arteriosus using the new Amplatz duct occluder: immediate and short term results," J. Am. Coll. Cardiol., 31:878–882, 1998.

Milward, "Temporary and Retrievable inferior vena cava filters: Current status," JVIR, 9:381–387, 1998.

Nancarrow et al., "Stability of coil emboli: an in vitro study," Cardiovasc. Intervent. Radiol., 10:226–229, 1987.

O'Halpin et al., "Therapeutic arterial embolization: report of five years' experience," Clin. Radiol., 354:85–93, 1984.

Pozza et al., "Transcatheter occlusion of patent ductus arteriosus using a newly developed self–expanding device: evaluation in a canine model," Invest. Radiol., 30:104–109, 1995.

Prahlow et al., "Cardiac perforation due to Wallstent embolization: a fatal complication of the transjugular intrahepatic portosystemic shunt procedure," Radiology, 205:170–172, 1997.

Prince et al., "Local; intravascular effects of the nitinol wire blood clot filter," Invest. Radiol., 23:294–300, 1988.

Punekar et al., "Post–surgical recurrent varicocele: efficacy of internal spermatic venography and steel–coil embolization," Br. J. Urol., 77:12–128, 1996.

Rashkind et al., "Nonsurgical closure of patent ductus arteriosus: clinical application of the Rushkind PDA occluder–system," Circulation, 75:583–592, 1987.

Reidy and Qureshi, "Interlocking detachable platinum coils, a controlled embolization device: early clinical experience," Cardiovasc. Intervent. Radiol., 19:85–90, 1996.

Sagara et al., "Recanalization after coil embolotherapy of pulmonary arteriovenous malformations: study of long term outcome and mechanism for recanalization," *AJR*, 170:727–730, 1998.

Schmitz Rode et al., "Self–expandable spindle for transcatheter vascular occlusion: in vivo experiments," *Radiology*, 188:95–100, 1993.

Schüurmann et al., "Neointimal hyperplasia in low–profile nitinol stents, Palmaz stents, and Wallstents: a comparative experimental study," *Cardiovasc. Intervent. Radiol.* 19:248–254, 1996.

Schild et al., "Effectiveness of platinum wire microcoils for venous occlusion: a study on patients treated for venogenic impotence," *Cardiovasc. Intervent. Radiol.*, 17:170–172, 1994.

Schwartz et al., "Effectiveness of transcatheter embolization in the control of hepatic vascular injuries," *JVIR*, 4:359–365, 1993.

Selby Jr., "Interventional radiology of trauma," *Radiol. Clin. N. Am.*, 30:427–439, 1992.

Sharafuddin et al., "Repositionable vascular occluder: experimental comparison with standard Gianturco coils," *JVIR*, 7:695–703, 1996.

Sharafuddin et al., "Experimental evaluation of a new self expanding patent ductus arteriosus occluder in a canine model," *JVIR*, 7:877–887, 1996.

Simon et al., "Comparative evaluation of clinically available inferior vena cava filters with an in vitro physiologic simulation of the vena cava," *Radiology*, 189:769–774, 1993.

Sommer et al., "Use of preformed nitinol snare to improve transcatheter coil delivery in occlusion of patent ductus arteriosus," *Am. J. Cardiol.*, 74:836–839, 1994.

Teitelbaum et al., "Microcatheter embolization of non–neurologic traumatic vascular lesions," *JVIR*, 4:149–154, 1993.

Tometzki et al., "Transcatheter occlusion of the patent ductus arteriosus with Cook detachable coils," *Heart*, 76:531–535, 1996.

Uzun et al., "Transcatheter occlusion of the arterial duct with Cook detchable coils: early experience," *Heart*, 76:269–273, 1996.

Vedantham et al., "Uterine artery embolization: an underused method for controlling pelvic hemorrhage," *Am. J. Obstet. Gynecol.*, 176:938–948, 1997.

Vesely et al., "Upper extremity central venous obsruction in hemodialysis patients: treatment with Wallstents," *Radiology*, 204:343–348, 1997.

Wallace et al., "Arterial occlusion of pelvic bone tumors," *Cancer*, 43: 322–328, 1979.

Wessel et al., "Outpatient closure of the patent ductus arteriosus," *Circulation*, 77:1068 1071, 1988.

White et al., "Pulmonary arteriovenous malformations: diagnosis and transcatheter embolotherpy," *JVIR*, 7:787–804, 1996.

Xian et al., "Multiple emboli and filter function: An in vitro comparison of three vena cava filters," *JVIR*, 6:887–893, 1995.

Yune, "Inferior vena cava filter: Search for an ideal device," *Radiology*, 172:15–16, 1989.

Zubillaga et al., "Endovascular occlusion of intracranial aneurysms with electrically detachable coils: correlation of aneurysm neck size and treatment results," *AJNR*, 15:815–820, 1994.

Balko et al, "Transfemoral placement of intraluminal polyurethane prosthesis for abdominal aortic aneurysm," *J. Surg. Res.*, 40:305–309, 1986.

"Conformance by Design," World Medical Manufacturing Corporation.

World Medical News, 5(5), Feb. 1997.

Zarins et al., "AneuRx stent graft versus open surgical repair of abdominal aortic aneurysms: multicenter prospective clinical trial," *J. Vasc. Surg.*, 29:292–308, 1999.

Letter from Howard J. Leonhardt to Sidney Wallace, dated Apr. 22, 1997, with two attachments.

Document entitled "Patient: #1115", faxed from Howard J. Leonhardt to Andras Konya on Apr. 11, 1998.

JVIR Supplement, Scientific Program, SCVIR $22^{nd}$ Annual Scientific Meeting, Mar. 8–13, 1997, Sheraton Washington Hotel, 8(1) Part 2, pp. 251–252, Jan.–Feb. 1997.

World Medical News, 5(6), May 1997.

Pictures of poster presented at SCVIR $22^{nd}$ Annual Scientific Meeting, Mar. 8–13, 1997, Sheraton Washington Hotel.

Descriptions on poster presented at SCVIR $22^{nd}$ Annual Scientific Meeting, Mar. 8–13, 1997, Sheraton Washington Hotel.

International Search Report posted Jun. 24, 1999.

* cited by examiner

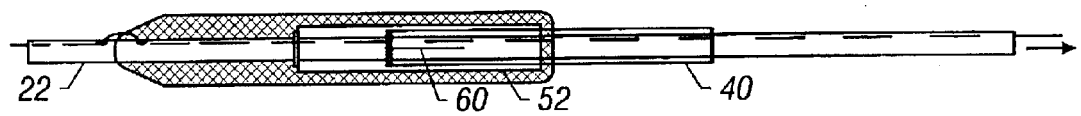
FIG. 5D
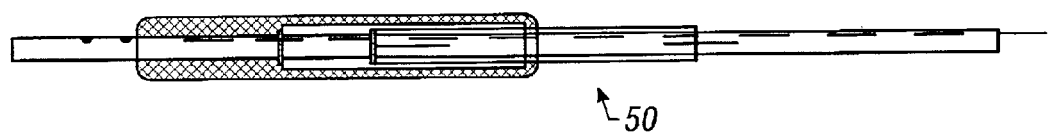
FIG. 5E
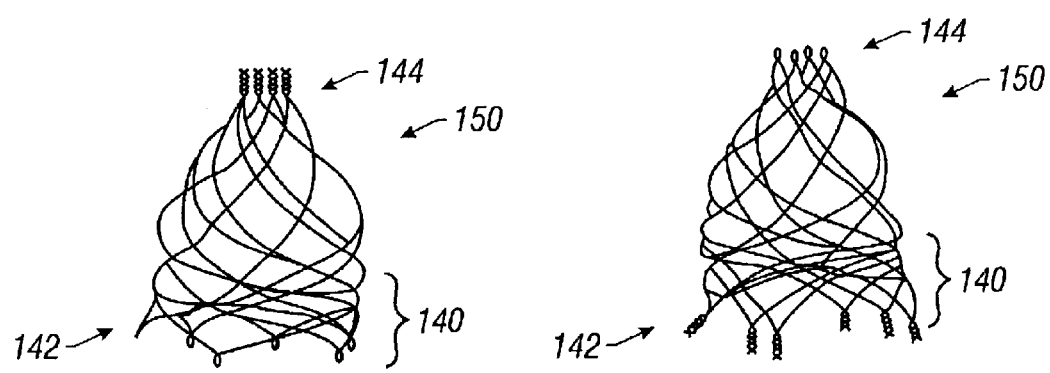
FIG. 6  FIG. 7

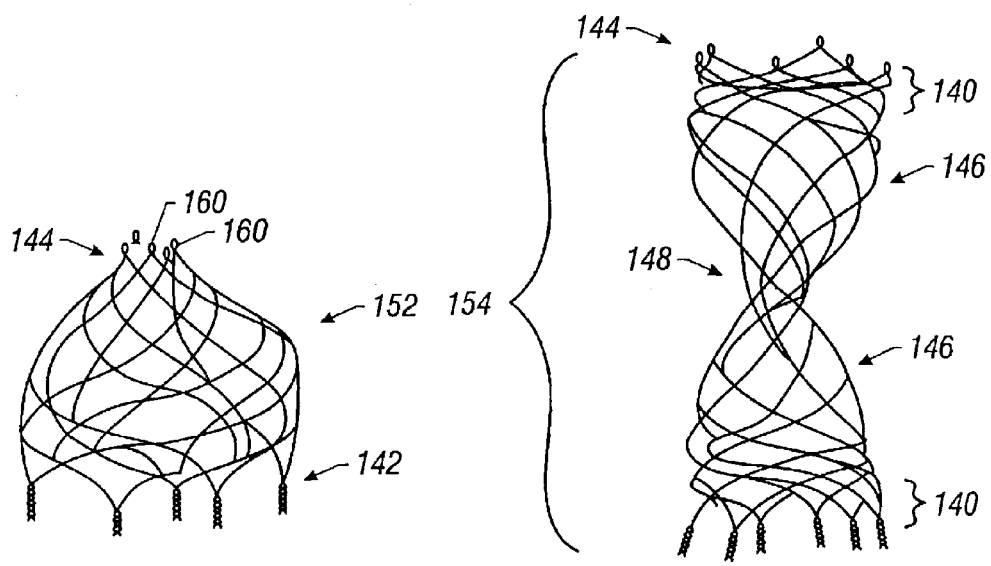
FIG. 8  FIG. 9
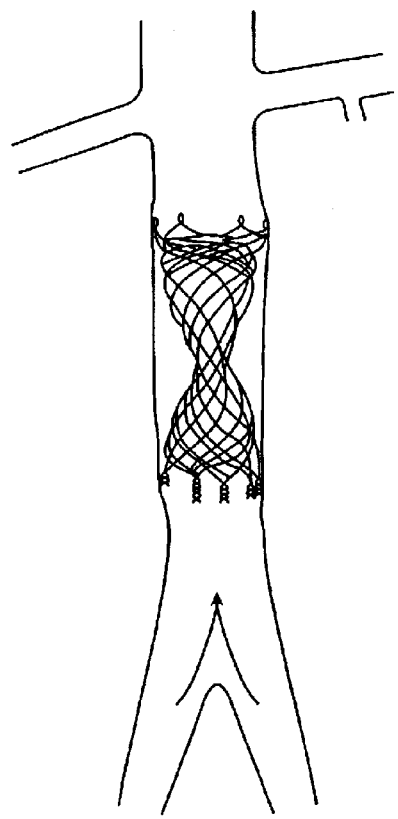
FIG. 10

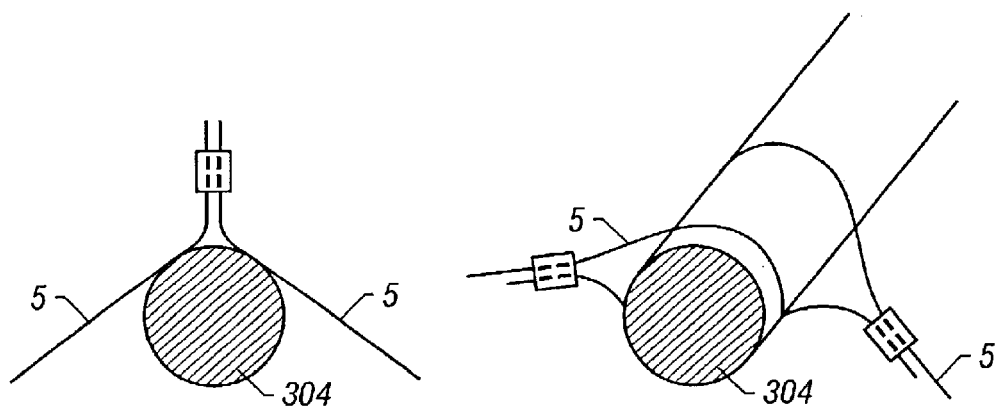
FIG. 30A  FIG. 30B
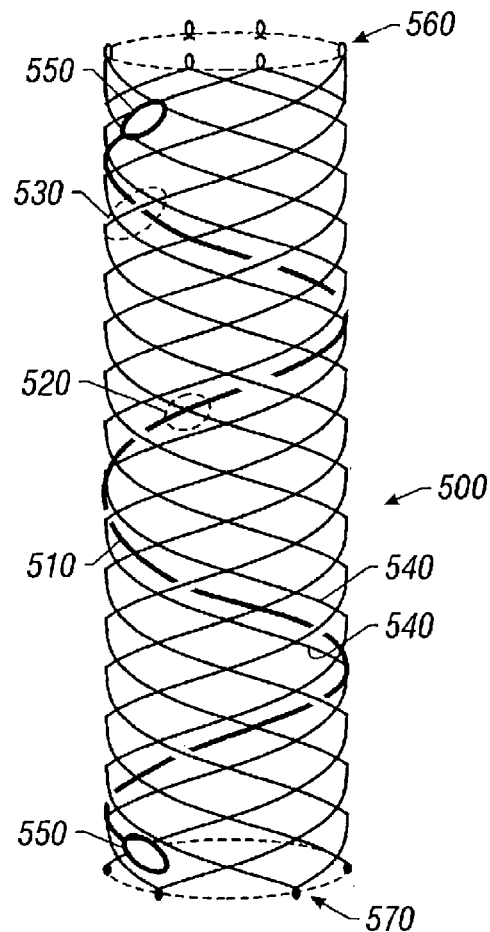
FIG. 31

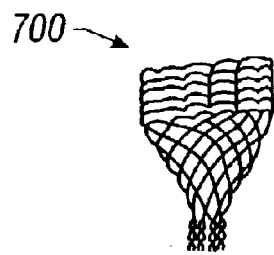
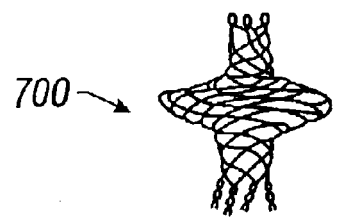
*FIG. 33D*           *FIG. 33E*
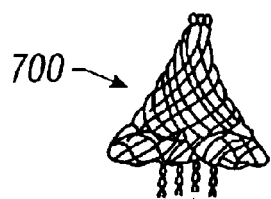
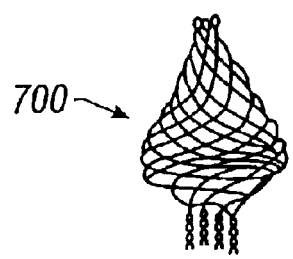
*FIG. 33F*           *FIG. 33G*
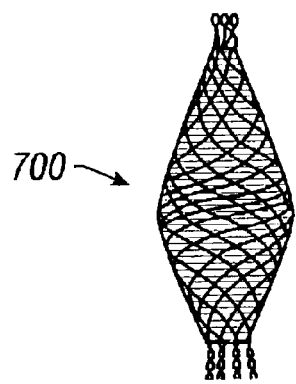
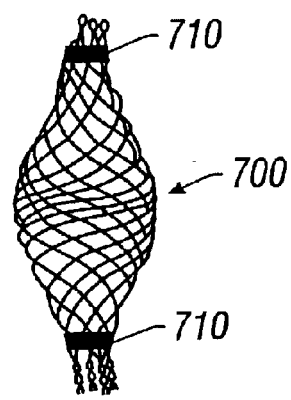
*FIG. 34*           *FIG. 35*

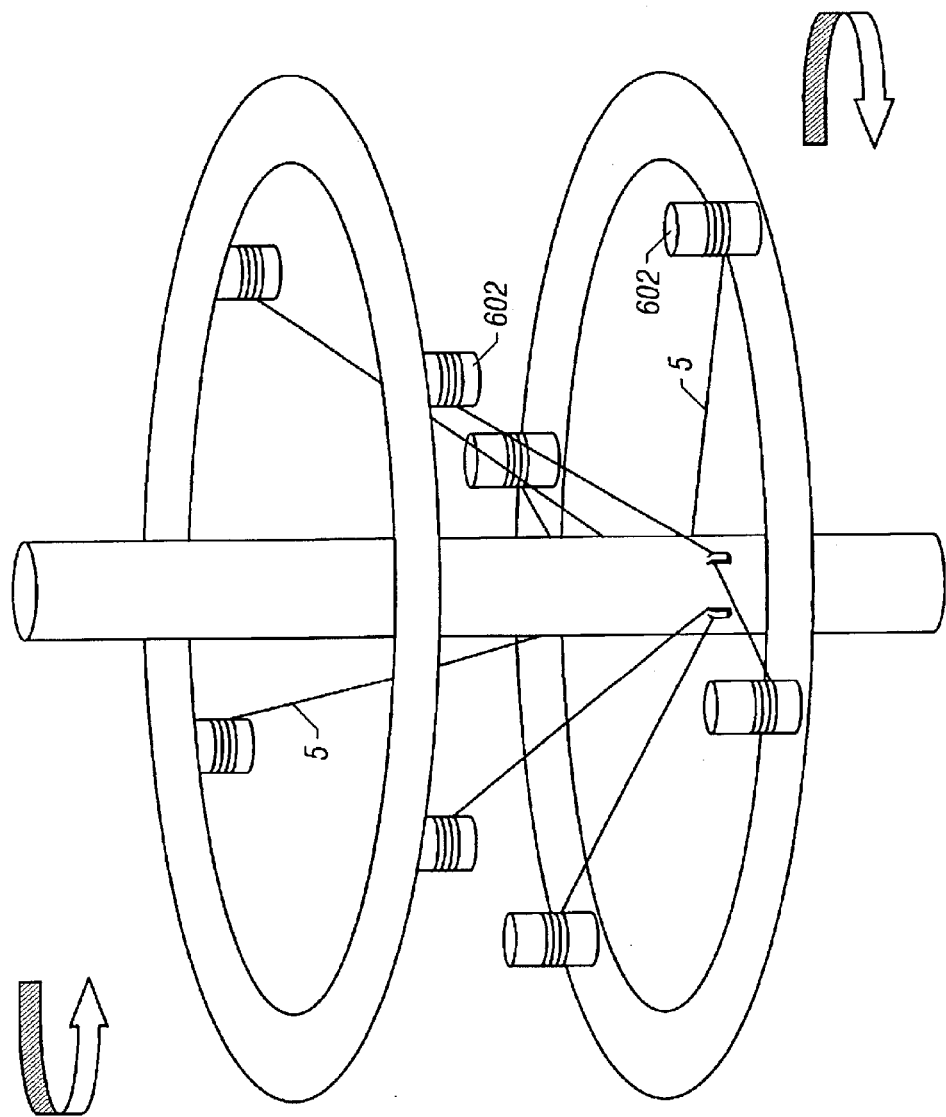

METHODS FOR CREATING WOVEN DEVICES

This is a divisional of co-pending application Ser. No. 09/496,243, filed Feb. 1, 2000, which claims priority to U.S. Provisional Patent Application Serial No. 60/118,211 filed Feb. 1, 1999 and U.S. Provisional Patent Application Serial No. 60/125,191 filed Mar. 18, 1999. The entire texts of these provisional patent applications are specifically incorporated by reference without disclaimer.

BACKGROUND OF THE INVENTION

1. Field of the Invention

The present invention relates generally to intravascular devices. More particularly, it concerns self-expandable woven intravascular devices for use as stents, occluders or filters, the methods of making the same, and the apparatus and methods for delivery of the same into a living creature.

2. Description of Related Art

Intravascular devices that serve as stents or filters constructed using a plain weave, such as the stent disclosed in U.S. Pat. No. 4,655,771 to Wallsten (hereinafter, the WALLSTENT), have a propensity to show a high-degree of elongation axially with diameter reduction. This is especially significant, when the angle of the crossing wires is close to the largest possible. The closer that the angle between the wires is to 180°, the more the corresponding elongation of the stent is at a given percentage of decrease in diameter. Any discrepancy between the diameters of the stent and the vessel can result in a considerable elongation of the stent. Simultaneously, the woven type stent has the largest expansile force and hence the biggest resistance to outer compression when the angle between the crossing wires is close to 180°. In some applications, such as outer compression by a space occupying lesion, the increased radial force may be advantageous. The disadvantage of a propensity for elongation is that great care must be taken when delivering such a stent in a vessel or non-vascular tubular structure in order to properly position it.

A further disadvantage of intravascular devices formed using a plain weave, is that they are often incapable of maintaining their shape when bent. For example, when such a stent is being delivered through a tortuous passageway with many turns, upon being bent, the weave of the stent tightens (e.g., the angle of the crossing wires approaches 180°). As a result of this tightening, the diameter of the stent increases and the length of the stent decreases. Consequently, the diameter of the stent may exceed the diameter of the vessel or structure through which it is traveling, impeding the delivery of the stent or causing the stent to lodge in the vessel. This problem may be due in part to the use of weave materials such as stainless steel, which exhibit poor shape memory. This problem may also be due to the free, unclosed wires used to form the stent. The free sharp ends can create potential complications by penetrating, or perforating the wall of the tubular structure where such a stent is placed. Further, steps that have been taken to eliminate the free, sharp ends, such as connection with U-shaped members using welding, glue or the like (Wallsten, 1987) are time-consuming and expensive. The delivery systems for such devices have also suffered from problems relating to the repositionability of the devices as they are delivered into position in the living creature.

In stenting long arterial segments, the contiguously decreasing diameter of the arterial system from the center to the periphery may pose problems. Woven stents with a uniform diameter will exert a substantial expansile force to the vessel wall along the tapered portion. Additionally, the stent may remain more elongated in the tapered portion. In a study where WALLSTENTs with a uniform diameter were used to bridge central venous obstruction in hemodialysis patients, it was found that the stents which were selected according to the size of the larger diameter central vein exerted considerably higher force to the wall of the smaller caliber subclavian vein (Vesely, 1997). Simultaneously, the length of the stents in the smaller caliber vein was longer than expected.

In the prior art, most of the filter designs except for the Bird's Nest filter (Cook Inc., Bloomington, Ind.) have a conical shape and are anchored with multiple legs in the wall of the cava. The conical design is used because the main stream of the blood carries the thrombi from the lower part of the body through the center of the inferior vena cava. Therefore, all these devices are designed to have good filtration capacity at the center of the cava. The situation is quite different after some thrombi have been successfully captured. The center of the cava will no longer be patent and as a result, the blood will be diverted from the center to the periphery of the cava. The aforementioned designs, however, are not capable of catching thrombi effectively at the periphery of the lumen so the patients will practically be unprotected against subsequent peripheral embolization (Xian, 1995; Jaeger, 1998). Further, most of filters tend to be tilted in the cava which can deter their thrombus-capturing efficacy. Additionally, except for the Simon nitinol filter (C. R. Bard, New Jersey, N.J.) the aforementioned designs require a fairly large invasive delivery system of 10-F or larger.

The uniform caliber of cylindrical stents in the prior art used in the ureter, as well as the peristalsis arrested at the proximal end of the stent, has resulted in severe hyperlasia of the urothelium and eventually occlusion of the ureter.

Turning to occluders, percutaneous occlusion techniques have become indispensable tools in minimally invasive management of a wide range of pathological conditions. Use of permanent mechanical occlusion devices has been shown to be equivalent to that of surgical ligation. The Gianturco-Wallace stainless steel coil (Cook Inc., Bloomington, Ind.) has been the most widely used permanent, expandable intravascular occlusion device for transcatheter delivery (Gianturco et al., 1975).

Percutaneous coil embolization has been shown to be advantageous over traditional surgical procedures in treatment of life threatening hemorrhage due to trauma or obstetric emergencies (Schwartz et al., 1993; Teitelbaum et al., 1993; Selby Jr., 1992; Levey et al., 1991; Ben-Menachem et al., 1991; Vedantham et al., 1997). Furthermore, coils have been used alone or in combination with microvascular embolic agents for the treatment of vascular fistulas and malformations, tumors, and varices (Wallace et al., 1979; Hendrickx et al., 1995; Furuse et al., 1997; White et al., 1996; Sagara et al., 1998; Punekar et al., 1996). During the last few years, the transcatheter closure of the patent ductus arteriosus (PDA) with coils has become a frequently used technique (Hijazi and Geggel, 1994; Hijazi and Geggl, 1997).

Although coil type occlusion devices have shown at least a degree of utility, they have a number of drawbacks that could be significant in some applications. Intravascular stability of the coils has been shown to be highly dependent on proper matching of coil diameter with the diameter of the target vessel (Nancarrow et al., 1987), and with the exception of small vessels, a single coil rarely results in a stable occlusive thrombus (Hijazi and Geggel, 1994). Moreover, a long vascular segment is often obliterated because of the frequent need for multiple coils and the coils often remain elongated within the vessel because their unconstrained diameter is larger than the vascular lumen. Furthermore, delayed recanalization rates of 37%–57% have been reported in humans within 1–3 months after initially successful coil embolization (Sagara et al., 1998; O'Halpin et al., 1984; Schild et al., 1994).

These and other drawbacks have inspired modifications in the design and technique of coil embolization. Recently, detachable microcoils and macrocoils with controlled delivery have been designed to achieve a more compact conglomerate of the coil and to prevent migration by allowing optimal positioning of the coil before release (Zubillaga et al., 1994; Guglielmi et al., 1995; Marks et al., 1994; Reidy and Qureshi, 1996; Uzun et al., 1996; Tometzki et al., 1996; Dutton et al., 1995). However, since optimal arrangement of the coil alone may not prevent migration in some cases, such as high flow conditions or venous placement, a coil anchoring system has been devised (Kónya et al., 1998). Although an anchoring system may stabilize a coil conglomerate within the vasculature, significantly reducing or eliminating the possibility of coil migration, such a system may render the coil non-repositionable.

Several different non-coil devices have been designed to achieve a more stable, limited size plug with higher hemostatic efficiency particularly for transcatheter closure of larger vessels (Schmitz-Rode et al., 1993; Kato et al., 1997; Kónya et al., 1999) and PDAs (Pozza et al., 1995; Magal et al., 1989; Grifka et al., 1996). Recently, initial clinical experiences with a new self-expanding nitinol-mesh PDA occluder have been reported (Sharafuddin et al., 1996; Masura et al., 1998). A similar self-expanding, repositionable quadruple-disc device constructed of a braided nitinol mesh and polyester fibers has been reported to be superior to standard Gianturco coils in experimental occlusion of midsize arteries (Sharaffuddin et al., 1996).

Although such non-coil devices may be repositionable, they too exhibit drawbacks. For instance, the quadruple-disc device is several centimeters long in an elongated fashion, making difficult to keep the superselective position of the catheter tip during deployment. The multiple rigid connections between the layers and the relative long and rigid connection between the occluder and the delivery cable further increase this drawback. Although the nitinol mesh-PDA occluder has demonstrated utility, its proper placement requires a proper match both in size and shape between the occluder and the lesion to be occluded. The type and quality of the connection between the occluder and the delivery cable is the same as in the quadruple-disc design. A common disadvantage of both designs is that they lack guidewire compatibility. As a result, a delivery catheter must often be navigated to the site of occlusion first before an occluder may be loaded into the catheter and delivered through it. Another relative disadvantage of both devices is their cost of manufacturing.

Percutaneous catheter technique for permanent closure of isolated persistently patent ductus arteriosus (PDA) is now a treatment of choice among doctors, obviating open surgery. The configuration of the PDA varies considerably. A majority of PDAs tend to have a funnel or conical shape due to ductal smooth muscle constriction at the pulmonary artery insertion, although narrowings in the middle or aortic ends can be observed (Krichenko, 1989). That is the reason why not only the size, but also the configuration, of the lesion plays a significant role in selecting an appropriate occluding device. Except from the small caliber lesions (with a maximum diameter of 2.5 mm or 3.3 mm, respectively), where some authors have achieved successful closure of the PDA with Gianturco coils (Cambier, 1992; Lloyd, 1993; Sommer, 1994), Rashkind's "double umbrella" occluder is the most often used device for this purpose (Rashkind, 1987; Hosking, 1991; Latson, 1991; Wessel, 1988; Report of the European Registry, 1992). It is available in two sizes (with a diameter of 12 mm and 17 mm) which require a 8-F and 11-F delivery system, respectively.

In the majority of cases, the deployment of the traditional PDA device is performed from a femoral vein access (Report of the European Registry, 1992). Because of the size of the delivery sheath, such a device is not suitable for the treatment of patients with a body weight of less than 8 kg. Using even a larger umbrella, this procedure is not recommended for the treatment of the lesions with a diameter of 8 mm or above (Latson, 1991). About 80% of unselected patients with isolated PDA are candidates for the Rashkind device using the aforementioned criteria (Latson, 1991). With the Rashkind device, the proportion of patients with residual flow through the lesion fell from 76% immediately after implantation to 47% by the day after implantation and to 17% by a year after implantation (Report of the European Registry, 1992). According to some authors the residual flow carries a potential risk of infective endocarditis and should be avoided if possible. Its abolishment can be achieved by implantation of another device or surgery.

One of the main drawbacks of the Rashkind umbrella is that it is not suitable for occlusion of all types of PDA. Preferably, it is used to occlude short PDAs with relatively wide end-openings. Its two discs cover both the pulmonary and the aortic opening of the PDA. Longer PDA may hinder the discs to be positioned in the proper way, that is, parallel to each other, thereby deteriorating its self-anchoring. Another disadvantage of the umbrella is that the occluding capacity of the design depends exclusively on the thrombogenicity of the porous Dacron material, frequently resulting in partial and lengthy occlusion.

For the majority of patients with urinary leakage and/or fistulas (mainly due to tumor propagation to their ureters), the diversion of urine is currently performed by a percutaneous transrenal approach together with ureteral occlusion. Formerly, detachable and non detachable balloons were used for this purpose, but they did not cause satisfactory ureteral occlusion. Migration as well as deflation of the balloons occurred relatively frequently (Gunter, 1984; Papanicolau, 1985) leading to recurrence of the urine leakage. A silicone ureteral occluder was developed and used with only limited success because of device migration (Sanchez, 1988). This resulted in repositioning and consequent incomplete ureteral occlusion. It appears that the best results have been accomplished with Gianturco coils and Gelfoam embolization (Gaylord, 1989; Bing, 1992 a; Farrel, 1996). Even with multiple coil placements, together with Gelfoam plugs, the ureteral occlusion may sometimes be achieved for only weeks or months, and was attributed mostly to the induced urothelial hyperplasia (Bing, 1992 b). Coil migration was frequently encountered in these studies. The lack of appropriate self-anchoring results in coil migration which eventually deteriorates the occlusive effect.

Problems pointed out in the foregoing are not intended to be exhaustive but rather are among many that tend to impair the effectiveness of previously known stents, occluders and filters. Other noteworthy problems may also exist; however, those presented above should be sufficient to demonstrate that previous techniques appearing in the art have not been altogether satisfactory, particularly in providing flexible, self-expanding, repositionable stents, occluders and filters.

SUMMARY OF THE INVENTION

The present invention overcomes the problems inherent in the prior art by providing a self-expandable, repositionable device for use as a stent, an occluder, or a filter which may be formed using a plain weave, and may have closed structures at both its ends.

In one respect, the invention is a device that includes, but is not limited to, a plurality of shape memory wires woven together to form a body suitable for implantation into an anatomical structure. The body has first and second ends. The shape memory wires cross each other to form a plurality of angles, at least one of the angles being obtuse. Both ends of at least one shape memory wire are located proximate one end of the body. The value of the obtuse angle is increased when the body is axially compressed.

The shape memory wires may be made of nitinol. The shape memory wires may be made of FePt, FePd or FeNiCoTi. The shape memory wires may be made of FeNiC, FeMnSi or FeMnSiCrNi. The shape memory wires may each have a diameter ranging in size from about 0.006 inches to about 0.012 inches. The plurality of shape memory wires may include at least 6 shape memory wires. The body may have a tubular shape with a substantially uniform diameter. The body may have a tapered shape with a diameter that decreases from one end of the body to the other end of the body. The body may have a generally hourglass shape. As used herein, "a generally hourglass" shape is a shape that resembles a body having two ends that are larger in terms of cross-sectional area than a mid-portion located therebetween. Such shapes include those resembling traditional hourglasses or dumbbells, for example. The body may be woven by hand. The body may be woven by a machine, such as a braiding machine.

The device may also include, but is not limited to, a graft material attached to the body. The graft material may be made from woven polyester. The graft material may be made from Dacron. The graft material may be made from polyurethane. The graft material may be made from PTFE. The graft material may partially cover the body. As used herein, a graft material that "partially covers" a body is attached to the body such that a portion of the wire or wires forming the body are left bare or exposed. As a result of only partially covering a body, blood or other bodily fluids may flow through the bare portion of the body relatively unimpeded by the graft material.

The device may also include, but is not limited to, a first tube that is configured to accept a guide wire and a second tube that is configured to fit over the first tube. Prior to delivering the body into an anatomical structure, the second tube is placed over the first tube, one end of the body is secured to the first tube and the other end of the body is secured to the second tube.

In another respect, the invention is a device that includes, but is not limited to, a body suitable for implantation into an anatomical structure. The body has a first end, a second end and is defined by at least n shape memory wires, wherein n is greater than one. The n shape memory wires are arranged such that the body includes a first portion. The first portion includes a first woven portion and at least one strut. The shape memory wires of the first woven portion cross each other to form a plurality of angles, at least one of the angles being obtuse. Both ends of at least one shape memory wire are located proximate one end of the body. The value of the obtuse angle is increased when the body is axially compressed.

The shape memory wires may be made from nitinol. The shape memory wires may be made from FePt, FePd or FeNiCoTi. The shape memory wires may be made of FeNiC, FeMnSi or FeMnSiCrNi. The first portion may include a first woven portion separated from a second woven portion by multiple first struts.

The body may also include, but is not limited to, a second portion located adjacent to the first portion. The second portion includes a second woven portion. The second portion has n+x shape memory wires, and x is at least one. The first portion may have a generally domed shape. The first woven portion may have a generally domed shape and the multiple first struts may be bent slightly so as to increase the self-anchoring capability of the body in an anatomical structure. The first portion may also include a third woven portion separated from the second woven portion by multiple second struts. The first and third woven portions may have generally domed shapes.

The device may also include, but is not limited to, a graft material attached to the body. The graft material comprises may be made from woven polyester. The graft material may be made from Dacron. The graft material may be made from polyurethane. The graft material may be made from PTFE. The graft material may partially cover the body.

The device may also include, but is not limited to, a first tube that is configured to accept a guide wire and a second tube that is configured to fit over the first tube. Prior to delivering the body into an anatomical structure, the second tube is placed over the first tube, one end of the body is secured to the first tube and the other end of the body is secured to the second tube.

In another respect, the invention is a device that includes, but is not limited to, a plurality of biodegradable filaments woven together to form a self-expanding body suitable for implantation into an anatomical structure. The self-expanding body has a first end and a second end. The biodegradable filaments cross each other to form a plurality of angles, at least one which is obtuse. The value of the obtuse angle is increased when the body is axially compressed.

The biodegradable filaments may be made from polyglycolic acid. The biodegradable filaments may be made from poly-L-lactic acid. The biodegradable filaments may be made from a polyorthoester. The biodegradable filaments may be made from a polyanhydride. The biodegradable filaments may be made from a polyiminocarbonate. The biodegradable filaments may be made from an inorganic calcium phosphate. The biodegradable filaments may include about 0.05 to 0.25 percent by weight of calcium oxide, calcium hydroxide, calcium carbonate, calcium phosphate, magnesium oxide, magnesium hydroxide, magnesium carbonate, magnesium phosphate, sodium phosphate or potassium sulfate. The biodegradable filaments may be made from a polymer having about 15 to about 30 mole percent glycolide. At least one of the biodegradable filaments may be made from paclitaxel, docetaxel or heparin. Both ends of at least one biodegradable filament may be located proximate the first end of the self-expanding body. Each end of the self-expanding body may include at least one closed structure.

The device may also include, but is not limited to, at least one shape memory wire secured to the self-expanding body. Both ends of the one shape memory wire may be located proximate one end of the self-expanding body.

In another respect, the invention is a method of creating a body suitable for implantation into an anatomical structure. The body has two end ends. The method includes, but is not limited to, bending the shape memory wires in a plurality of shape memory wires to create bent portions in the shape memory wires. The bent portions are arranged to define one end of the body. Each shape memory wire has two ends. The method also includes, but is not limited to, weaving the ends of the shape memory wires to create the body such that the shape memory wires cross each other to form a plurality of angles, at least one of the angles being obtuse. The value of the obtuse angle is increased when the body is axially compressed.

The bent portions may be bends or loops. The shape memory wires may be made from nitinol. The shape memory wires may be made of FePt, FePd or FeNiCoTi. The shape memory wires may be made of FeNiC, FeMnSi or FeMnSiCrNi. The shape memory wires may each have a diameter ranging in size from about 0.006 inches to about 0.012 inches. The plurality of shape memory wires may include at least 6 shape memory wires. The body may have a tubular shape with a substantially uniform diameter. The body may have a tapered shape with a diameter that decreases from one end of the body to the other end of the body. The body may have a generally hourglass shape. The body may be woven by hand. The body may be woven by a machine, such as a braiding machine.

In another respect, the invention is a method of creating a body suitable for implantation into an anatomical structure. The body has two ends. The method includes, but is not limited to, providing a weaving system that includes a template having first template projections. The method also includes, but is not limited to, bending shape memory wires around the first template projections to create bent portions in the shape memory wires. The bent portions are arranged to define one end of the body. Each shape memory wire has two ends. The method also includes, but is not limited to, weaving the ends of the shape memory wires around the template to create the body such that the shape memory wires cross each other to form a plurality of angles, at least one of the angles being obtuse. The value of the obtuse angle is increased when the body is axially compressed.

The first template projections may be tabs. The first template projections may be pins. The pins may be attached to a ring engaged with the template. The weaving system may also include, but is not limited to, a first weaving plate configured to rotate in a first direction during the weaving. The weaving system may also include, but is not limited to, first bobbins arranged on the first weaving plate, and one end of each shape memory wire is attached to each first bobbin prior to the weaving. The weaving system may also include, but is not limited to, a second weaving plate configured to rotate in a second direction during the weaving, and the second weaving plate is spaced apart from the first weaving plate. The weaving system may also include, but is not limited to, second bobbins arranged on the second weaving plate, and one end of each shape memory wire is attached to each second bobbin prior to the weaving. The method may also include, but is not limited to, securing the shape memory wires to the template. The method may also include, but is not limited to, forming closed structures with the ends of the shape memory wires. The closed structures may be arranged to define the other end of the body. The method may also include, but is not limited to, heating the body and the template.

In another respect, the invention is a device for delivering an axially and radially expandable woven body having two ends into an anatomical structure. The device includes, but is not limited to, a first tube configured to accept a guide wire, and a second tube configured to fit over the first tube. When the tubes are used for delivering the axially and radially expandable woven body, one end of the axially and radially expandable woven body is secured to the outside of the first tube and the other end of the axially and radially expandable woven body is secured to the outside of the second tube.

The first tube may be made from NYLON or TEFLON. The second tube may be made from NYLON or TEFLON. The device may also include, but is not limited to, a guide wire configured to be placed within the first tube. The outer diameter of the first tube may range in size from 3 French to 7 French. The outer diameter of the second tube may range in size from 5 French to 9 French. The device may also include, but is not limited to, a push-button release/lock mechanism configured to secure the first tube to the second tube. The device may also include, but is not limited to, an end fitting having a side arm. The end fitting is configured to be secured to the first tube. The first tube may be provided with at least one pair of first tube holes through which a first securing wire may be threaded. The pair of first tube holes may be positioned proximate one end of the first tube. The second tube may be provided with at least one pair of second tube holes through which a second securing wire may be threaded. The pair of second tube holes may be positioned proximate one end of the second tube.

In another respect, the invention is a device for delivering an axially and radially expandable woven body having two ends into an anatomical structure. The device includes, but is not limited to, a first tube configured to accept a guide wire. The first tube has at least one pair of first tube holes that are positioned proximate one end of the first tube. The device also includes, but is not limited to, a second tube configured to fit over the first tube. The second tube has at least one pair of second tube holes that are positioned proximate one end of the second tube. The device also includes, but is not limited to, a first securing wire configured to be threaded through the pair of first tube holes. The device also includes, but is not limited to, a second securing wire configured to be threaded through the pair of second tube holes. When the tubes are used for delivering the axially and radially expandable woven body, one end of the axially and radially expandable woven body is secured to the outside of the first tube with the first securing wire and the other end of the axially and radially expandable woven body is secured to the outside of the second tube with the second securing wire.

In another respect, the invention is an occluding system that includes, but is not limited to, a plurality of shape memory wires woven together to form a body useful for occluding an anatomical structure. The body has first and second ends. Both ends of at least one shape memory wire are located proximate one end of the body. The shape memory wires cross each other to form a plurality of angles, at least one of the angles being obtuse. The value of the obtuse angle is increased when the body is axially compressed.

The shape memory wires may be made from nitinol. The occluding system may also include, but is not limited to, an occluding agent enclosed within the body. The occluding agent may include one or more threads of polyester. The occluding agent may also include, but is not limited to, one or more threads of DACRON. The occluding system may also include a jacket coupled to the body. The jacket may be made from silicone. The jacket may be made from polyurethane. The occluding system may also include, but is not limited to, a first tube configured to accept a guide wire, and a second tube configured to fit over the first tube. Prior to delivering the body into an anatomical structure, one end of the body is secured to the outside of the first tube and the other end of the body is secured to the outside of the second tube.

In another respect, the invention is a device that includes, but is not limited to, a body suitable for implantation into an anatomical structure. The body has an axis, a first end and a second end. The body is made from a shape memory wire that has a first segment and a second segment. The segments are separated by a bend in the shape memory wire that is located proximate one end of the body. The first segment extends helically in a first direction around the axis toward the other end of the body. The second segment extends helically in a second direction around the axis toward the other end of the body. The first and second segments cross each other in a plurality of locations.

The first segment may be positioned farther from the axis than the second segment at at least one location. The first segment may be positioned farther from the axis than the second segment at each location. The shape memory wire may be made from nitinol. The device may also include a first tube configured to accept a guide wire, and a second tube configured to fit over the first tube. Prior to delivering the body into an anatomical structure, one end of the body is secured to the outside of the first tube and the other end of the body is secured to the outside of the second tube.

In another respect, the invention is a device that includes, but is not limited to, a body suitable for implantation into an anatomical structure. The body has a first end and a second end. The body is formed from a shape memory wire that has a first segment and a second segment. The segments are separated by a bend in the wire that is located proximate one end of the body. The first segment and second segments are arranged to form loops and twisted segments such that at least two contiguous loops are separated from another loop by a twisted segment. The definition of "contiguous" is set forth below with reference to the figures herein for the sake of clarity.

At least three contiguous loops may be separated from another loop by a twisted segment. At least four contiguous loops may be separated from another loop by a twisted segment. At least two contiguous loops may be separated from two other contiguous loops by a twisted segment. The shape memory wire may be made from nitinol. The device may also include, but is not limited to, a first tube configured to accept a guide wire, and a second tube configured to fit over the first tube. Prior to delivering the body into an anatomical structure, one end of the body is secured to the outside of the first tube and the other end of the body is secured to the outside of the second tube.

In another respect, the invention is a device that includes a body suitable for implantation into an anatomical structure. The body has, but is not limited to, two ends and is formed from a shape memory wire that has a first segment and a second segment. The segments are separated by a bend in the wire that is located proximate one end of the body. The segments are positioned adjacent to each other in loop-defining locations. The segments also extend between the loop-defining locations in spaced relation to each other so as form at least two loops. At least one of the at least two loops has a compressed shape. The definition of a "compressed" shape is set forth below with reference to the figures herein for the sake of clarity.

The shape memory wire may be made from nitinol. The segments may be secured together using welds at the loop-defining locations. The segments may be secured together with collars at the loop-defining locations. The body may also include, but is not limited to, at least one coil placed over at least a portion of one of the segments, and, as a result, the body may be used as an occluder. The body may also include at least one fiber attached to the coil. The device may also include, but is not limited to, a first tube configured to accept a guide wire, and a second tube configured to fit over the first tube. Prior to delivering the body into an anatomical structure, one end of the body is secured to the outside of the first tube and the other end of the body is secured to the outside of the second tube.

The present invention also provides a delivery system that may secure both the proximal and distal ends of the stent, occluder or filter. Advantageously, this delivery system allows the stent, occluder or filter to be easily repositioned as it is being delivered into place. As a result, the stent, occluder or filter may be more precisely positioned within the living creature.

One advantage of the present invention is the unique fixation method of the tapered stent. The tapered shape of the stent allows the stent to be fixed in a tapered vessel or tubular structure with less radial or expansile force than a straight stent might exhibit, thus potentially resulting in a less hyperplastic intimal reaction.

The straight stent of the present invention exhibits a high expansile force and thus a large capability of withstanding outer compression. This may be especially advantageous in tumorous stenoses, or fibrous strictures (including radiation-induced stenoses) where stents with inadequate expansile forces can be easily compressed and/or are incapable of assuming their nominal shape and diameter. In some cases, even the stenoses of arteriosclerotic origin can be so calcified (e.g., iliac or renal artery stenoses) that extra radial force is required from the stent to hold the patency of the vessel. Furthermore, the woven intravascular devices of the present invention are also able to return to their original, unconstrained shape after being bent, even maximally.

Advantageously, the stents, occluders and filters of the present invention do not possess free, sharp wire ends. Thus, many potential complications are eliminated (Prahlow, 1997). Additionally, the tight mesh of the stents of the present invention coupled with the use of nitinol wires, for example, makes them easy to monitor under fluoroscopy.

The present invention also includes a group of self-expanding, self-centering cava filters woven from materials as described above such that a coherent element is formed that without the use of a joint or attachment between the portions of the filters. The cava filters of the present invention provide increased filtrating efficiency not only at the center but also at the periphery of the cava. Additionally, the hourglass filter of the present invention utilizes multiple filtration levels. The cava filters of the present invention are able to self-center due to the symmetrical nature of their design and their potentially flared base.

The cava filters of the present invention may utilize a relatively small, 7 French delivery catheter or sheath. Additionally, the superb flexibility of the cava filters makes it possible to deliver them via any of the possible access sites of the human body (femoral, jugular, antecubital veins).

The present invention also includes a bi-iliac filter ("BI filter") that is a low-profile, self-expanding, flexible, temporary filter which may be woven from a number of super-elastic or shape memory alloys. The BI filter is a type of temporary filter that can be deployed from either femoral vein, and it can filtrate the blood at the iliac veins/inferior cava junction. The BI filter of the present invention typically works at a low level of venous circulation. Advantageously, the BI filter simultaneously filters all the blood coming from both iliac veins, achieving almost 100% filtration. Further, the use of the BI filter is particularly beneficial in perioperative and posttraumatic cases.

The inverse U-shape of the BI filter together with the expansile force of the tubular weave ensures firm position along the iliac/cava junction. A further advantage of the present invention is that the BI filter may utilize a relatively small, 7 French delivery catheter or sheath. Further, due to the flexibility of the mesh of the BI filter, the delivery system thereof may be advanced from ipsi- to contralateral iliac vein. As with the cava filters, the BI filter may possess a non-ferromagnetic character making it MRI compatible.

The BI filter is suitable for temporary filtration. The BI filter allows for removal of the entrapped thrombi safely and successfully before removal of the filter. Using an adequately sized sheath, the small thrombus fragments entrapped within the mesh could also be removed together with the filter.

The stents of the present invention can be advantageously covered with materials such as silicone, polyurethane, and/or an anticancer coating agent that allow the stents to reduce the possibility of restenosis after delivery, and which also allow the stents to be used in stenting malignant stenoses, for example. The filters of the present invention may also be covered with anticoagulant coating agents.

Ureter strictures/compression/occlusion may be stented with these uncovered and/or covered stents; in particular, the use of a long tapered stent may advantageously match the special conditions posed by the different caliber and distensibility of the different segments of the ureter as well as the constant peristalsis.

The stents of the present invention can also be used in some non-vascular applications including biliary tree and tracheo-bronchial system if the lesion does not require a bifurcated stent.

The stents, occluders and filters of the present invention may be used in many different applications. They provide the advantages of superb flexibility, repositionability/removability, and precise positionability.

BRIEF DESCRIPTION OF THE DRAWINGS

The following drawings form part of the present specification and are included to further demonstrate certain aspects of the present invention. The invention may be better understood by reference to one or more of these drawings in combination with the description of illustrative embodiments presented herein.

FIGS. 5A–E sequentially illustrative steps in a delivery method according to one embodiment of the present invention.

FIG. 6 is a front view of a conical filter having bends or loops in the proximal (rear) end thereof according to one embodiment of the present invention.

FIG. 7 is a front view of a conical filter having bends or loops in the distal (front) end thereof according to one embodiment of the present invention.

FIG. 8 is a front view of a dome filter having bends or loops in the distal end thereof according to one embodiment of the present invention.

FIG. 9 is a front view of an hourglass filter according to one embodiment of the present invention.

FIG. 10 is a front view of an hourglass filter according to one embodiment of the present invention placed in the Inferior Vena Cava.

FIG. 30A is a front view of two wires coupled together for use in a hand weaving method according to one embodiment of the present invention.

FIG. 30B is a perspective view of the placement of two wires each coupled to a pin for use in a hand weaving method according to one embodiment of the present invention.

FIG. 31 is a perspective view of a biodegradable stent with a reinforcing wire according to one embodiment of the present invention.

FIGS. 33A–G are front views of various configurations of an occluder according to the present invention.

FIG. 34 is a front view of an occluder having a jacket according to one embodiment of the present invention.

FIG. 35 is a front view of an occluder having clips according to one embodiment of the present invention.

FIG. 45 is a perspective view of upper and lower weaving plates provided with bobbins and wires and arranged around a template such that the surfaces of the weaving plates from which the bobbin rods extend face each other according to one embodiment of the present invention.

DESCRIPTION OF ILLUSTRATIVE EMBODIMENTS

1. Stents

Straight Stents

Figure 1C:
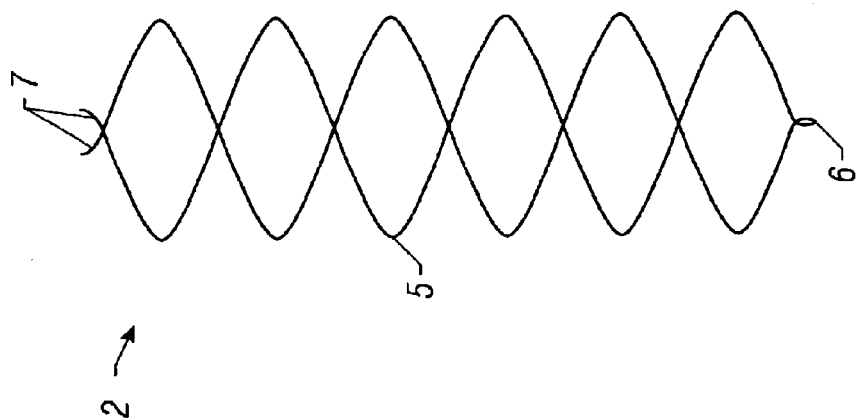
FIG. 1C is a perspective view of one wire of a stent according to one embodiment of the present invention.
Figure 1B:
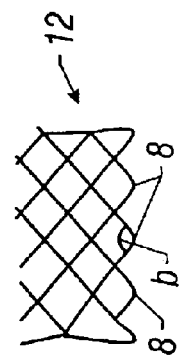
FIG. 1B is a front view of a stent end defined by bends according to one embodiment of the present invention.
Figure 1A:
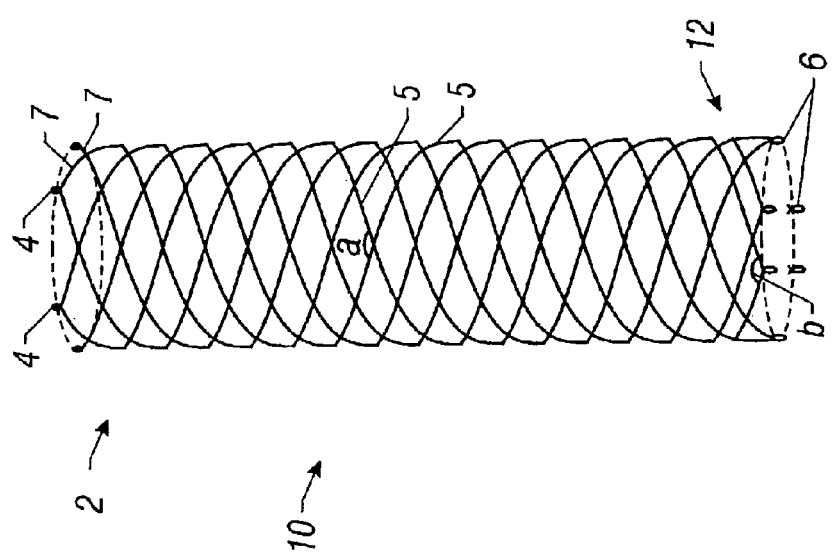
FIG. 1A is a perspective view of a stent according to one embodiment of the present invention.

With reference to the illustrative embodiment shown in FIG. 1A, there is shown a stent for insertion and delivery into an anatomical structure. The stent includes a plurality of wires 5 which may be arranged in a plain weave so as to define an elastically deformable body 10. As used herein, "elastically deformable" means that the deformation of such a body is non-permanent and an original or initial shape may be substantially recovered, or regained, upon the release of a force (which may be mechanical, electromagnetic, or any other type of force). As used herein, "substantially recovered" means that recovery need not be such that the exact, original shape be regained. Rather, it means that some degree of plastic deformation may occur. In other words, recovery need not be total. Such elastic deformability may be achieved by utilizing the superelastic properties of suitable shape memory wires, which are discussed below.

Figure 2:
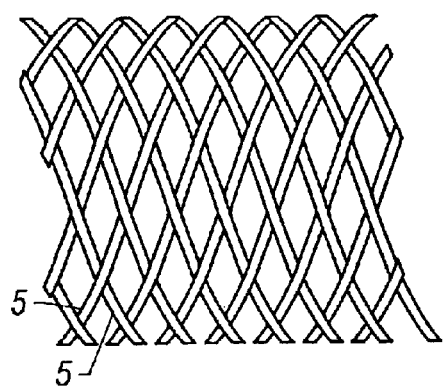
FIG. 2 is a side view of the arrangement of wires in a plain weave according to one embodiment of the present invention.

U.S. Pat. No. 4,655,771 to Wallsten (1987), which is hereby expressly incorporated by reference, displays the manner in which wires cross each other using plain weave as shown in FIG. 1*a* therein. FIG. 2 also illustrates the manner in which the wires 5 of the present intravascular devices may be arranged utilizing a plain weave.

Body 10 is both radially and axially expandable. Body 10 includes front or distal end 12 and rear or proximal end 2. As shown in FIG. 1A, end 12 has a plurality of closed structures. These closed structures may be small closed loops 6 or bends 8 (FIG. 1B). Both bends 8 and small closed loops 6 may be formed by bending a wire 5 at a selected point located between the ends 7 of wire 5 (FIG. 1C shows small closed loops 6). For most applications, the selected point of the bend or small closed loop may be close to the midpoint of wire 5, as shown in FIG. 1C with respect to small closed loop 6. FIG. 1C also shows both ends of wire 5 being located proximate end 2 of body 10 (although the remainder of body 10 is not shown). Body 10 is formed by plain weaving wires 5, as will be discussed below in greater detail.

Loops 6 and bends 8 provide significant advantages, some of which are unexpected, over woven devices such as the WALLSTENT that have free wire ends. For instance, the Wallsten patent recognizes that the free wire ends of the WALLSTENT should be protected, implicitly acknowledging the potential tissue-damaging dangers such free, sharp wire ends pose. The Wallsten patent suggests methods by which one can attempt to lessen these dangers, such as connecting the free wire ends to each other by attaching U-shaped members to them through heat welding, gluing or the like. These suggested methods can be time-consuming and, as a result, expensive. No such steps need to be taken in creating either loops 6 or bends 8 of the present woven devices as will be discussed below in greater detail.

Further, the connections resulting from the methods disclosed in the Wallsten patent are likely more prone to mechanical failure than are loops 6 or bends 8 of the present woven devices. For example, welding can introduce anomalies such as cracks (which may result from the non-uniform solidification, uneven boundaries, etc.); voids or other irregularities resulting from porosity; inclusions (which include slag, oxides, etc.); etc., into the welded metal that create stress concentrations and dramatically increases the propensity for the welded connection to fail at those locations. In contrast, the gentle curves and bends resulting in loops 6 and bends 8 are virtually free of any such induced stresses and, as a result, are much less likely to fail.

The Wallsten patent also suggests gluing the free wire ends, a method that provides even less structural integrity than can welding, because the resulting bond between the joined wire ends is only as strong as the surface tension between the glue and the metal used. Consequently, the joint created is more prone to failure than a welded joint suffering from the anomalies just discussed.

Similarly, the Wallsten patent discloses first utilizing electric resistance heating to weld together the points of crossing of the free wire ends in a ring around the stent and then folding the free wire ends extending beyond the welded ring inwardly with light plastic deformation through controlled heating. This method involves not only the likely introduction of the anomalies discussed above that can result from welding, it also involves an additional stress on the joints created as the free wire ends are folded inwardly while being heated. Thus, this preferred joint is similar to the glued joint in that it is likely even more prone to failure than one involving only welding.

In sum, the gentle curves and bends that may be used to create loops 6 and bends 8 of the present woven devices provide devices with safer ends: no free wire ends exist that may unintentionally penetrate and damage the wall of the structure into which they are delivered; the bends 8 or loops 6 are much less likely to mechanically fail than are the free wire ends that are connected together using welding or glue; and the likely time-consuming task of creating multiple welded or glued joints does not exist. Further, while the closed structures 4 (discussed below in greater detail) may be reinforced using methods similar to those suggested by the Wallsten patent (i.e., such as by welding), the present woven devices have, at most, only half as many potential locations for using such methods (and most likely less than half considering fewer wires are generally needed for making the present stents than are needed for making comparably-sized WALLSTENTS, even equating one of the present wires to two wires as those are used in the WALLSTENT). As a result, the potential for mechanical failure of the present woven devices is reduced accordingly.

In addition to the foregoing benefits, loops 6 and bends 8 also provide advantages over the modified free wire ends disclosed in the Wallsten patent discussed above that are unexpected. For example, the inventors have found that the mesh of one of the present woven stents may be formed from fewer wires than can the mesh of a comparably-sized WALLSTENT (even equating one of the present wires to two wires as those are used in the WALLSTENT). Accordingly, the expansile force of one of the present woven stents of a given size may be maintained with fewer wires than would be needed to maintain the same expansile force of a WALLSTENT of the same size by simply increasing the mesh tightness (i.e., by increasing angle a—FIG. 1A—discussed below in greater detail). Similarly, the inventors have found that the same result may be achieved by increasing the diameter of the present wires with or without adjusting the mesh tightness. As a result, the amount of metal needed for the present woven stents may be less than what is needed in another comparably-sized woven stent, such as the WALLSTENT. This reduction in necessary metal translates to a cost savings, and, as described above, also means that patients are less likely to experience thrombosis and/or restenosis. As a further result, the variety of sizes that may be created for the present stents and the variety in the tightness of the weave of each is virtually unlimited, thereby facilitating virtually all potential applications.

Further, the inventors also discovered that virtually no shortening occurs while bending the present woven stents, nor do the diameters of the present woven stents increase during bending. Thus, it is easier to accurately and predictably position the present stents in a tortuous anatomy than it is to position other woven stents that shorten more or suffer larger increases in diameter when bent, such as the WALLSTENT. For example, a tightly-woven present stent, 2.5 cm long, 10 mm in diameter, formed from 10 0.006-inch wires may be maximally bent by simply holding the two ends thereof between two fingers and bringing those ends together, and no shortening or diameter increase occurs during maximal bending. In contrast, for a WALLSTENT formed from 24 0.005-inch wires to behave similarly, the inventors found that it should be 6 cm long and 9 mm in diameter; although, when manipulated in a similar manner, the WALLSTENT experienced a 10% increase in diameter and some shortening. Thus, the length-to-diameter ratios of the foregoing stents were 2.5 and 6.6, respectively.

As few as five wires, and an unlimited maximum number of wires may be used to form body 10 for any given application. As used herein, "wires" will mean a strand formed of any material, such as metal, plastic, fiber, etc. In an exemplary embodiment of the present invention, 6 to 12 wires are typically used to form body 10 in most applications.

The number of wires that may be used depends on the application, and specifically on the desired expansile force of the stent. The expansile force of the stent is the radial force necessary to reduce the diameter of the stent. Factors affecting the expansile force of the stent include: the tightness of the weave (which is determined by the number of wires used and the angle formed by the crossed wires—the more wires or the closer the angle is to 180°, the tighter the weave), the number of wires used to form the woven stent, and the diameter of the wires used. When body 10 is used in the coronary artery, for example, it may be desirable to use the smallest possible amount of wire material to prevent thrombosis and reduce the possibility of restenosis in the vessel with a relatively slow circulation.

In FIG. 1A, when body 10 is in its initial, unconstrained shape, angle a may range from about 90° up to, but not including, 180°. The expansile force of body 10 increases as angle a approaches 180°. It is to be understood that angles less than 90° may be utilized for angle a. In an exemplary embodiment, angle a is preferably obtuse, i.e., more than 90°, and most preferably about 150°. In certain applications, however, a larger expansile force may be desirable, and, thus, angle a may be closer to 180°, such as in the case of a tumorous stricture or the like. In this regard, in an in vitro comparative study, a stent according to the present invention exhibited a higher expansile force and thus a larger capability of withstanding outer compression than both a Z-stent and a WALLSTENT of the same diameter, as revealed in Table 1, below. In Table 1, the designation Δ in the leftmost column represents, the circumferential displacement (in mm) of the stent in question. For example, a Δ of 2 mm indicates that the circumference of the stent in question was reduced by 2 mm, and the force necessary to effect that displacement was then recorded. The designation "W" refers to the WALLSTENT.

TABLE 1

Comparison of Expansile Forces of a Z-Stent, a WALLSTENT and a Nitinol Woven Stent

| Δ (mm) | Z Center | Z Between | Z Side by Side | W Center | W Overlap | W Side by Side | Woven Stent |
|---|---|---|---|---|---|---|---|
| 2 | 16 | 13 | 19 | 15 | 35 | 18 | 44 |
| 4 | 36 | 28 | 31 | 25 | 59 | 22 | 91 |
| 6 | 51 | 44 | 42 | 42 | 80 | 35 | 126 |
| 8 | 63 | 61 | 56 | 50 | 108 | 42 | 158 |
| 10 | 81 | 79 | 62 | 60 | 126 | 48 | 167 |
| 12 | 100 | 98 | 76 | 74 | 149 | 54 | 175 |
| 14 | 115 | 119 | 90 | 84 | 170 | 63 | 184 |
| 16 | 127 | 133 | 101 | 100 | 197 | 73 | 202 |
| 18 | 146 | 192 | 122 | 111 | 220 | 84 | |
| 20 | 165 | unmeasur. | 142 | 129 | 248 | 96 | |

With respect to Table 1, the unit "g" for "grams" is used as a measure of force. Although the correct unit of force is the "dyne", which is equal to the mass in grams multiplied by the gravitational constant, the inventors believe that the average reader will have a better idea about the size of force when the associated mass unit (grams) is specified.

When one uses, e.g., a WALLSTENT or other commercially available stent for stenting, the manufacturer usually recommends to use a stent one mm larger than the diameter of the vessel, after precise determination of the size of the vessel, to eliminate the magnification factor caused by the fluoroscopy/radiography. This minimal "overstenting" is used to achieve good contact between the stent and the vessel wall. The manufacturer also typically provides exact data regarding the relationship between the stent's diameter and length to facilitate precise positioning thereof. The woven nitinol design of the present invention has significantly greater expansile force than that of the WALLSTENT if a comparable number of wires are used to form the same caliber stent (understanding that one wire as used herein and shown in FIG. 1C would require the use of two wires in the WALLSTENT, given the free, unclosed wires thereof). Compared to the WALLSTENT, the closed structures of the stents of the present invention and the better shape memory of the wires that may be used may result in a considerable reduction in the size of the wires used, in the number of wires used, as well as in the angles between the wires. For instance, in small vessel applications (e.g., coronary artery) it is advantageous to use the minimum amount of wire (metal) to reduce the possibility of thrombosis and/or restenosis. Furthermore, in preferred embodiments, angle a may be reduced below 90 degrees without losing the necessary expansile force for self anchoring. For the same vascular application, the same or even greater expansile force can be achieved with a loosely-woven nitinol design of the present invention compared to the WALLSTENT and other available stents. A stent of the present invention may also be chosen so as to have a diameter approximately ten percent larger than the diameter of the tubular structure to be stented.

Figure 50A:
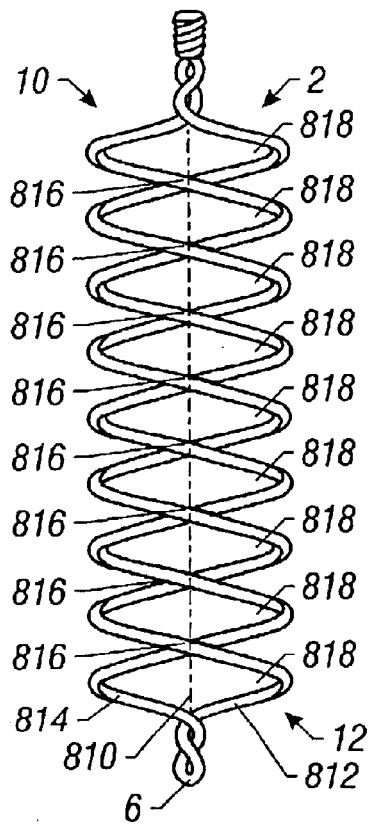
FIG. 50A is a front view of a stent formed from a single wire according to one embodiment of the present invention.

Body 10 may also be formed from a single wire ("the single wire embodiment"). The single wire embodiment is illustrated in FIG. 1C, wherein wire ends 7 have not yet been twisted or coupled together to form a closed structure 4, as described below in greater detail. One version of the single wire embodiment is illustrated in FIG. 50A. As illustrated in FIG. 50A, body 10 of the stent has an axis 810, distal end 12 and proximal end 2. First segment 812 of wire 5 is separated from second segment 814 by either bend 8 (not shown) or closed loop 6. As shown in FIG. 50A, first segment 812 extends helically in a first direction around axis 810 toward end 2, and second segment 814 extends helically in a second direction around axis 810 toward end 2. First segment 812 crosses second segment 814 in a number of locations 816. As shown in FIG. 50A, locations 816 define loops 818, which touch each other such that the loops are contiguous. Loops 818 are "contiguous" because, with the exception of the first and last loops, each loop shares a point—location 816—with two other loops.

Segments 812 and 814 may be arranged in two different ways with respect to each other. As shown in FIG. 50A, segment 812 is positioned farther from axis 810 than segment 814 at each location 816, while in FIG. 50B, segments 812 and 814 alternate being further from axis 810 at each location 816. It will be understood to those of skill in the art, with the benefit of this disclosure, that segment 812 may be positioned farther from axis 810 than segment 814 at one or more locations 816.

Figure 50B:
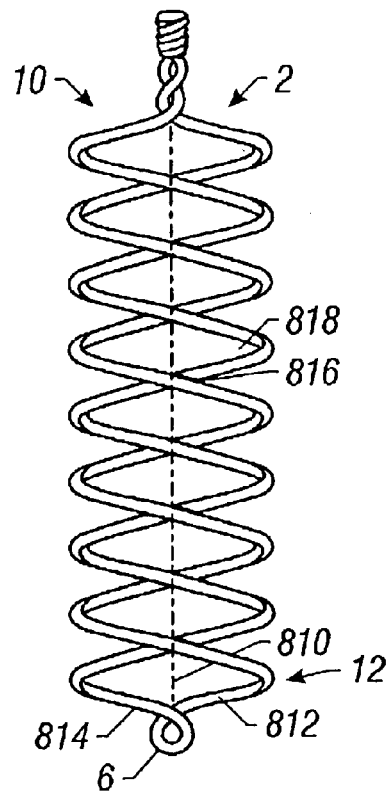
FIG. 50B is a front view of a stent formed from a single wire according to a second embodiment of the present invention.

In the single wire embodiment of the stents in FIGS. 50A and 50B, loops 818 reside in a series of planes that includes two groups of planes (not shown), one of which includes the planes passing through the first, third, fifth, etc. loops 818, and the other of which includes the planes passing through the second, fourth, sixth, etc. loops 818. The planes in each group are roughly parallel to each other. When body 10 is in its unconstrained state, the planes in one of the groups intersect the planes in the other group at acute angles falling within the range of slightly greater than 0° to about 45°. Axis 810 passes generally through the center of each of loops 818.

Figure 50C:
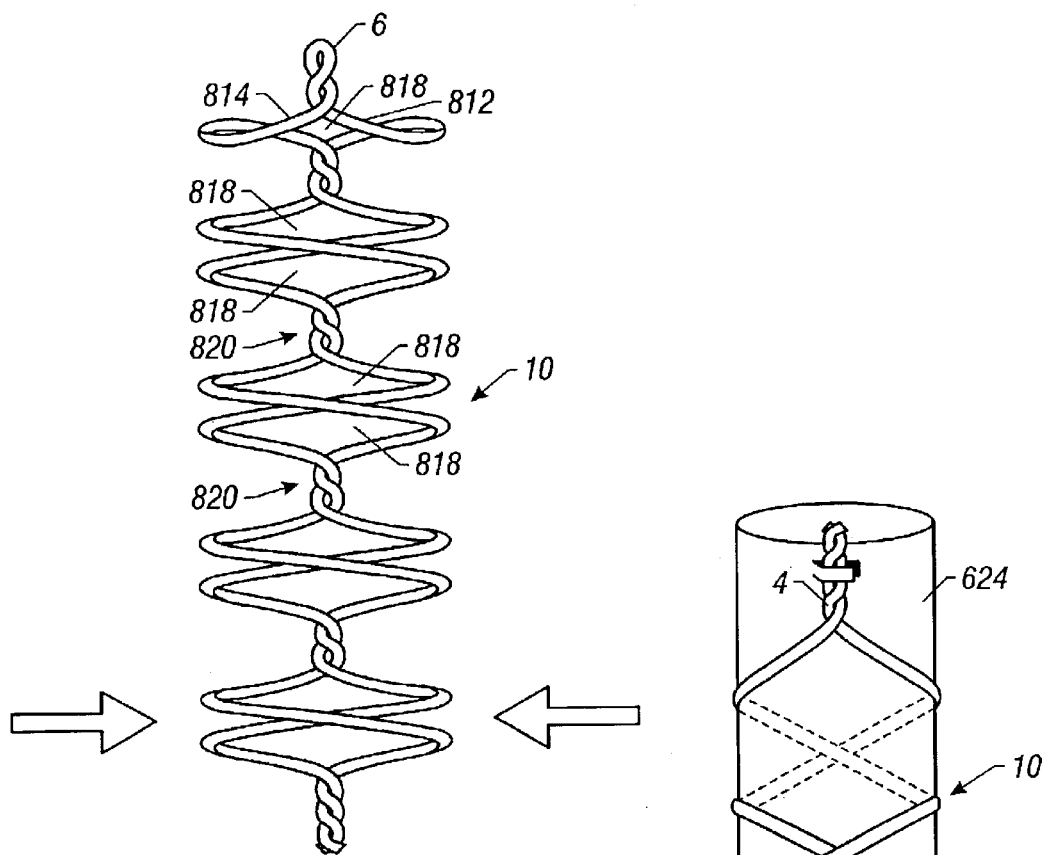
FIG. 50C is a front view of a stent formed from a single wire according to a third embodiment of the present invention.
Figure 50D:
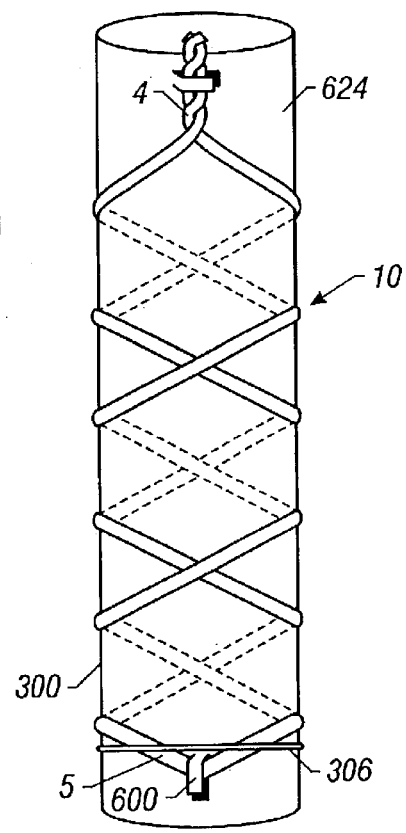
FIG. 50D is a perspective view of the stent depicted in FIG. 50B positioned on a template according to one embodiment of the present invention.

As shown in FIG. 50C, certain of loops 818 of the single wire embodiment of body 10 of the stent may be separated by longitudinal segments in which segments 812 and 814 are twisted together. As shown, pairs of contiguous loops 818—with the exception of the loop located after closed loop 6—are separated by twisted segments 820. Although not shown, it will be understood to those of skill in the art, with the benefit of this disclosure, that as many contiguous loops as are desired may be separated by a twisted segment 820 from another loop or any other number of contiguous loops to suit a particular application. For example, three contiguous loops may be separated from another loop or two or more other contiguous loops by a twisted segment in the same manner that the pairs of contiguous loops are separated by twisted segments as illustrated in FIG. 50C. Similarly, four contiguous loops may be separated from another loop or two or more other contiguous loops by a twisted segment. As yet another example, a single wire embodiment stent may have only one twisted segment separating two groups of five contiguous loops.

In contrast to the "hoop stent" disclosed in U.S. Pat. No. 5,830,229 to Konya et al. ("the hoop stent"), which is incorporated herein by reference, the single wire embodiment of the stent that has twisted segments 820, depicted in FIG. 50C for example, possesses multiple contiguous loops 818. As a result, the single wire embodiment stents with such twisted segments are more resistant to forces compressing loops 818 in a lateral manner. The directions of such lateral forces are indicated by the large arrows in FIG. 50C. As a result, if the single wire embodiment of the stent having multiple contiguous loops, such as the stent depicted in FIG. 50C, is placed in a vessel or other structure that is sometimes bent or flexed, that vessel or structure will more likely remain patent when bent or flexed than it would were it supported by the hoop stent.

Figure 16:
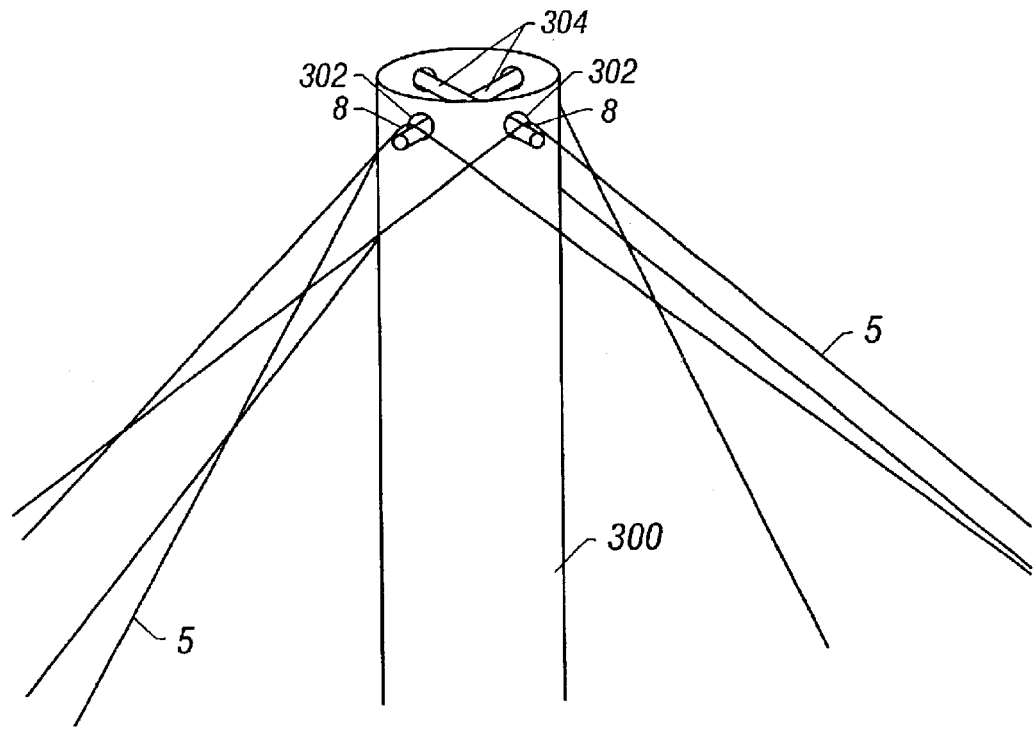
FIGS. 16–24 show stages in a hand weaving method according to one embodiment of the present invention.

Body 10 of a stent according to the present invention may be formed by various methods of plain weave including hand weaving and machine weaving. The following process is an exemplary embodiment of plain weaving according to the present invention. As shown in FIG. 16, a template 300 having a diameter corresponding to the chosen diameter of body 10 is provided. The top of the template is equipped with holes 302 around its circumference. Pins 304 are placed through the holes such that they extend beyond the outer surface of the template on opposing sides. As shown in FIG. 16, wires 5 are bent at about their midpoint around the pins. This bending may result in the formation of bend 8 as shown, or wires 5 may be wrapped around the pins to form small loops 6 (not shown). In one embodiment of body 10, angle b of small closed loop 6 or bend 8 (FIG. 1A) may be less than 90°. In a more typical embodiment of body 10, angle b may be equal to or greater than 90°, and may approach, but not include, 180°. In an even more typical embodiment, angle b may be about 140–160°. As discussed above, bends 8 and loops 6 are created in a manner that makes them likely more mechanically sound than the joints disclosed in the Wallsten patent created by connecting two wire ends together through welding or gluing.

In one embodiment of the present plain weaving process, the ends of two wires 5 may be coupled together and placed around pin 304, instead of bending a single wire 5 as above described. This coupling may be achieved by using any suitable means capable of preventing the wires from returning to their straight, unbent configuration. As shown in FIG. 30A, such means include bending and crimping a metal clip around the wires. In another embodiment of the present plain weaving process, as shown in FIG. 30B, two wires 5 may each be wrapped around pin 304 separately and secured using any suitable means, such as those just described, in further contrast to bending one wire around pin 304. After annealing (i.e., heating and cooling) wires 5 shown in FIG. 30B as described below, the two wires may be coupled to each other using any suitable means such as twisting, crimping or tying as further below described.

Although only two pins are shown in FIG. 16, it is to be understood that this is done for illustrative purposes only, and not to indicate the appropriate number of wires to use in any given application. In an exemplary embodiment, template 300 is typically formed of brass or copper, but may be formed of any suitable material capable of withstanding the cure temperature below discussed, such as stainless steel. Similarly, in an exemplary embodiment, pins 304 are typically formed of stainless steel, but may be formed of any similarly suitable material. It is to be understood that the pins may be supported by the template by any suitable means capable of withstanding the cure temperature, including preforming, attachment by welding, threading, or the like.

Figure 17:
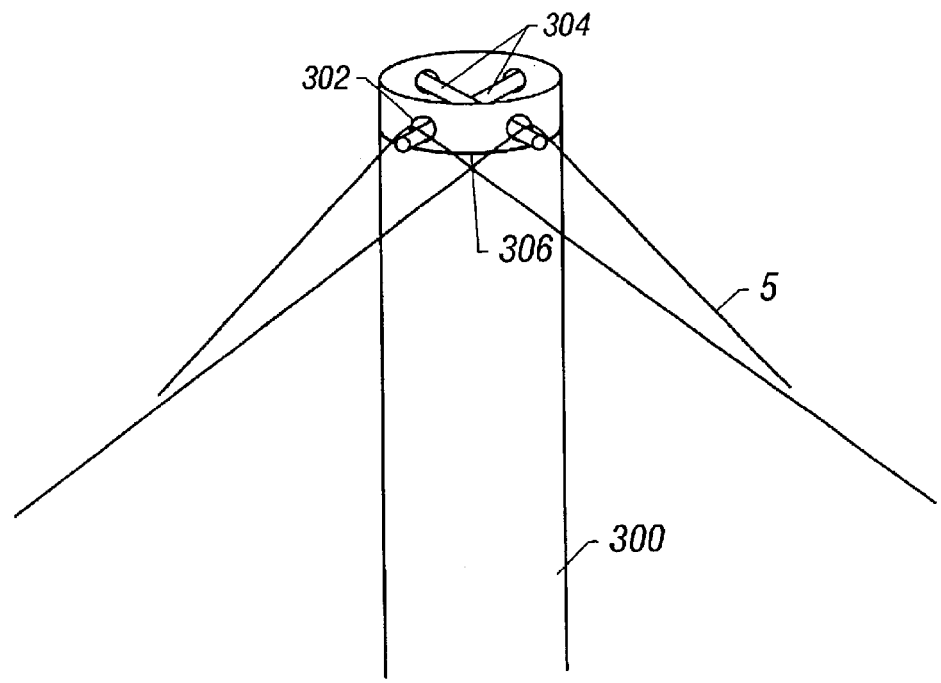

As shown in FIG. 17, after the wires have been bent around the pins, the wires are secured to the template to prevent them from returning to their original, straight, unbent position. This may be necessary given the superelastic nature of wires such as nitinol and the like (discussed below). As shown in FIG. 17, wires 5 are secured by securing wire 306 around the outside of wires 5 so as to secure wires 5 against the outside of the template. In an exemplary embodiment, copper is typically used for securing wire 306, but it is to be understood that any suitable wire capable of withstanding the annealing temperature of about 500° C. discussed below may be used. After the wires are secured, small weights 360 (shown in FIG. 20) are attached to the free ends of the wires using any suitable means such as tying, or the like. In an exemplary embodiment, weights with masses of approximately 50–100 grams may typically be used with wires having diameters of between about 0.005 inches and about 0.011 inches. However, it is to be understood that weights of different masses may be chosen so long as the wires are kept under tension (i.e. straight) during plain weaving (as described below), and properly balance the central weight (described below).

Figure 18:
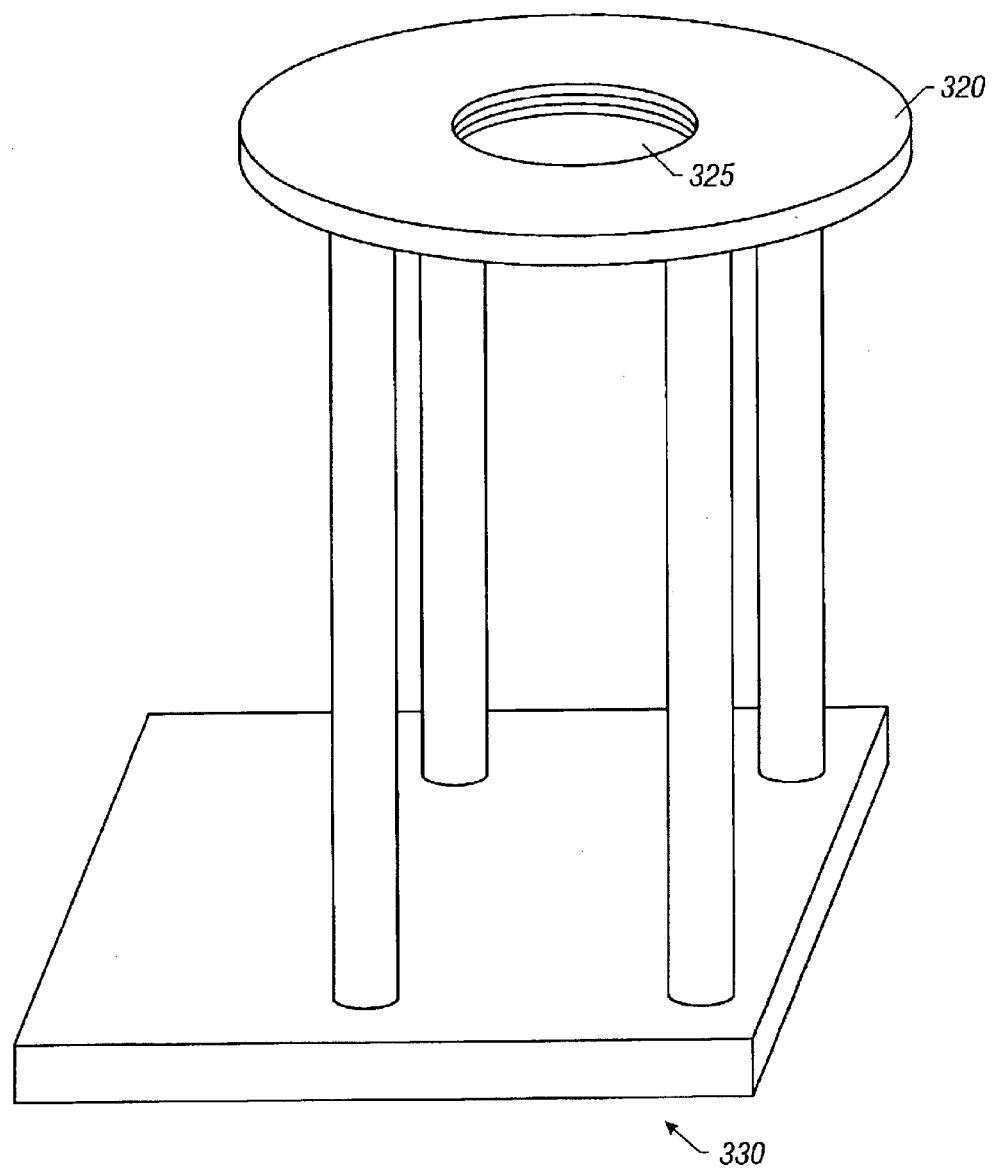

As shown in FIG. 18, a stand 330 with a circular plate 320 is provided with an opening 325. The diameter of the opening may depend on the diameter of the template. In an exemplary embodiment, an opening with a diameter of about 4.5 cm may be typically utilized in conjunction with a template of about 1.0 cm. It is to be understood, however, that an opening with a diameter more closely corresponding to the diameter of the template may be utilized.

Figure 19:
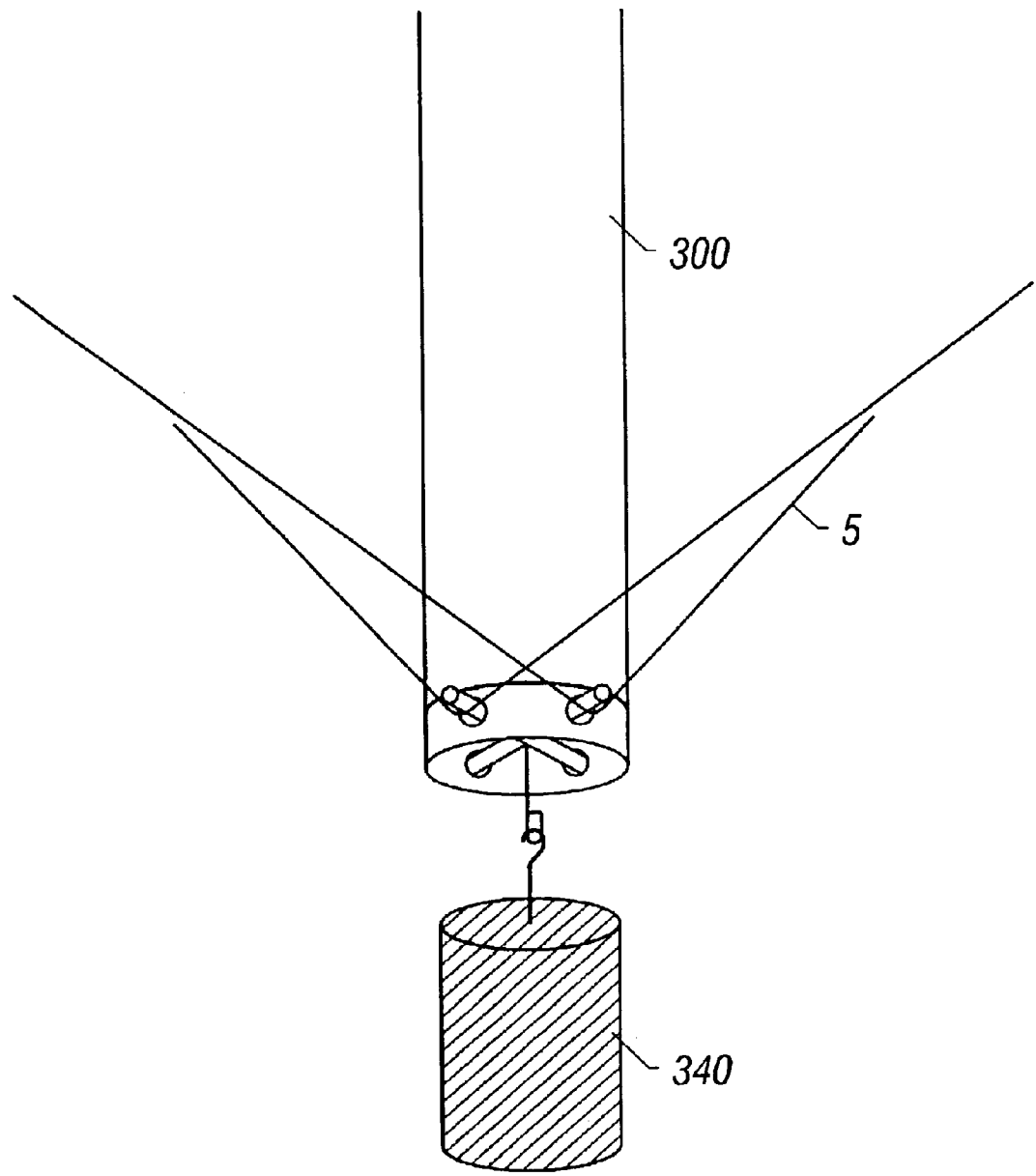

As shown in FIG. 19, before or after the weights are attached to the ends of wires 5, the template is inverted. In an exemplary embodiment, the weights may be typically attached to the free ends of the wires prior to inversion of the template such that the wires are kept under tension and may be prevented from returning to their unbent, nominal state. A central weight 340 may then be attached to the end of the template. In an exemplary embodiment, the central weight may be typically hung from the pins. However, it is to be understood that the central weight may be attached to the template's end in any suitable manner, such as hanging from holes in the template itself, etc.

Figure 20:
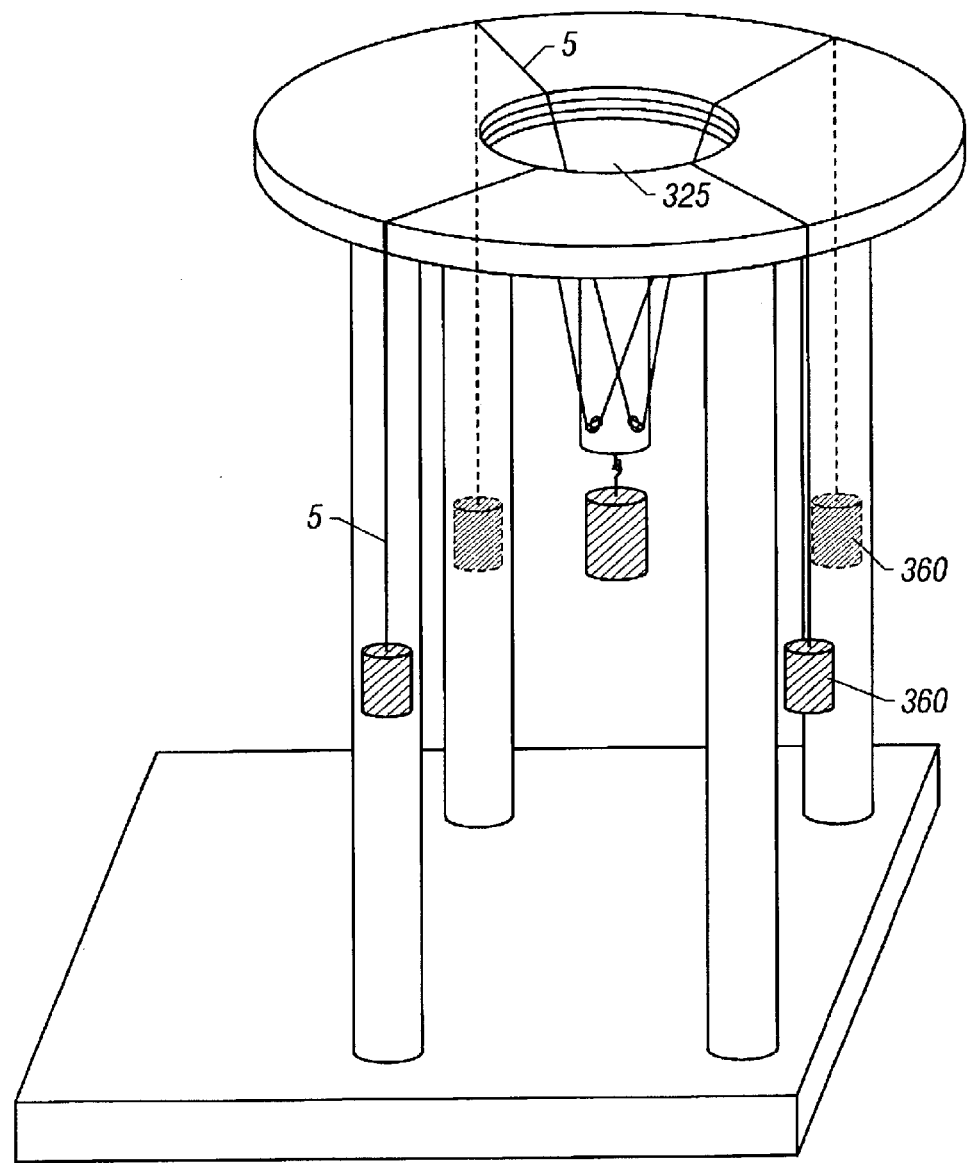
Figure 21:
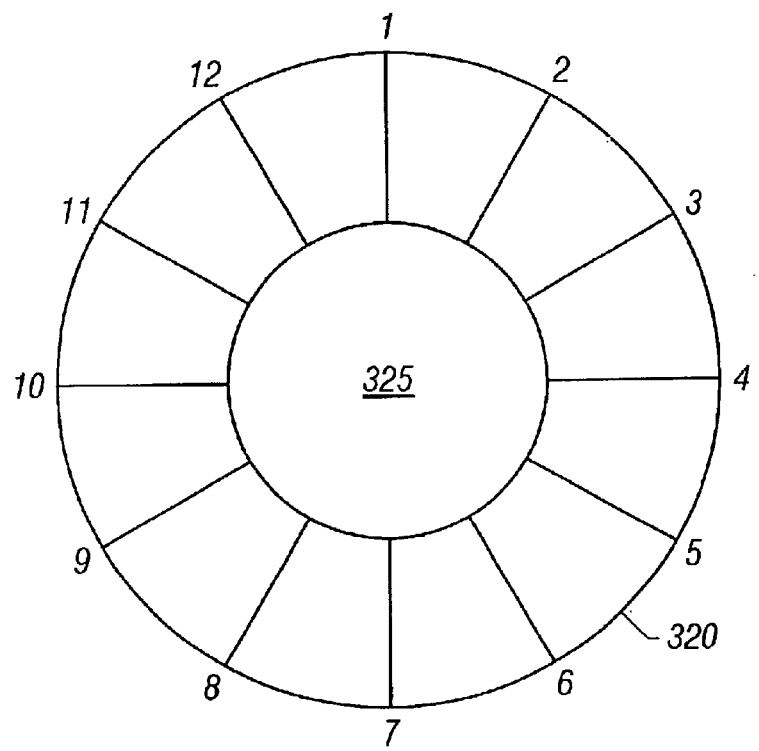

Before or after central weight 340 is attached to the end of the template, the inverted template is placed through opening 325, as shown in FIG. 20. In an exemplary embodiment, the central weight may typically be attached to the inverted template after the inverted template is placed through opening 325. As shown in FIG. 20, the wires 5 may be arranged fairly evenly around the circumference of the circular plate. As shown in FIG. 21, in an exemplary embodiment of the present invention, 6 wires having 12 ends numbered 1–12 (each wire having 2 ends) are shown as being arranged in a substantially symmetrical fashion around circular plate 320. The weights 340 and 360 typically serve to keep the wires under tension and in balance. Next, the plain weaving may take place.

Figure 22:
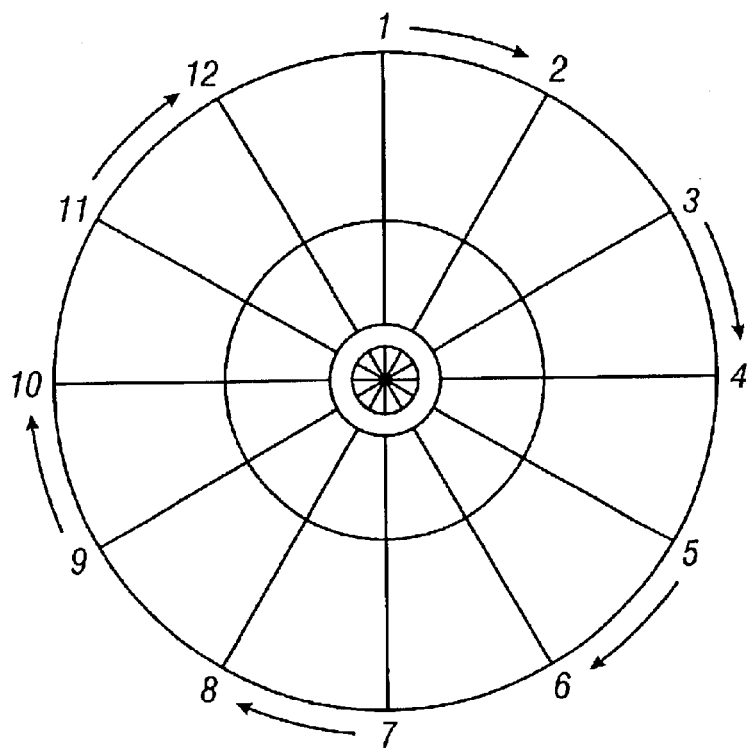
Figure 23:
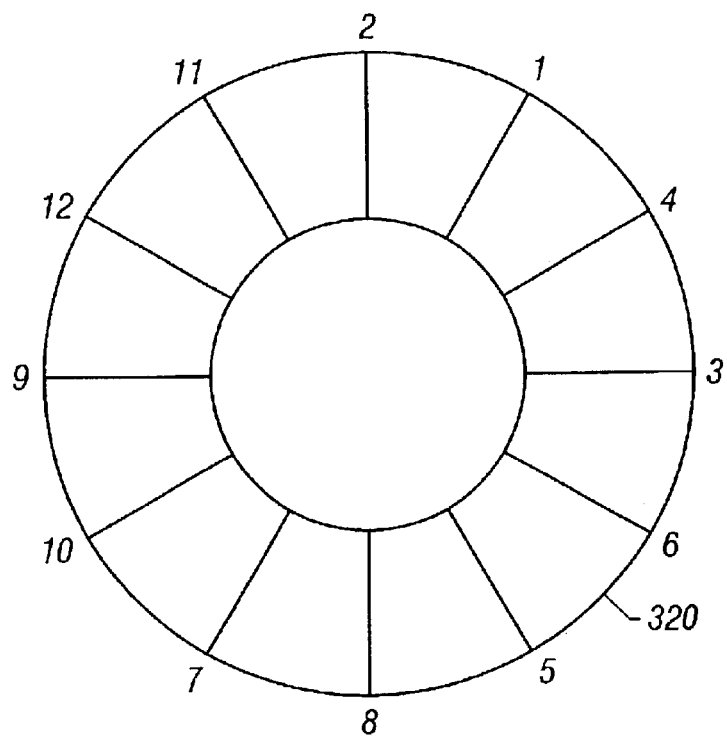
Figure 24:
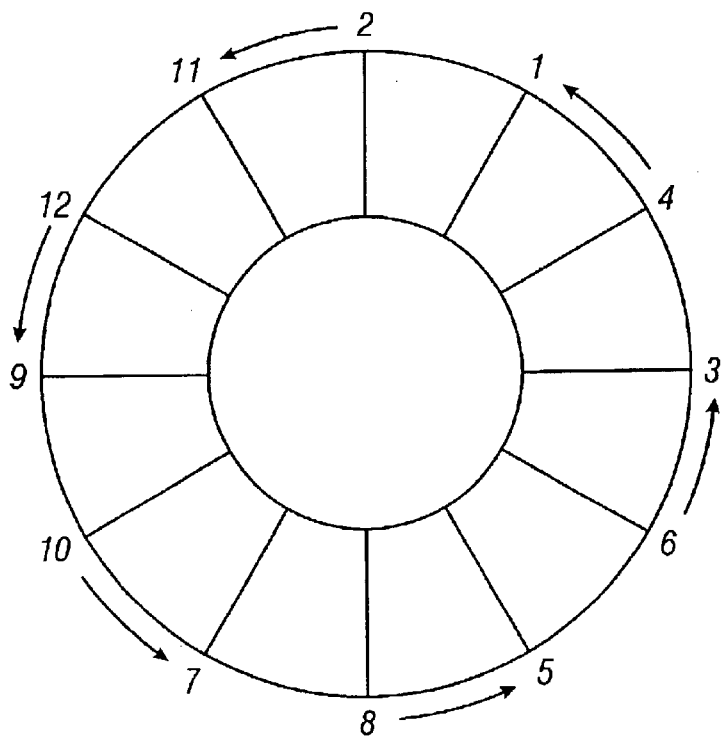

In the manner shown in FIG. 22, the weave may be started by crossing one wire end over the adjacent wire end. This crossing may be made in either a clockwise or counterclockwise fashion. This crossing may be carried out as directed by the arrows shown in FIG. 22. After a complete set of crosses (or one "turn") has been carried out, the location of the crossed wire ends is as shown in FIG. 23. In an exemplary embodiment, the resulting location of the wire ends may be achieved by crossing one wire end over another in one direction while slightly shifting the wire end not crossed in the opposite direction. In an exemplary embodiment, this shifting may be about 15°. Thus, wire end 1 may be crossed in a clockwise direction over wire end 2, while shifting wire end 2 about 15° counterclockwise. Once one turn has taken place, crossing may begin in the same fashion, but in the opposite direction, as shown in FIG. 24. This process may be repeated until the plain weave is complete.

The tightness of the plain weave (i.e., the angle a between the wires—FIG. 1A) may be adjusted by changing the central weight. An increase in the central weight results in a looser weave (decreased angle a between the wires) and vice versa. Upon completion of the plain weave, the adjacent wire ends may be closed as below described.

In an exemplary embodiment according to the present invention, a conventional braiding machine may be utilized to arrange wires 5 in a plain weave to form body 10 of a stent or any other device described herein. Such a braiding machine may be obtained, for example, from Wardwell Braiding Machine Company in Central Falls, R.I. The manner in which a plain weave may be achieved using a conventional braiding machine is displayed in FIG. 7 of U.S. Pat. No. 5,419,231 to Earle, III et al. (1995), which is hereby expressly incorporated by reference, as well as in FIG. 1 of U.S. Pat. No. 5,485,774 to Osborne (1996), which is hereby expressly incorporated by reference.

After the plain weave process is complete, as shown in FIG. 1A, at the rear or proximal end 2 (the end closest to the surgeon/operator) of body 10, wire ends 7 may be twisted together using multiple twists so as to form closed structures 4. In an exemplary embodiment, as few as 2 twists may be used, and as many as about 6. In an exemplary embodiment, it is preferable to keep the twisted wire ends as short as possible. The shorter the twisted wire ends are kept, the more resistant to bending the twisted wire ends are. As a result, the twisted wire ends are less likely to be inadvertently displaced during placement, repositioning, or retrieval, thus reducing the potential for causing tissue damage. Although not shown, it will be understood to those of ordinary skill in the art with the benefit of the present disclosure that the wire ends may be coupled together, instead of by twisting, using any suitable means capable of withstanding the heating described below, such as bending and crimping a metal clip around the wires, tying them together with suitable material such as stainless steel wire, welding, etc.

Figure 48:
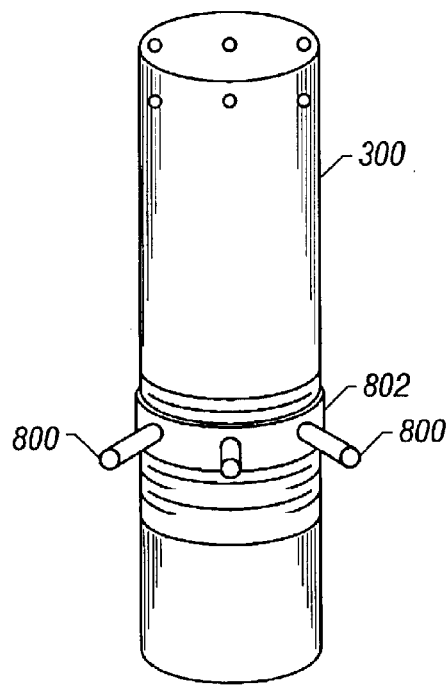
FIG. 48 is a perspective view of a template around which a ring having finish pins has been threadably engaged according to one embodiment of the present invention.
Figure 49:
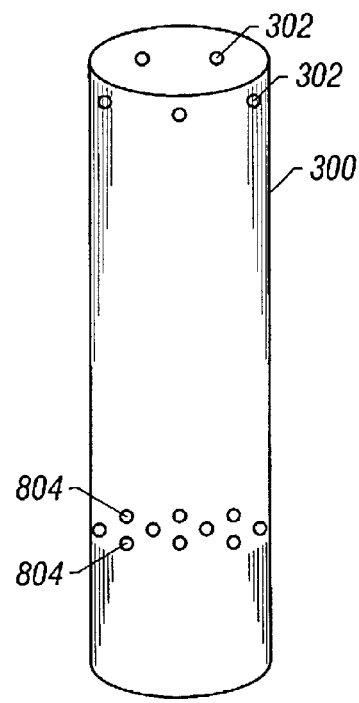
FIG. 49 is a perspective view of a template having finish holes through which finish pins may be placed according to one embodiment of the present invention.

Other configurations of template 300 may also be utilized consistently with the present disclosure. For example, template 300 may be provided not only with pins 304 or tabs 600 (described below), around which wires 5 are bent, wrapped, tied, twisted, etc., prior to weaving the body of the stent (or the bodies of any of the woven structures disclosed herein), but may also be provided with pins around which the wire ends may be twisted in fashioning closed structures 4. Finish pins 800 may be supplied on a ring, such as ring 802 depicted in FIG. 48, in any suitable fashion, including, for example, through removable or permanent attachment. Ring 802 may be configured to threadably engage template 300 as depicted in FIG. 48. In other embodiments, ring 802 may be configured to engage template 300 by virtue of frictional forces (not shown) or may be configured to be secured to template 300 as would a clamp (not shown). Finish pins 800 may also be engaged with template 300 in the same manner as pins 304. As shown in FIG. 49, in such an embodiment, template 300 may be provided with finish holes 804 similar to holes 302, and finish pins 800 may be placed through finish holes 804. Ring 802 may also be utilized in place of holes 302 and pins 304.

In an embodiment in which finish pins 800 are engaged with template 300 through the utilization of ring 802, the number of finish pins utilized may be equal to the number of wires 5 that are used. Template 300 may be threaded along any portion of its length so as to best accommodate a variety of woven body sizes. For example, only a portion of template 300 may be threaded, as depicted in FIG. 49. Threads need not be utilized with a ring that engages template 300 by virtue of frictional forces.

Advantageously, the use of ring 802 allows for the easy and precise alignment of pins 304 or tabs 600 with finish pins 800. Another advantage afforded by the use of ring 802 is the ease with which the precise length of the woven body may be achieved. The length of the woven body may be achieved by adjusting and fixing the distance along the length of template 300 between pins 304 or tabs 600 and finish pins 800. In an embodiment in which finish pins 800 are placed through finish holes 804, the number of finish pins utilized may be equal to one-half of the number of wires 5 that are used, since both ends of the finish pins will be utilized. Template 300 may be provided with finish holes 804 along any portion of its length so as to best accommodate a variety of woven body sizes. For example, only a portion of template 300 may be provided with finish holes 804, as depicted in FIG. 49.

As with ring 802, the use of finish holes 804 advantageously allows for the easy and precise alignment of pins 304 or tabs 600 with finish pins 800. Additionally, the precise length of the woven body may advantageously be achieved by virtue of the distance along the length of template 300 between pins 304 or tabs 600 and finish holes 804 (and, therefore, finish pins 800.)

With finish pins 800 in place, once the wire ends of wire(s) 5 have been woven around template 300, the wire ends may be secured around finish pins 800 in any suitable manner to form closed structures 4, including by twisting, bending, wrapping and the like. In one embodiment, the wire ends may be crossed, then bent around finish pins 800 and then secured together using a short piece of a thin-walled metal tubing. Such a joint may then be reinforced by soldering, welding, or the like. A suitable number of additional twists may be utilized after securing the wire ends around finish pins 800 in forming closed structures 4. Securing wire 306 (not shown) may be utilized to secure closed structures 4 to template 300 during annealing.

As a result of securing the wire ends around finish pins 800, the angle created between the crossed wire ends may be similar, if not identical to, angle b described above. Advantageously, by using finish pins 800, this angle between the crossed wire ends may be maintained, preventing the weave of the woven body from loosening. Were loosening to occur, the expansile or radial force of the portion of the body with the loosened weave could decrease, causing that portion of the woven body to remain elongated within the structure in which it is placed. Therefore, through the use of finish pins 800 and as a result of the correlating maintenance of the angle between the crossed wire ends that are wrapped or twisted around the finish pins, the tightness of the weave along the length of the woven body—from end to end—may be consistent and resistant to loosening, and the expansile force of the end of the woven body having closed structures 4 may be comparable to the expansile force of the other portions of the woven body.

Figure 37:
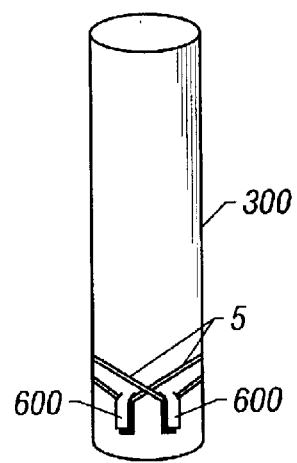
FIG. 37 is perspective view of a template with longitudinal tabs around which wires are bent according to one embodiment of the present invention.

Another method of creating body 10 of a stent according to the present invention is illustrated in FIGS. 37–47B. As shown in FIG. 37, the base of template 300 may be equipped with longitudinal tabs 600 formed by two longitudinal cuts connected by a transverse cut. The length of the cuts may be determined based upon the size of the template chosen. For example, a template that is about 10 mm in diameter may have longitudinal tabs with longitudinal cuts about 4 to 5 mm long, and the connecting transverse cuts may be about 2 mm long. As illustrated in FIG. 37, tabs 600 may be slightly elevated from the surface of template 300 and may be positioned equally around template 300.

Figure 38A:
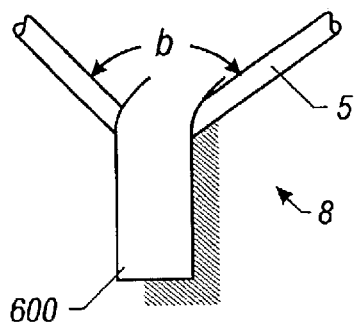
FIG. 38A is an enlarged perspective view of the longitudinal tab and bent wire depicted in FIG. 37 according to one embodiment of the present invention.
Figure 38B:
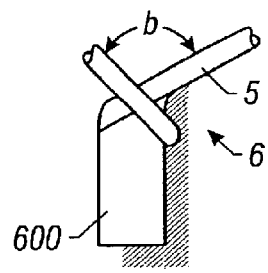
FIG. 38B is an enlarged perspective view of a longitudinal tab depicted in FIG. 37 around which a wire is bent to form a loop according to one embodiment of the present invention.

FIGS. 37 and 38A and B also illustrate that wires 5 may be bent around tabs 600 at selected points located between the ends of the wires to form bent portions along wires 5. The bent portions may take the form of bends 8, as shown in FIG. 38A, or may be further wrapped around tabs 600 to form loops 6, as shown in FIG. 38B. Angle b of bends 8 or loops 6 may be less than 90°. In a more typical embodiment of body 10, angle b may be equal to or greater than 90°, and may approach but not include, 180°. The bent portions may be arranged to define end 12 of body 10. Wire ends 7 of wires 5 may then be weaved to create body 10 using, for example, the following machine weave method.

Figure 39:
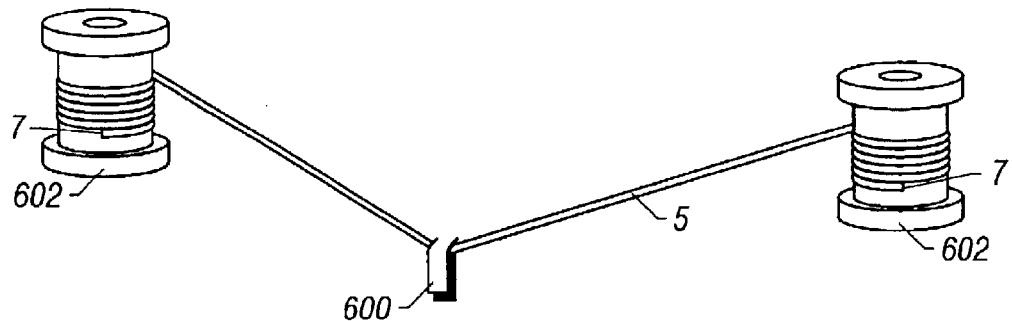
FIG. 39 is a perspective view of a wire bent around a longitudinal tab and wrapped around a pair of bobbins according to one embodiment of the present invention.

As shown in FIG. 39, ends 7 of each wire 5 may be arranged around a pair of bobbins 602. The length of the wire wound around each bobbin may be determined by considering the total length of the wire needed to form body 10 as well as the wire length needed to arrange the bobbins around weaving plates (shown in FIG. 40), which are discussed below in greater detail.

Figure 40:
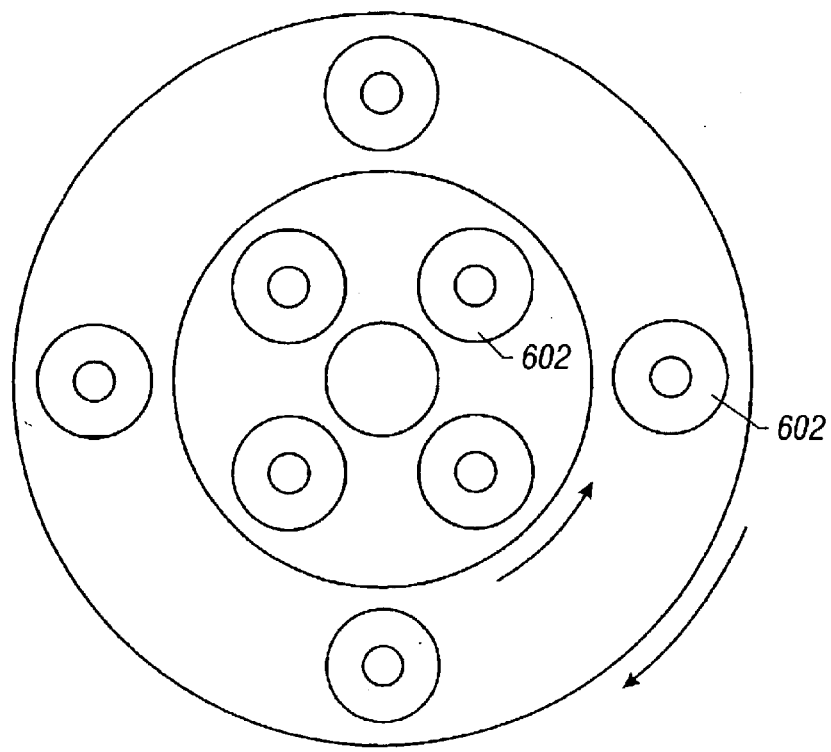
FIG. 40 is a top view of inner and outer weaving plates provided with bobbins according to one embodiment of the present invention.
Figure 41:
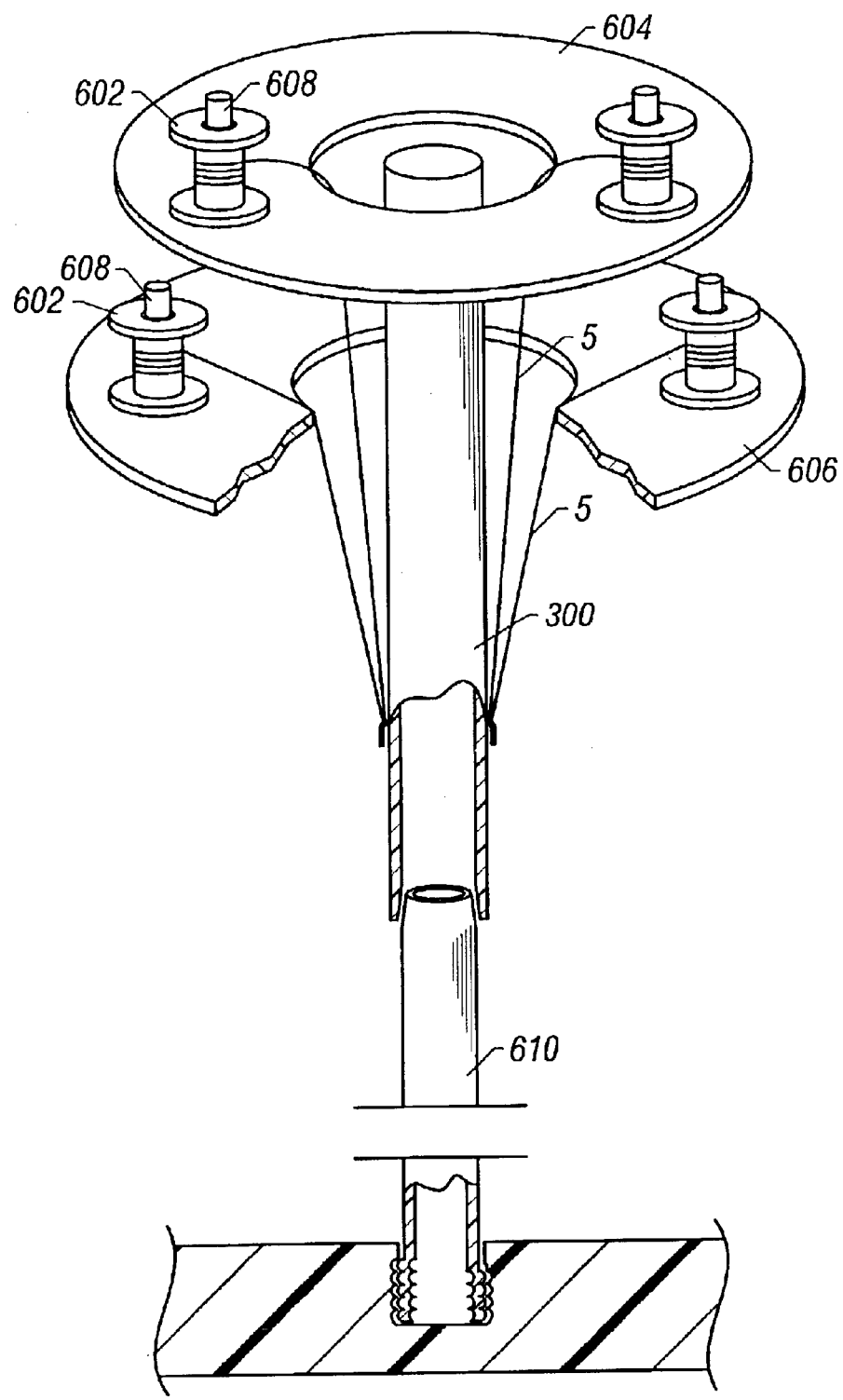
FIG. 41 is a perspective view depicting an upper weaving plate provided with bobbins and wires, a partial cross-sectional view of a lower weaving plate provided with bobbins and wires, and a partial cross-sectional view of a template around which both plates are arranged according to one embodiment of the present invention.

As shown in FIG. 40, in one embodiment in which bobbins 602 are utilized, two coaxially arranged weaving plates may be utilized. As shown in FIG. 41, upper weaving plate 604 and lower weaving plate 606 may be positioned in different horizontal planes. FIG. 41 illustrates that the weaving plates may be equipped with multiple bobbin rods 608, the axes of which are substantially perpendicular to the weaving plates, on which bobbins 602 may be slidably secured. (FIG. 41 depicts only 4 bobbins for the sake of simplicity.) The weaving plates may be provided with holes therein through which template 300 and/or wires 5 may pass, as shown in FIG. 41. Template 300 may be secured to the base of the weaving machine chosen using any suitable means such as template rod 610, around which template 300 may pass, as shown in FIG. 41. Template 300 may be secured to the base of the weaving machine chosen using any suitable means such as template rod 610, around which template 300 may be slidably placed (FIG. 35). Template rod 610 may be configured to firmly engage template 300 through frictional forces (e.g., by tapering template rod 610). Instead of template rod 610, any appropriate lock mechanism may be used to secure the base of the weaving machine to template 300.

Figure 42A:
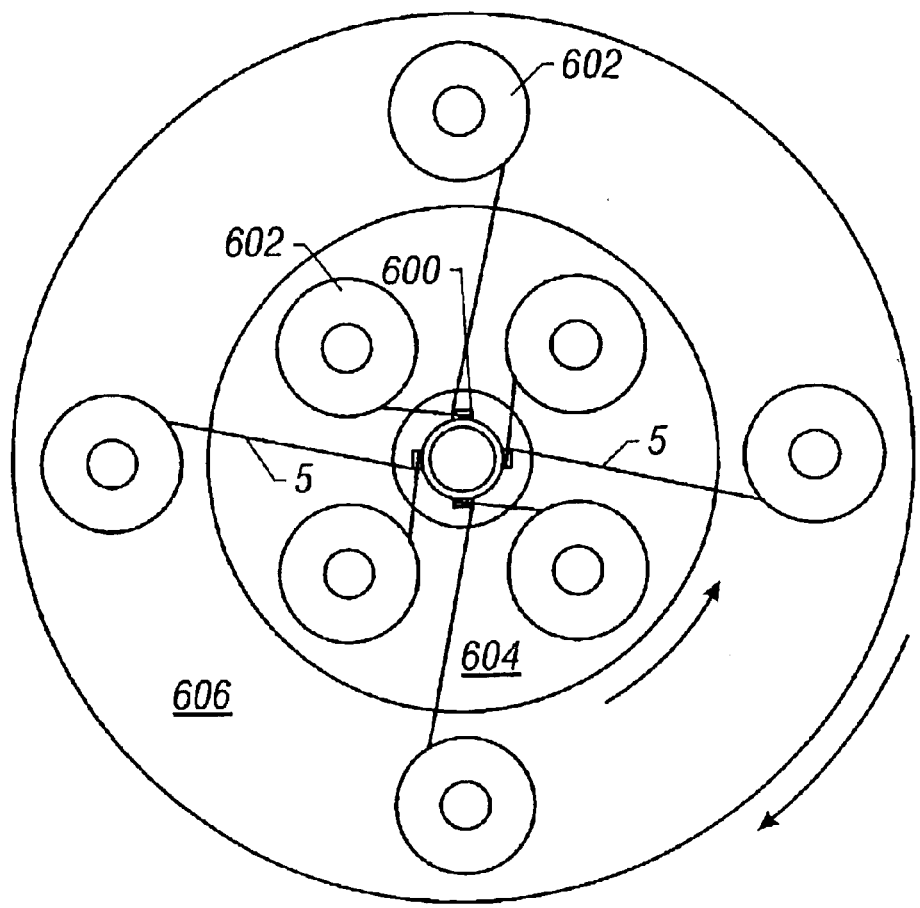
FIG. 42A is a top view of upper and lower weaving plates provided with bobbins and wires and arranged around a template, and illustrates the first crossing of the wires according to one embodiment of the present invention.
Figure 42B:
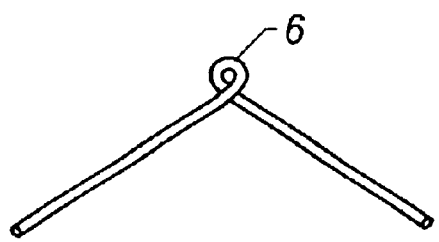
FIG. 42B is a front view of a small caliber loop formed by bending a wire according to one embodiment of the present invention.
Figure 43A:
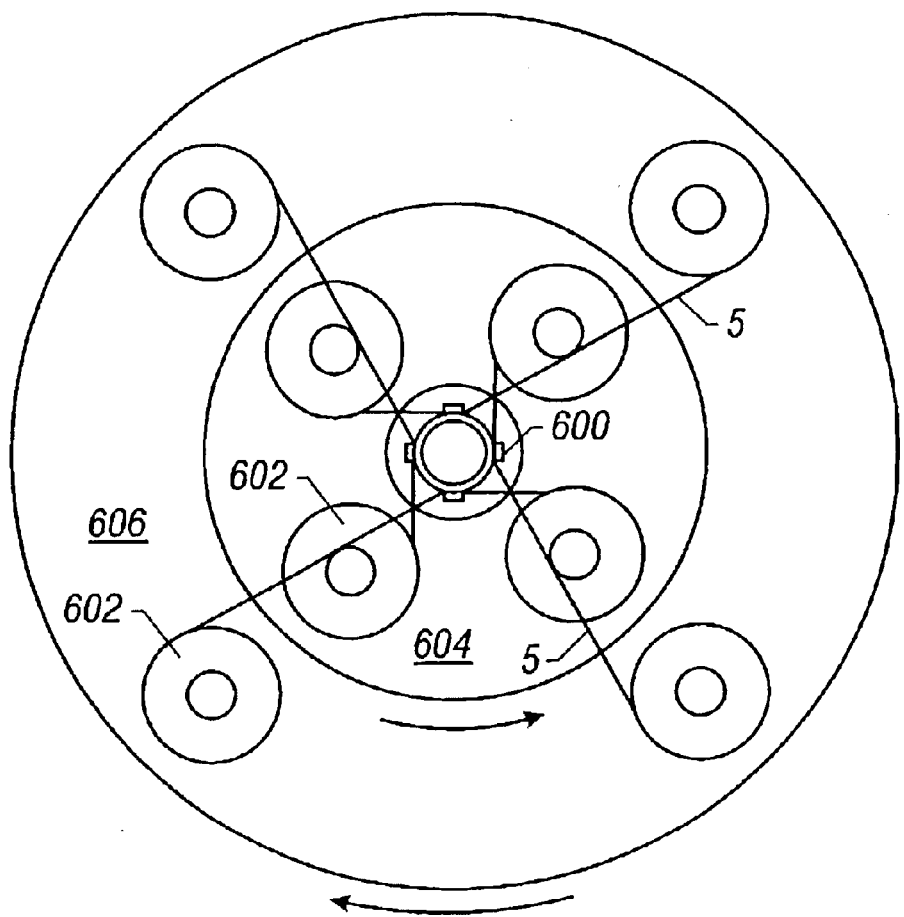
FIG. 43A is a top view of upper and lower weaving plates provided with bobbins and wires and arranged around a template, and illustrates the first crossing of the wires according to another embodiment of the present invention.

As shown in FIGS. 42A and 43A, the pairs of bobbins 602 may be prepared for weaving by arranging one bobbin on upper weaving plate 604 and the other bobbin from the pair on lower weaving plate 606. Wires 5 may then be bent around tabs 600, and the ends of the wires may be attached to bobbins 602 using any suitable means capable of holding wires 5 under tension throughout the weaving process. An example of such a mechanism is a one-way brake that allows bobbin 602 to rotate in a single direction only, such that the wire 5 may wind off bobbin 602. Simultaneously, such a brake may be configured so as to continuously maintain tension in wire 5 by virtue of the brake's resistance to the winding off of wire 5.

Figure 43B:
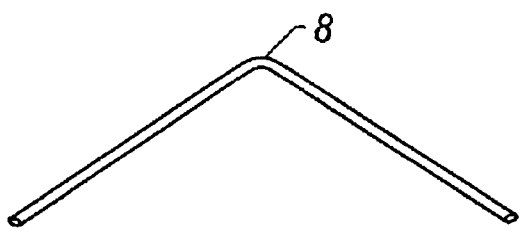
FIG. 43B is a front view of a bend formed by bending a wire according to one embodiment of the present invention.

As shown in FIG. 42A, with the wire ends in place, the weaving may begin by crossing the wire ends of the same wire, which results in the formation of a small caliber loop 6 (FIG. 42B) at the site of the bent portion. In another manner of weaving illustrated in FIG. 43, the wire ends of different wires may be crossed first, resulting in bend 8 at the site of the bent portion (FIG. 43B).

Figure 44:
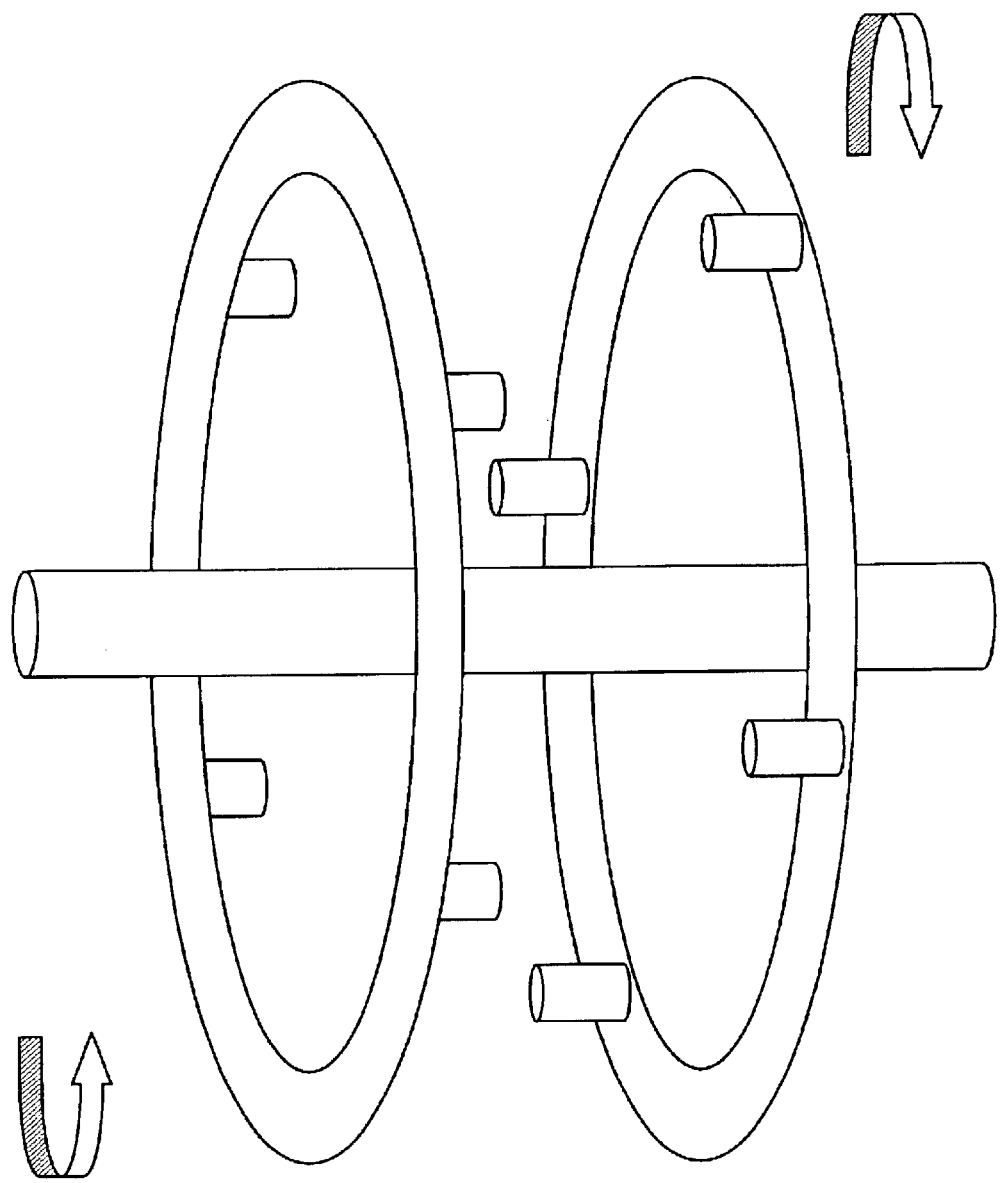
FIG. 44 is a perspective view of upper and lower weaving plates provided with bobbins and arranged around a template such that the surfaces of the weaving plates from which the bobbin rods extend face each other according to one embodiment of the present invention.
Figure 46A:
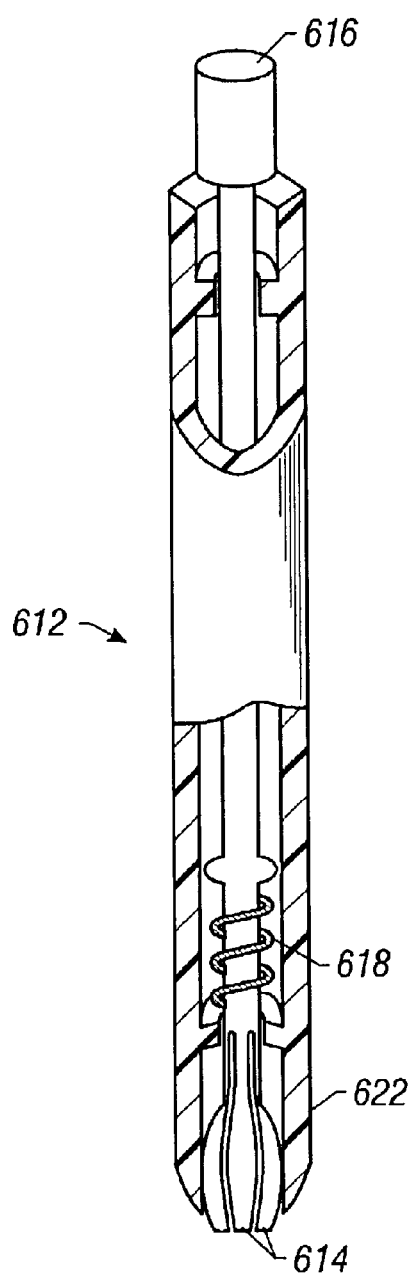
FIG. 46A is a perspective, partial cross-sectional view of a tool for twisting the wire ends of a woven body according to one embodiment of the present invention.
Figure 46B:
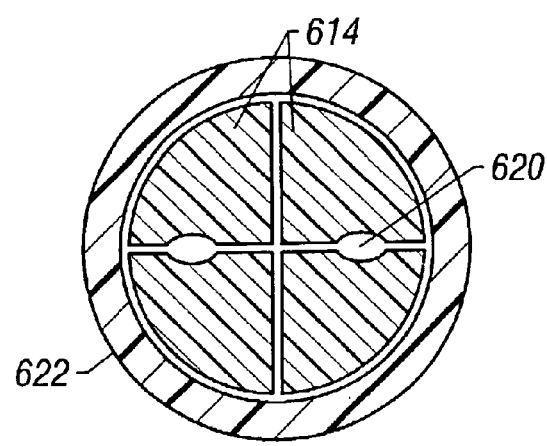
FIG. 46B is a cross-sectional view of the jaws and outer housing of the tool illustrated in FIG. 46A.

As shown in FIGS. 44–45, the two weaving plates may be arranged such that the surfaces thereof from which the bobbin rods extend face each other. In this alternative embodiment, the diameters of the plates may be the same or different. Wires 5 may be arranged on bobbins 602 in the same manner as described above, as shown in FIG. 45.

Despite which of the aforementioned weaving-plate arrangements is utilized, the weaving plates rotate in opposite directions during the weaving process. The weaving plates may be operated at any suitable speed. In this regard, a speed as low as 1 to 10 cycles per minute is acceptable. The weaving plates may also be driven by hand.

Figure 61:
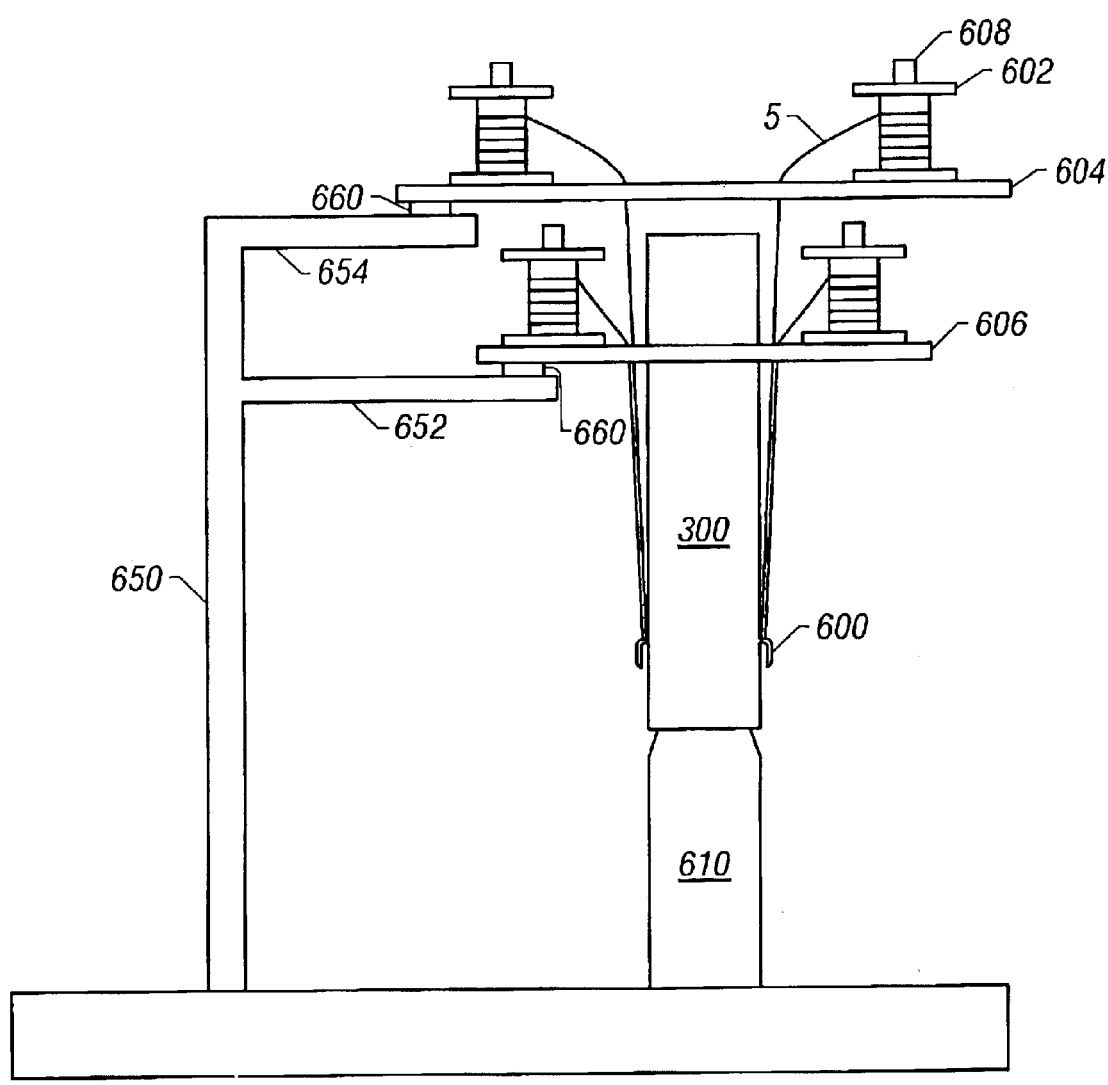
FIG. 61 is a front view of upper and lower weaving plates supported by a weaving plate supporter according to one embodiment of the present invention.

The weaving plates may supported and rotated using any suitable means. FIG. 61 illustrates one means of supporting and rotating weaving plates 604 and 606. (FIG. 61 depicts on 4 bobbins for the sake of simplicity.) As shown, weaving plate supporter 650 may be equipped with lower arm 652 and upper arm 654 for supporting lower and upper weaving plates 606 and 604, respectively. Weaving plate drivers 660 may be secured to the upper and lower arms of the weaving plate supporter and engaged with the weaving plates in order to operate them. The drivers may be configured to operate in any suitable fashion. For example, the drivers may be configured with a power source and provided with gears of any suitable configuration for causing the weaving plates to rotate. The drivers may also be configured to utilize magnetism or electromagnetism to rotate the weaving plates. The drivers may be also be configured such that the weaving plates may be rotated by hand. Further, although not shown, it will be understood to those of skill in the art, with the benefit of this disclosure, that either or both of the upper and lower arms may be provided with branches to which drivers may be attached. The drivers on the branches could then be secured to or engaged with the top surfaces of the weaving plates in the same fashion that drivers 660 are engaged with the bottom surfaces of the weaving plates as shown in FIG. 61. Thus, in such an embodiment, both the top and bottom surfaces of each weaving plate would be engaged with drivers.

A braiding machine suitable for carrying the weaving process just described (i.e., utilizing the weaving plates) may be obtained, for example, from Wardwell Braiding Machine Company in Central Falls, R.I.

Figure 47A:
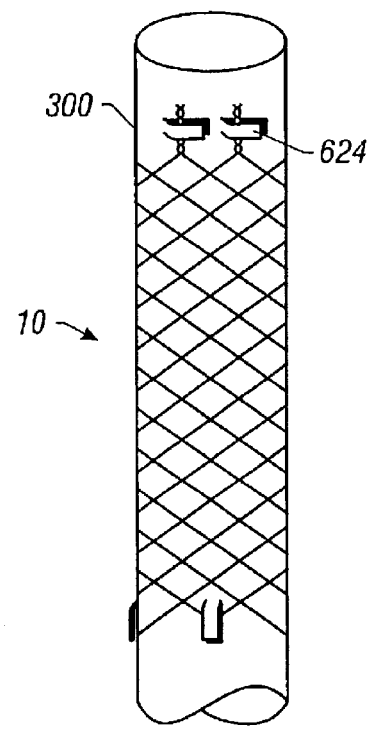
FIG. 47A is a perspective view of a body woven around a template having longitudinal and transverse tabs according to one embodiment of the present invention.
Figure 47B:
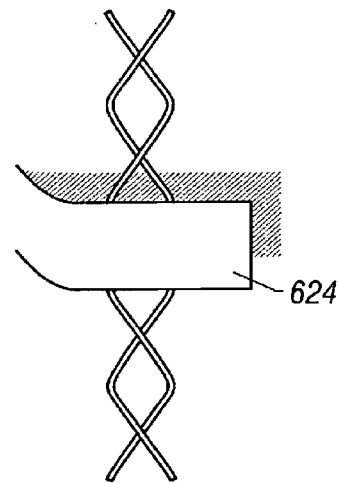
FIG. 47B is an enlarged perspective view of one of the transverse tabs and twisted wire ends depicted in FIG. 47A according to one embodiment of the present invention.

After the weaving process is complete, wire ends 7 may be twisted together or coupled as described above to form closed structures 4. To make the process of wire twisting faster and easier, the wires may be twisted with a special hand tool designed for this purpose. Tool 612 illustrated in FIG. 46A follows the principle of an automatic pencil. Jaws 614 of tool 612 are configured so that wire ends 7 may be firmly held between jaws 614. Jaws 614 may be activated by push button 616 moving against spring 618. After placing wire ends 7 into pre-formed gaps 620 located between jaws 614 (FIG. 46B), spring 618 expands (or returns to its unconstrained state) and retracts jaws 614, securing wire ends 7 firmly between jaws 614 due to the pressure of outer housing 622 acting to close jaws 614. Outer housing 622 may then be rotated to create multiple twists of wire ends 7. As illustrated in FIGS. 47A and 47B, the twisted ends of body 10 may be secured to template 300 using transverse tabs 624, which may be formed the same way as longitudinal tabs 600.

Turning to the single wire embodiment, body 10 may be formed using either the hand weaving process or the machine weaving process, both of which are described above. In preparation for the weaving process, template 300, which may be configured to have any suitable shape, may be provided with pin 304 or longitudinal tab 600 near the end thereof at which the weaving is to begin. Near its other end, template 300 may be provided with finish pin 800 or transverse tab 624, which may be appropriately aligned with pin 304 or longitudinal tab 600. In one embodiment, finish pin 800 may be provided on ring 802.

The weave of body 10 may then be started by bending wire 5 around pin 304 or longitudinal tab 600 to form either bend 8 or closed loop 6. In an exemplary embodiment, securing wire 306 may be utilized to secure bent wire 5 to template 300 as described above. The two segments of wire 5 on either side of bend 8 or closed loop 6 may then be woven to create body 10 by helically wrapping the segments around template 300 in opposite directions toward finish pin 800 or transverse tab 624. The segments may be crossed over each other during the process in alternating fashion to result in the single wire embodiment depicted in FIG. 50B. This weaving may take place either by hand or using the weaving templates described above.

After the weaving is complete, in one embodiment, closed structure 4 may be created by wrapping the wire ends around finish pin 800 in the manner described above. In another embodiment, the wire ends may be twisted or coupled together as described above to form closed structure 4, which may then be secured to transverse tab 624. It will be understood that additional pins 304 or longitudinal tabs 600 may be utilized to create the single wire embodiment. Such additional pin(s) or tab(s) may be vertically aligned with the other pin or longitudinal tab such that multiple closed loops 6 may be formed at the end of body 10 where the weave begins, as depicted in FIG. 50B. Similarly, additional finish pins or transverse tabs may be utilized in the same fashion. The use of pin(s) 304 or longitudinal tab(s) 600 with finish pin 800 or transverse tab 624 will advantageously ensure that wire 5 remains in position during annealing. The annealing processes described below may be utilized for annealing the single wire embodiment.

After the plain weave of wires 5 is completed on the template, if the wires are made of a material that can be programmed with either thermal shape memory or superelasticity such as nitinol or other shape memory materials described below, body 10/template unit may be heated so as to program body 10 with either thermal shape memory or superelasticity. If body 10 is programmed with superelasticity, its initial shape can be deformed by applying a force thereto. After removal of the force, body 10 may substantially recover its initial shape. If body 10 is programmed with thermal shape memory, its initial shape can be deformed upon application of a force at a first temperature. The force may be removed, and body 10 may remain deformed until heated to a second temperature. At the second temperature, body 10 may substantially recover its initial shape.

In programming body 10 with superelasticity, the body 10/template unit may be heated to about 500° C. for about 5 to 15 minutes, typically about 12 to 15 minutes, and even more typically for about 15 minutes, in an oven. After allowing the unit to cool to room temperature, wires 5 possess superelastic properties. In an exemplary embodiment, natural cooling is typically used. It is to be understood, however, that accelerated cooling using a fluid bath, for example, may be utilized resulting in slightly different superelastic characteristics than are achieved with natural cooling. In programming body 10 with thermal shape memory, the body 10/template unit may be heated to about 500° C. for about 60 to 120 minutes, typically about 120 minutes, in an oven. After allowing the unit to cool to room temperature, wires 5 possess thermal shape memory. In an exemplary embodiment, natural cooling is typically used. It is to be understood, however, that accelerated cooling using a fluid bath, for example, may be utilized resulting in slightly different thermal shape memory characteristics than are achieved with natural cooling.

In an exemplary embodiment of body 10, it is preferable to further reinforce the coupled wire ends of closed structures 4 after body 10 has been properly annealed (especially if twisting was utilized). This reinforcement may be accomplished by any suitable means such as point welding, soldering, pressure welding, or the like. The wire ends of closed structures 4 may be soldered by removing any oxide layer that may have formed over the relevant portions of the wires used, and applying solder to those portions. Soldering may be enhanced by first wrapping the coupled wire ends of the closed structures 4 with thin stainless steel wires. In an exemplary embodiment, point welding is preferred to soldering, because point welding is easier to perform than soldering, and may be more suitable with regard to long-term implantation of the stent.

The wires of body 10 may be constructed of any material compatible with the tissue in which the stent will be placed. Further, the material may be suitably rigid and elastic and capable of being programmed with either superelasticity or thermal shape memory. The materials may, for example, be NiTi alloys like nitinol. Such alloys can be heated and allowed to cool to room temperature, resulting in the alloys having either superelastic or thermal shape memory properties, depending on the heating time as above described. Other alloys that may be used include FePt, FePd, and FeNiCoTi. These alloys may be heat treated to exhibit thermoelastic martensitic transformation, and, therefore, good thermal shape memory. Other alloys such as FeNiC, FeMnSi, and FeMnSiCrNi do not possess long-range order and undergo non-thermoelastic transformation, and, thus, may also be used. Additionally, some $\beta$-Ti alloys and iron-based alloys may also be used.

In an exemplary embodiment, nitinol possessing about 55 to 56% Nickel, and 45 to 44% Titanium, may be used for wires 5 of body 10. Such nitinol wires are commercially available from Shape Memory Applications in Santa Clara, Calif.

When using nitinol wire, the radiopacity of body 10 advantageously increases over the radiopacity of stents formed using materials such as stainless steel. The radiopacity depends primarily on the diameter of the nitinol wires and the tightness of the plain weave created by the wires. The radiopacity of body 10 can be increased further by using silver solder to reinforce the coupled wire ends forming closed structures 4.

The wire sizes that may be used for the stents of the present invention vary depending on the application of the stent. In an exemplary embodiment, small stents ranging from about 2 to about 4 mm in diameter and about 1 to about 2.5 cm in length, typically for coronary application, may utilize wires from about 0.003 to about 0.006 inches in diameter. In an exemplary embodiment, medium stents ranging from about 4.5 to about 10 mm in diameter and about 2 to about 10 cm in length, such as are used in the iliac artery, femoro-popliteal artery, carotid artery, and the renal artery, may utilize wires from about 0.006 to about 0.009 inches in diameter. In an exemplary embodiment, large stents above about 10 mm in diameter may utilize wires from about 0.006 to about 0.012 inches in diameter. Applications for the large stents include the aorta (typically a vessel diameter in about the 20 to 40 mm range), the inferior vena cava ("IVC"), which is usually less than about 28 mm in diameter, the superior vena cava ("SVC"), the esophageal (20–25 mm in diameter), and the colon, which may be about 15 to about 25 mm.

Tapered Stents

Figure 14:
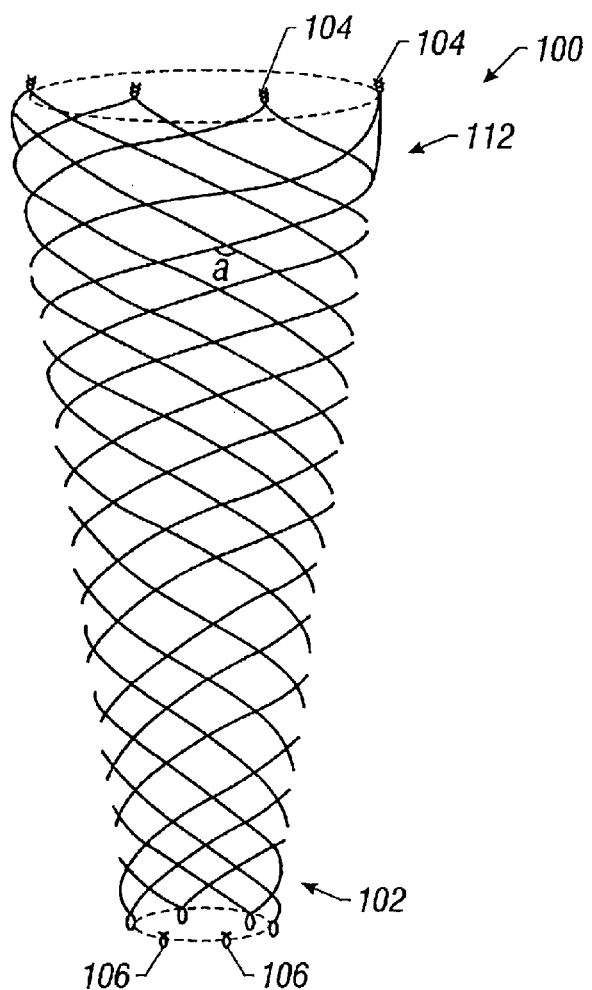
FIG. 14 is a is a perspective view of a tapered stent according to one embodiment of the present invention.

With reference to the illustrative embodiment shown in FIG. 14, there is shown a tapered stent for insertion and delivery into an anatomical structure. Tapered body 100 may be formed using plain weave by the methods above described. Potential embodiments of tapered body 100 include the single wire embodiment. The types of applications for which a tapered stent may be used include the ilio-femoral, femoro-popliteal arteries, as well as in the carotid arteries for stenting long lesions.

The tapered configuration may be achieved different ways. In a first method using the hand weave method or any of the machine methods described above, a template may be chosen possessing an appropriate taper. In an exemplary embodiment, a template with a smooth, contiguously decreasing diameter without steps is typically used. The shape of the template may correspond roughly to the inner shape of the tapered stent. The shape of the tapered stent may be chosen based on the shape of the vessel or structure into which it will be placed.

In an exemplary embodiment, it may be preferable to choose a shape for the tapered stent (and, thus, for the template) such that a "wedge-effect" will be achieved between the tapered stent and the vessel or structure into which it is placed. The wedge-effect may be used to fix the stent in position and prevent it from distal migration. It is to be understood, however, that any suitable means for improving the fixation of the stent in the vessel or structure, such as flaring the proximal end of the stent, may be used in addition to or instead of the wedge-effect.

Using such a template and either hand or machine weave, the weave may be substantially uniform along the axial length of the stent. As a result of the substantially uniform weave, the expansile force of the stent may be substantially uniform along the axial length of the stent. Although the expansile force may be substantially uniform as stated, the match between the diameters of the tapered stent and the vessel into which the stent is placed may result in the vessel being exposed to a force lesser than would be exhibited by a straight stent.

In another embodiment according to the present invention, a template possessing a uniform diameter as described above may be chosen for use with either the hand weave method or a machine method. The diameter of this template may correspond to the diameter of the largest portion of the stent. Tapered body 100 may be woven around this template and heated and cooled as above described. The wire ends of closed structures 104 may then be reinforced as needed for the application. Tapered body 100 may then be mounted on a tapered template in a fashion similar to the one described above (e.g., using a copper wire), and reheated in a manner similar to the original heating. Forming the stent in this manner results in a contiguously loosening mesh toward the tapered end of the stent. That is, angle a is contiguously decreased toward the distal end 102 of tapered body 100 resulting in a decreasing expansile force of the tapered stent towards the tapered distal end 102.

It is to be understood that if a stent (or any other device disclosed herein) is remodeled a number of times and it is not intended that the stent be programmed with thermal shape memory, care should be taken not to exceed a total heating time (which includes the first heating time and the second heating time, etc.) of about 60 minutes, because at about 60 minutes, the stent may be programmed with thermal shape memory.

As with body 10, one or more of the coupled wire ends of tapered body 100 may be left slightly longer than the others and bent inward so as to allow for retrieval of the stent using a foreign body retrieval device. Further, closed structures 104 of body 100 may be flared to improve stent fixation.

In an in vitro study, the expansile force of the tapered stent of the present invention was found to be proportional to the weave tightness. The results of this study are set forth below in Table 2. The tightness of the weave is strongly associated with the angle between the crossing wires as well as with the number of wires used for creating the weave. The stents used in the study were built from 0.011 inch nitinol wires. If the angles between the crossing wires are wide (closer to 180°), the stent is better able to withstand any outer compression. An increase in the diameter of the nitinol wire would increase the expansile force of the stent.

TABLE 2

Taper-Shaped Self-Expanding Repositionable
Stent Comparative Study, Using 0.011" Diameter Wires

| Δ (mm) | 10 Wires, Tight Weave | 8 Wires, Moderate Weave | 6 Wires, Loose Weave | 6 Wires, Tight Weave |
|---|---|---|---|---|
| 2 | 115 | 91 | 26 | 92 |
| 4 | 176 | 123 | 55 | 103 |
| 6 | 208 | 141 | 74 | 119 |
| 8 | 238 | 158 | 92 | 126 |
| 10 | 273 | 170 | 103 | 136 |
| 12 | 293 | 186 | 120 | 145 |
| 14 | 331 | 202 | 129 | 153 |
| 16 | 371 | 223 | 146 | 171 |

With respect to Table 2, the inventors used the unit "g" for "grams" as the measure of force for the reasons discussed above. Similarly, the designation Δ in the leftmost column of Table 2 represents the circumferential displacement (in mm) of the stent in question. For example, a Δ of 2 mm indicates that the circumference of the stent in question was reduced by 2 mm, and the force necessary to effect that displacement was then recorded.

Advantages of the tapered stent of the present invention include superb flexibility, repositionability and removability, precise positionability, and better matching than a cylindrical stent with a uniform diameter between the tapered vessel and the stent which may result in less intimal reaction and longer vessel patency.

Covered Stents

Various material may be suitably used as grafts (including materials used as covers and those used as liners) that may be attached to the present woven stents so as to create stent grafts. One type of covering material that may be utilized for this purpose is made from material that is stretchable enough to substantially follow the movement of the stent's mesh. This type of graft material includes woven polyester, Dacron, polyurethane and the like. Depending on the application, the graft material may, for example, be somewhat porous (to facilitate endothelial ingrowth), highly porous (to leave bridged side branches patent) or non-porous (e.g., to exclude an aneurysm or fistula from circulation, or in another application to prevent tumor ingrowth into the stent graft lumen).

The graft material may be attached to either the outer or the inner surface of the stent, so as to serve as a cover or a liner, respectively. The graft material may be attached to the stent using monofilament sutures (e.g., polypropylene such as 5-0, 6–0, 7-0 Prolene, which is commercially available from Ethicon), glue, heat, or any other appropriate means.

Graft materials that are not stretchable or elastic may also be utilized to form stent grafts. One such material is PTFE. Such graft material may be attached to only one of the stent end's, thereby allowing free movement of the wire mesh. The attachment between the stent and the graft material may be created at the proximal end of the resulting stent graft (that is, the end of the stent that will be closest to the operator).

Such a stent graft may be pre-loaded into an appropriately-sized sheath. The graft material may be folded or arranged so that it occupies as little space within the sheath as possible.

Delivering a stent graft having a graft material made from a relatively non-stretchable material such as PTFE may be performed in a manner that is different than the manner in which a stent graft having a stretchable graft material may be delivered. For example, with a stent graft having a cover made from relatively non-stretchable graft material, after the stent graft is positioned as described below in greater detail, the sheath may be retracted and the graft material may thereby be exposed. Then the stent may be allowed to assume its unconstrained diameter by using the coaxial delivery system. The fact, that the coaxial delivery system enables to achieve a more compressed mesh tightness than that achievable by allowing the stent to recover, may be advantageous to create an adequate contact between both the stent and the graft as well as between the stent graft and the vessel wall. The different delivery mechanism requires a different approach to stent graft retrieval. First, the stent is completely restretched over the delivery tubes and the stent's completely elongated position is secured by the proximal lock mechanism. Second, the sheath is advanced preferably using some rotating movement to recapture the graft material. The creation of the attachment site between the stent and the graft at the proximal end of the stent is advantageous for possible repositioning. The stent's proximal end is secured to the outer delivery tubes, and the graft to the proximal end of the stent, therefore, the proximal portion of the graft is formed into a funnel shape facilitating its retrieval into the sheath.

Side-By-Side Stent Placement in Aorta and Bilateral Renal Artery

Figure 54:
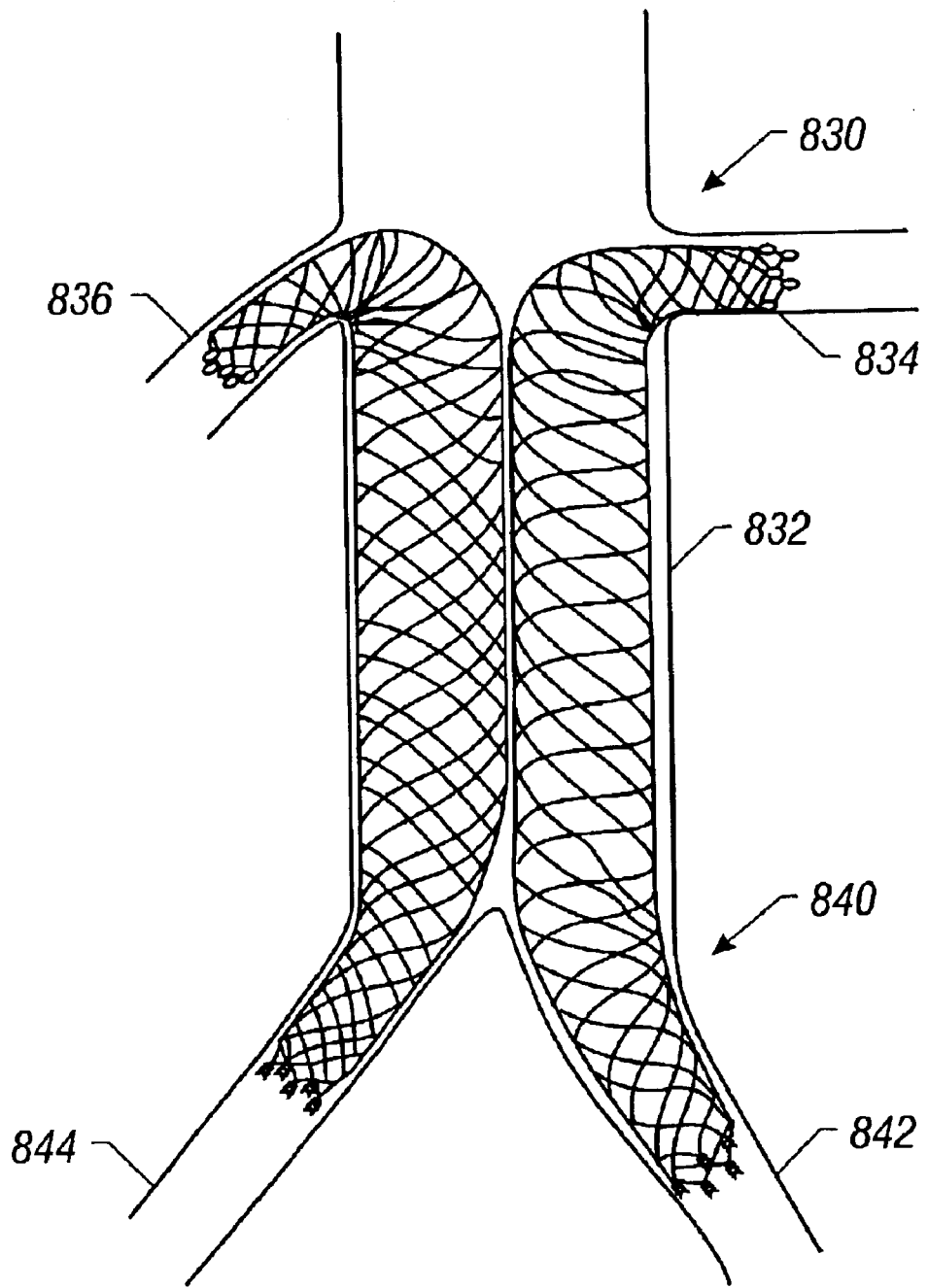
FIG. 54 is a front view of two stents placed in side-by-side relationship with each other in the aorta according to one embodiment of the present invention.

The present stents may be delivered in a variety of anatomical structures. Further, they may be used in conjunction with each other in a variety of manners to best treat the diseased structure. For example, as shown in FIG. 54, the bilateral aorto-renal junction 830, consisting of aorta 832, left renal artery 834 and right renal artery 836, along with the aorto-iliac junction 840, consisting of left iliac artery 842 and right iliac artery 844, may be treated using uses two stents positioned in side-by-side relationship with each other. Alternatively, stent grafts shorter in length than those shown in FIG. 54 may be delivered within the aorta or the aorto-iliac junctions with some overlap therebetween.

The stents that may be utilized may be woven and annealed as described above on a variety of templates. In one embodiment, straight templates may be used. The stents may also be woven and annealed as described above so as to be relatively tapered, such as those in FIG. 54. In such a configuration, the portions of the stents that will occupy the aorta may be larger in caliber than those portions of the stents that will occupy the renal arteries. The stents may also be woven on templates that are configured with a bend that may approximate or match the angle between the appropriate renal artery and the aorta.

Figure 55:
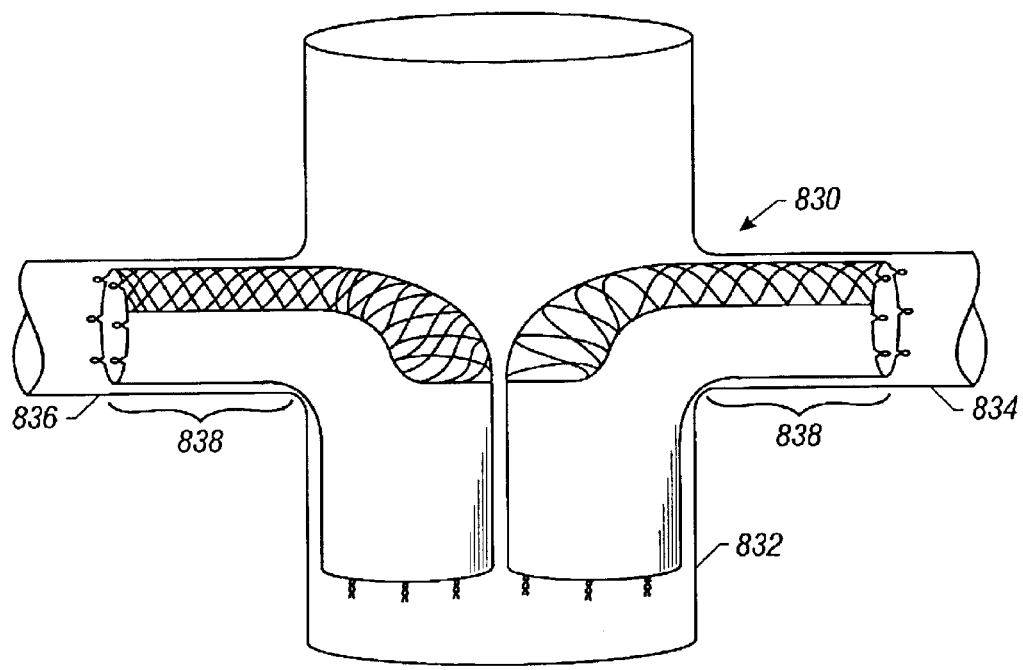
FIG. 55 is a perspective view of two partially-covered stents placed in side-by-side relationship with each other in the aorta according to one embodiment of the present invention.

Stents that may be partially or completely provided (i.e., covered or lined) with any of the graft materials described above using any of the methods of connection described above may be used in this application. In the embodiment of the pair of stents illustrated in FIG. 55, the portions of the stents that occupy aorta 832 and portions of the stents proximate the caudad surfaces 838 of renal arteries 834 and 836 are covered. By only partially covering the portions of the stents that will occupy renal arteries 834 and 836, the possibility of endoleak from the renal arteries may be greatly reduced or eliminated.

Figure 56:
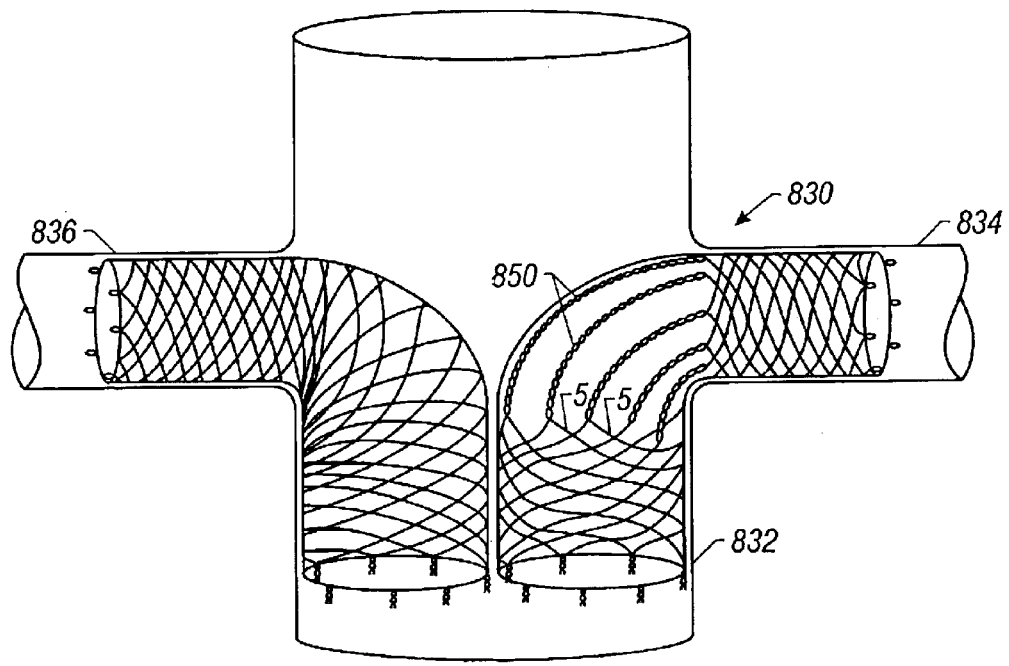
FIG. 56 is a perspective view of a stent having struts placed in side-by-side relationship with another stent in the aorta according to one embodiment of the present invention.

In another possible embodiment suitable for this application illustrated in FIG. 56, the aorto-renal stent may include struts 850 that may be formed by twisting neighboring segments of wires 5 during the weaving process. Struts 850 may also be formed in any suitable manner such as by encasing neighboring segments of wires 5 in flexible tubes, such as those made of nitinol, or by soldering or welding neighboring segments of wires 5 together, etc. As used herein, "struts" means segments of wires that are joined together in any suitable manner such as twisting, encasing within a sufficiently flexible piece of tubing, soldering, welding, etc., such that the portion of the stent formed from the struts is less disruptive of the blood flow therethrough than would be the same portion formed from a weave. The stent graft having struts 850 may, like the stent grafts depicted in FIG. 55, be covered partially with any suitable graft material, such as those relatively stretchable materials disclosed above. Accordingly, the portions surrounding struts 850 may be covered while leaving struts 850 uncovered and therefore arranged so that when delivered as shown in FIG. 56, struts 850 are advantageously positioned within the vasculature with regard to hemodynamics. The use of struts 850 in this fashion may be advantageous in comparison to leaving a similar portion of the stent utilized simply bare, as in FIG. 55, in that struts 850 would be less likely to create turbulence in the blood flow.

In one embodiment of the stent graft illustrated in FIG. 56 having struts 850, different portions of the stent may be provided with different numbers of wires. Turning to such a stent, the weave may begin at the end of the stent that will be placed in the renal artery and made be made from n wires. The portion of the stent occupied by struts 850 may also be made from n wires. The larger portion of the stent that will occupy the aorta may use n+x wires, where x denotes the number of additional wires utilized, and may be between 1 and 2n. Preferably, x is selected from an integer between 2 and n, and more preferably x equals n. The template on which this type of stent is formed may have pins 304 positioned, for example, at locations proximate the end and beginning of struts 850.

Biodegradable Devices

Both the straight and the tapered stents of the present invention (as well as the filters and occluders discussed below), except for the single wire embodiments of these devices, may be formed with filaments made of biodegradable, material so as to form self-expanding, bioabsorbable, biodegradable stents that may, in addition to functioning as stents, function as drug or nutrient delivery systems as a result of the material used.

Many factors may be considered in choosing materials from which to form the biodegradable stents of the present invention. In one embodiment, the biodegradable stents of the present invention may be formed from materials of minimal thickness so as to minimize blood flow blockage and facilitate bioabsorbtion. In another embodiment, the material may be chosen so as to exhibit sufficient radial strength to allow the body formed to function as a stent. The material from which the biodegradable stents may be formed may also degrade within the bloodstream over a period of weeks or months, so as not to form emboli. The material may be chosen such that the stent does not degrade before an endothelial layer forms in the stented vessel or structure in cases in which stenosed aortoiliac arteries with lengthy affected segments are treated. The material chosen may be chosen to be compatible with surrounding tissue in the vessel as well as with blood.

The body of a biodegradable stent may be formed by plain weave using the methods above described. The size of the filaments used may vary according to the application. In some embodiments, the filaments may be reduced in size in comparison to the size of wires used in comparable applications involving non-biodegradable devices. In other embodiments, the number of filaments used may be increased in comparison to the number of wires used in comparable applications involving non-biodegradable devices.

The minimum number of filaments that may be used to create the body of a biodegradable device (including stents, occluders and filters) may be about 5. In one embodiment, 12 filaments may be used. With regard to stents, in creating the body using plain weave, the angle of the crossed filaments (described above as angle a) may vary as described above, but is typically 150–160°. In one embodiment, the angle of the crossed filaments may be as large as possible to achieve the largest radial force possible and further ensure that the stent may have enough expansile force to remain in place after being delivered. The filament ends, after plain weaving is complete, may be coupled together to form closed structures using any suitable means such as by heat treatment or sealing, gluing, tying, twisting, crimping, taping, or the like. In another embodiment, a long body may be woven, and the body may be cut into tubular segments. Closed structures may be formed at both ends of the segmented bodies by coupling the filament ends together as above described.

In one embodiment, the filaments used may be made of polyglycolic acid ("PGA"), poly-L-lactic acid ("L-PLA"), polyorthoesters, polyanhydrides, polyiminocarbonates, or inorganic phosphates. These polymers are commercially available from United States Surgical Corporation, Norwalk, Conn.; Birmingham Polymers, Inc., Birmingham, Ala.; and Ethicon, Sommerville, N.J., for example. One factor to consider in choosing a material from which to make the filament will be the goal of the stent placement. For example, in an embodiment in which the stent serves mainly as a drug delivery system, PLA may be used because of its rapid degradation time. In another embodiment in which the stent serves mainly to maintain the patency of the vessel (i.e., keeping the vessel open) and as a scaffold or frame for the development of a new endothelial layer, PGA may be used considering its high strength and stiffness. In other embodiments, glycolide may be copolymerized with other monomers to reduce the stiffness of the resulting fibers that may be used.

In another embodiment, any of these filaments may be provided with about 0.05 to 0.25 percent by weight of a basic metal compound, such as calcium oxide, calcium hydroxide, calcium carbonate, calcium phosphate, magnesium oxide, magnesium hydroxide, magnesium carbonate, magnesium phosphate, sodium phosphate, potassium sulfate or the like, to increase the in vivo strength retention of the biodegradable stent by about ten to twenty percent or more, as described in U.S. Pat. No. 5,478,355 to Muth et al. (1995), which is hereby expressly incorporated by reference. As used herein, "in vivo strength retention" refers to the ability of a biodegradable body to retain its strength (i.e., the breaking load of the body) after being implanted or delivered into a living creature. In yet another embodiment, a filament obtained from a polymer containing about 15 to about 30 mole percent glycolide in a melt spinning operation, as described in U.S. Pat. No. 5,425,984 to Kennedy et al. (1995), which is hereby expressly incorporated by reference, may be used to form a biodegradable body.

The filaments of the biodegradable devices may incorporate one or more drugs that positively affect healing at the location where the stent is delivered. In one embodiment, these drugs may include anticancer drugs such as paclitaxel (which is commercially available as TAXOL, from Bristol-Myers Squibb in Princeton, N.J.) or docetaxel (which is commercially available as TAXOTERE, from Phone-Poulenc Rorer in Collegeville, Pa.), fibroblast/smooth muscle cell proliferation-preventing agents, and antithrombogenic drugs such as heparin which is commercially available from Wyeth-Ayers in Philadelphia, Pa.

One or more drugs may be incorporated into a polymer using any suitable means. For example, in one embodiment, the drugs as a solute may be dissolved in the biodegradable polymer as a solvent to form a solution. The solution may then be hardened into a fiber from which the stent may be woven. In another embodiment, simple mixing or solubilizing with polymer solutions may be utilized. The drugs may also be dispersed into the biodegradable polymer during an extrusion or melt spinning process. In yet another embodiment, the biodegradable fibers that have already been formed may be coated with drugs.

The biodegradable filaments may be rendered radiopaque to facilitate their monitoring under fluoroscopy and/or their follow-up using radiographs, fluoroscopy, or computerized tomography. The methods described above for incorporating the drugs into the polymer may be used to mix radiopaque salts, such as tantalum, with the polymer.

As used herein, "degradation time" refers to the time during which the biodegradable device maintains its mechanical integrity. One factor that should be considered in choosing a polymer in light of its degradation time is that the polymer will loose its mechanical integrity before it is completely absorbed into the body. For example, pure polyglycolide (PGA) sutures lose about 50% of their strength after 2 weeks, and 100% at 4 weeks, and are completely absorbed in 4–6 months. For vascular applications (i.e., applications in which the stent is placed within a vessel in a body), polymers having degradation times of about one to twenty-four months may be used, depending on the application. In a typical embodiment, a polymer having a degradation time of about one to three months may be used. In choosing a polymer for non-vascular applications such as the esophagus, colon, biliary tree, ureter, etc., one should consider the polymer's ability to withstand the chemical stimuli in the given environment.

During the degradation time of a biodegradable stent, a new endothelial layer may form on the surface of the stent. The rate of the release of the drugs which may be incorporated into the polymers may be controlled by the rate of degradation of the biodegradable material used. Thus, the rate of release of a drug may act as a control quantity for the rate of degradation. At the same time, other agents such as fibronectin from human plasma (commercially available from Sigma, St. Louis, Mo.) may be added to the polymer used (using any suitable means described above for incorporating drugs into the chosen polymer) and may affect the rate of biodegradation. For example, fibronectin may accelerate the growth of cells around the surrounding stent, which, in turn may accelerate the resorption reactions around the stent.

In one embodiment of a biodegradable body according to the present invention, one or more shape memory wires may be added to the body for reinforcement after it is formed using plain weave. Such wires may comprise nitinol or any other comparable material above described. In one embodiment, the wires may be formed from nitinol having about 55 to 56% Nickel and 45 to 44% Titanium (Shape Memory Applications). The wire or wires may be incorporated into the woven biodegradable body by threading the wire in and out of openings in the body several times. In one embodiment, the manner in which the wire is threaded in and out of openings in the body is shown in FIG. 31. In FIG. 31, designation 520 shows reinforcement wire 510 passing outside biodegradable body 500, and designation 530 shows reinforcement wire 510 passing inside biodegradable body 500, thus showing how wire 510 may be threaded in and out of openings in body 500. As shown in FIG. 31, the reinforcement wire(s) 510 may be led between (i.e., parallel to) two biodegradable filaments 540 and may follow their helical course. As shown in FIG. 31, reinforcement wire 510 may be secured to body 500 with loops 550, or any other suitable means such as tying, twisting, or the like. Loops 550 may be placed around a filament or around the intersection of one or more filaments. As a result, the wire can move in harmony with the weave and will not interfere with the movement of the filaments in the weave. By activating the superelasticity or thermal shape memory of reinforcement wire 510, ends 560 and 570 of body 500 may be pulled together, resulting in a tighter weave. As a result, the expansile force of the stent and its resistance to outer compression may significantly increase. In one embodiment, loops 550 may also be used in securing body 500 to a delivery system.

Figure 32:
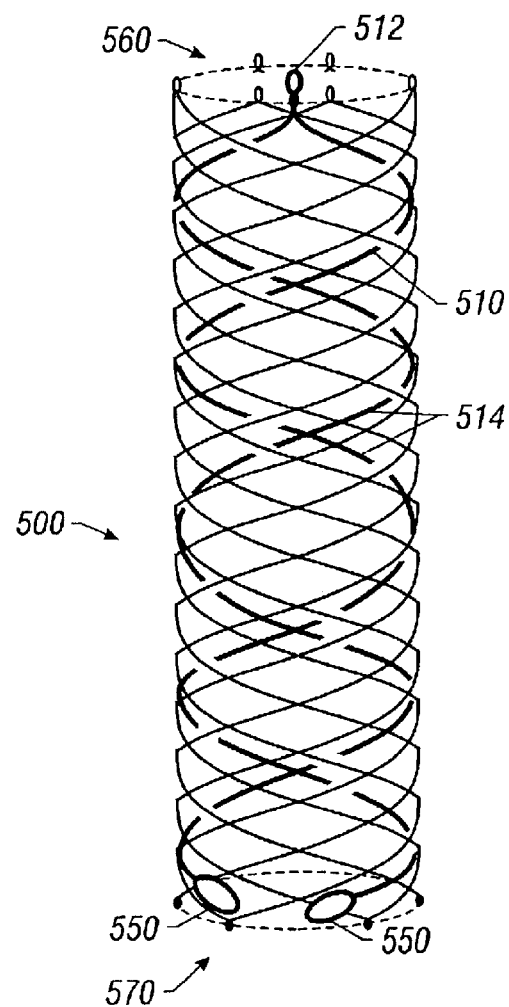
FIG. 32 is a perspective view of a biodegradable stent with a reinforcing wire according to a second embodiment of the present invention.

In another embodiment shown in FIG. 32, in which a reinforcement wire is threaded in and out of openings in a biodegradable body according to the present invention, reinforcement wire 510 may be bent at a selected point located between its ends, typically at about the mid-point of the wire, and a small loop 512 may be created (similar to the small closed loops described above). As shown in FIG. 32, small loop 512 may be entwined around a filament or the intersection of one or more filaments, and reinforcement wire 510 may be threaded in and out of the openings in body 500 as described above, and may be secured to body 500 with loops 550, or any other suitable mean, as above described. Both portions 514 of reinforcement wire 510 may be symmetrically led along both sides of body 500 following the sinuous/helical course of the biodegradable filaments. As described earlier, by activating the superelasticity or thermal shape memory of reinforcement wire 510, ends 560 and 570 of body 500 may be pulled together, resulting in a tighter weave. As a result, the expansile force of the stent and its resistance to outer compression may significantly increase. In one embodiment, loops 550 may also be used in securing body 500 to a delivery system.

In one embodiment, the size of reinforcement wire 510 may range from about 0.005 inches to about 0.012 inches. It is to be understood that increasing the size of reinforcement wire 510 may increase the force with which ends 560 and 570 are pulled together when the shape memory of the wire is activated. It is to be understood that using more than one wire may have the same effect as increasing the size of the wire.

In one embodiment, reinforcement wire(s) 510 may be formed around a template as above described. The reinforcement wire(s) may then be programmed with superelasticity or shape memory as described herein.

Bench-Work

With regard to the biodegradable version of the stents according to the present invention, the inventors have used an open-ended plain woven nylon body (that is, the filament ends were not coupled together to form closed structures after weaving) for initial bench work. The tubular body was woven using 0.007 inch nylon filaments. The number of filaments used was 16, and the unconstrained diameter of the tube was 11 mm. In an unconstrained state, the size of the weave holes was approximately 1 mm. The expansile force of the tube was relatively good, and after maximum elongation the tube readily reverted to its unconstrained diameter. Compressing the tube from its two ends longitudinally, the expansile force could be increased considerably. At the maximal longitudinal compression, the diameter of the tubular mesh was 13 mm. Holding both ends of the tube, the stent became virtually incompressible.

A 0.006" nitinol wire was threaded through the holes of the unconstrained mesh in the manner described earlier. The wire was a straight nitinol wire and was not formed on a template and programmed with either shape memory or superelasticity. The straight wire caused the mesh to elongate and the unconstrained diameter of the tube decreased to 9.5 mm (13% lumen-loss) though the other characteristics of the mesh did not change. The woven tubular structure could be elongated completely as well as compressed maximally.

1.5 Occluders

With reference to the illustrative embodiments shown in FIGS. 33A–G, 34, and 35, there are shown occluders for insertion and delivery into an anatomical structure. An occluder according to the present invention may be used to substantially or completely prevent the flow of blood through a vessel. Body 700 of the occluder may be formed using plain weave by the methods above described. The types of structures into which an occluder according to the present invention may be placed include arteries, veins, patent ductus arteriosus, and the ureter.

Figure 33A:
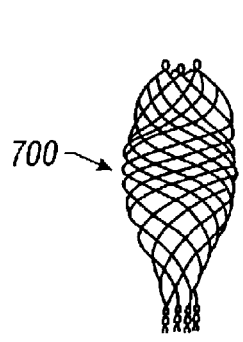
Figure 33B:
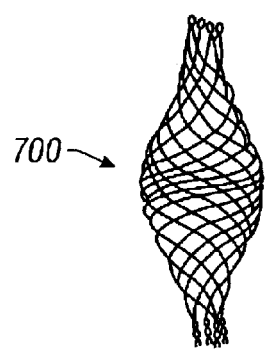
Figure 33C:
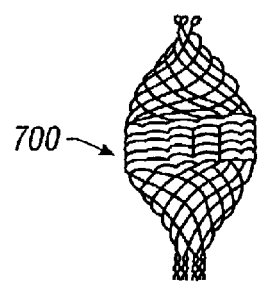

In one embodiment of the present invention, an occluder may be formed by weaving a body for use as a stent as above described. The body may then be heated and allowed to cool as above described. The body may then be remodeled (i.e., mounted on another template in a manner similar to the manner in which the body was coupled to the first template (e.g., using a copper support wire)), and reheated and cooled in a manner similar to the original heating and cooling. The template that may be used in the remodeling may have the desired shape of the occluder in one embodiment. In another embodiment, a tubular template, preferably with a smaller caliber than that of the original template, may be used. In this embodiment, after securing one end of the body to the template using support wire or any other suitable means, the distance between the two ends of the body may be appropriately decreased. As a result, the mid-portion of the body will balloon outward (FIG. 33B). Depending on the distance between the two ends of the body, a series of different shapes may be created. The shapes may include a round shape (FIG. 33A), an elongated fusiform shape (FIG. 33B), a compressed fusiform shape (FIG. 33C), a compressed fusiform shape with an inverted distal end (FIG. 33D), a flat disc configuration (FIG. 33E), a shape in which the proximal end of the occluder is inverted into the body of the occluder (FIG. 33F), a torpedo shape (FIG. 33G), etc. After achieving the desired shape of the body, the other end of the body may also be secured to the template. The body/template unit may then be heated and cooled again. The heating temperatures and times disclosed above may be utilized.

To increase the thrombogenicity of the occluder, (i.e., the ability of the occluder to prevent the flow of fluid) thrombogenic materials in the form of an occluding agent may be enclosed within the body. Any suitable material may be used for the occluding agent. The size and shape of the occluding agent may be varied according to need. In one embodiment, one or more threads of polyester may by used as an occluding agent. The threads may be coupled to the body at one or both of the ends of the body using any suitable means such as sutures. The threads may also be placed loosely within the body. In another embodiment, DACRON threads may be used as an occluding agent. The DACRON may be coupled to the body at one or both ends of the body using any suitable means such as monofilament sutures, glue, or the like. The DACRON may also be placed loosely within the body.

In one embodiment of the present invention, a stretchable jacket may be configured to cover at least a portion of the body of an occluder (FIG. 34). Any suitable material may be used for the jacket. In one embodiment, the jacket may be made of polyurethane. In another embodiment, the jacket may be made of silicone. The jacket may have a thickness of about 0.02 mm, but it will be understood that any suitable thickness may be substituted therefor. The jacket may be coupled to either the inner or outer surface of the body using glue, heat, or any other suitable means. In one embodiment, by coupling the jacket to the outer surface of the body, the body may be easily manipulated within a hollow covering such as a sheath during the insertion and delivery of the occluder.

The closed structures of the ends of the body used as the occluder may be held together using any suitable means. In one embodiment, a monofilament suture (polypropylene, Prolene 5-0, 6–0, 7-0, from Ethicon) may be used to hold the closed structures of the body together by threading the suture through the closed structures or other nearby openings. In another embodiment, metal clips 710 may be used to hold the closed structures of the body together (FIG. 35). In holding the closed structures together, in one embodiment, the closed structures may be held together such that the tubes of the delivery system (described in detail below) may easily pass through the lumen of the occluder. In another embodiment, the closed structures of the ends of the body may not be held together.

During deployment of such as occluder, the interventionalist is always able to correct any misplacement by simply restretching the wire mesh and repositioning the body using the delivery system. Even after the distal end of the occluder has been released, the proximal end still remains attached to the delivery system offering another safety feature for removal of the occluder.

Figure 57A:
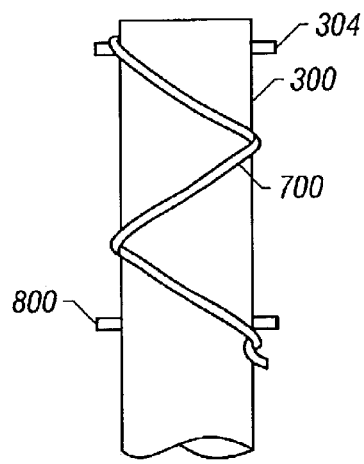
FIG. 57A is a front view of an occluder formed from a single wire around a template according to one embodiment of the present invention.

The single wire embodiment may also be utilized as a structure for causing vessel occlusion. Such an occluder should have at least two loops. FIGS. 57A–D illustrate various single wire embodiment occluders. FIG. 57A illustrates body 700 on template 300 after having been formed thereon using, for example, either the hand weave or machine weave method described above. As shown, body 700 of the occluder has 3 loops. At this stage of the development of the occluder illustrated in FIG. 57A, body 700 is simply a single wire embodiment stent.

After the body/template unit has been annealed using, for example, the annealing method described above for imparting body 700 with superelastic properties, body 700 may be removed from template 300. Body 700 may then be stretched by pulling the two ends thereof longitudinally apart, and collars 702 may be slipped over either end and placed at the locations where first segment 704 and second segment 706 cross each other. Collars 702 may be small pieces of metal, such as small pieces of a nitinol tube (commercially available from Shape Memory Applications, Santa Clara, Calif.). In doing this, segments 704 and 706 extend between the loop-defining locations hidden by collars 702 so as to form loops 710. A collar 702 may also be placed around the ends of the wire forming body 700. At the loop-defining locations, which are hidden by collars 702, segments 704 and 706 may be positioned adjacent to each other. As used herein, segments that are "adjacent" to each other may or may not touch each other, but such segments are positioned in close proximity to each other such that the distance separating them is generally no more than about 1 mm. The length of the wire segments covered by collars 702 should be sufficiently short so as not to impede the flexibility of the single wire embodiment occluder.

Although not shown, it will be understood to those of skill in the art, with the benefit of this disclosure, that any suitable means may be used to secure segments 704 and 706 adjacent to each other in the loop-defining locations. Such means include wrapping the segments together with any suitable wire, crimping a piece of metal around the segments, welding the segments together, and the like.

Figure 57B:
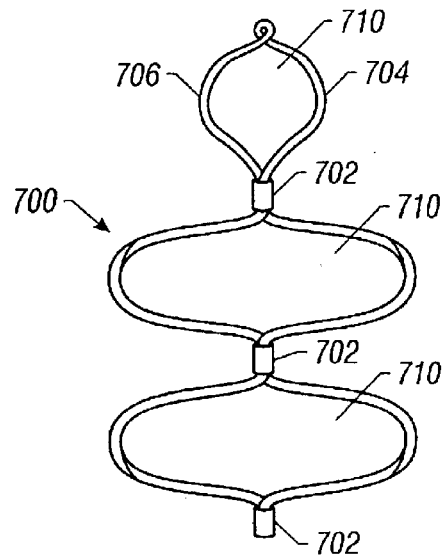
FIG. 57B is a perspective view of an occluder formed from a single wire that includes collars placed around the wire segments at loop-defining locations according to one embodiment of the present invention.

With collars 702 in place, the shapes of loops 710 are altered such that loops 710 possess generally compressed shapes. As shown in FIG. 57B, the two largest of the three loops 710 have fairly pronounced compressed shapes relative to the smallest loop 710. The compressed shape may exaggerated (i.e., made more compressed) by decreasing the distance between collars. Laterally pulling the portions of segments forming a given loop apart may be done to alter the distance between collars. The collars should maintain the shapes of the loops and thereby stabilize the occluder within the anatomical structure into which it is delivered. However, the collars may be crimped to further improve their ability to maintain the shapes of the loops. In this same regard, body 700 may be secured to a template having a suitable shape and re-annealed so that the compressed shapes of loops 710 are maintained. Further, re-annealing body 700 may improve the expansile force and resulting self-anchoring capability of the single wire embodiment occluder.

The number of loops utilized to form a single wire embodiment occluder may be reasonably increased. For example, an occluder formed using the single wire embodiment may have 3, 4, 5, 6 or more loops.

The shape of the loops of the single wire embodiment occluders may be varied as desired to best cover the cross-section of the anatomical structure to be occluded in a manner that will likely cause occlusion in the most rapid manner possible. Accordingly, a single wire embodiment occluder may have loops that possess differing sizes, such as an occluder having one or more loops near one end that are smaller than one or more loops near the other end of the occluder. As used herein, the total length of the segments that define a loop that is "smaller" than another loop of a single wire embodiment is less than the total length of the segments that define the larger loop. In another embodiment, the occluder may appear tapered, where the loops decrease in size from one end to the other. In another alternative embodiment, one or two small loops may be arranged at or near the mid-portion of a single wire embodiment occluder, while the loops at the proximal and distal ends may be larger by comparison and possibly equal to each other in terms of size.

Figure 57C:
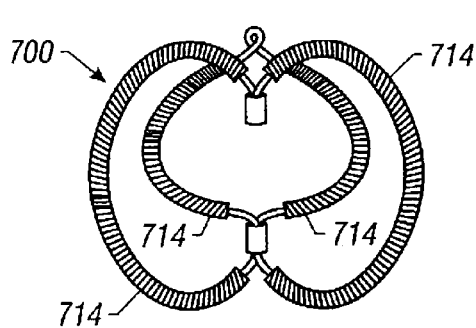
FIG. 57C is a top view of an occluder formed from a single wire that has coil pieces placed over portions of the wire segments located between collars according to one embodiment of the present invention.

In order to increase the thrombogenicity of the single wire embodiment occluders, various occluding agents may be attached to the occluder. Any suitable material may be used for the occluding agent. For example, pieces of a metal coil, such as one made from stainless steel, may be pulled over the wire segments prior to slipping collars over them. In this regard, the single wire embodiment occluder may be re-annealed as described above, the collars may be removed, the coil pieces may be placed over the segments, and the collars may be replaced at the loop-defining locations. As illustrated in FIG. 57C, coil pieces 714 are placed over the segments between collars 702. The coil pieces may also be wires, such as stainless steel or nitinol wires, that are manually wrapped around the segments and attached to the segments in any suitable fashion. The coil pieces may be pre-formed hollow pieces of coil made from any suitable metal or alloy.

Figure 57D:
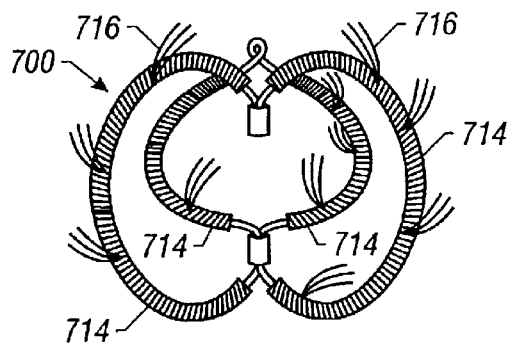
FIG. 57D is a top view of an occluder formed from a single wire that has coil pieces placed over portions of the wire segments located between collars and also has thrombogenic filaments attached to the coil pieces according to one embodiment of the present invention.

Thrombogenic filaments (such as polyester fibers) may also be attached to coil pieces 714 to further increase the thrombogenicity of the single wire embodiment occluders. As illustrated in FIG. 57D, polyester fibers 716 are attached to coil pieces 714 at various locations along the coil pieces. The length of the thrombogenic filaments may vary, as may the distance between the filaments, in order to ensure that the resulting thrombogenicity of the single wire embodiment occluder is best-suited to the application. The thrombogenic filaments may be individual fibers or bundles of fibers.

In another embodiment, segments of the single wire embodiment occluder may be covered by bundles of thrombogenic filaments, such as filaments made of polyester, such that the bundles resemble the coil pieces, and additional thrombogenic filaments, such as polyester fibers, may be attached to or braided with the bundles of filaments such that they extend away from the covered segments in the same fashion as fibers 716 illustrated in FIG. 57D.

Delivery Systems for Stents, Stent Grafts and Occluders

Figure 3:
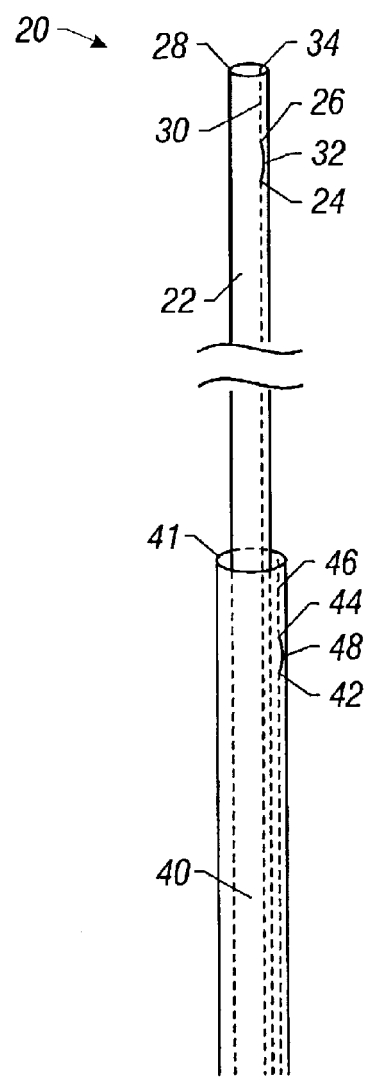
FIG. 3 is a perspective view of a delivery system according to one embodiment of the present invention.

With reference to FIG. 3, the delivery system 20 for body 10, tapered body 100 and body 700 (including biodegradable versions thereof), may consist of two flexible tubes arranged coaxially. These tubes may be formed of material such as TEFLON or NYLON, which are commercially available from Cook, Inc. (Bloomington, Ind.), or other similarly suitable materials. It is to be understood that material that is less flexible or firmer than TEFLON may also be used. Further, it is to be understood that material with a thinner wall thickness than that of TEFLON tubing, such as the material from which the WALLSTENT delivery system is formed, may be utilized. In one embodiment, one or both tubes may be made of metal, such as nitinol, which is commercially available from Shape Memory Applications. Nitinol tubes may be particularly well-suited for use in delivery systems that are relatively large or rigid, such as for tracheal or bronchial stenting.

The size of the outer diameter of the distal, small caliber tube 22 may range from 2.5 to 7.5 French ("F") depending on the application of the stent, the size of the stent, and the number of securing wires (to be discussed below) that may be used to secure the stent to tube 22 (to be discussed below). For coronary applications, for example, the size of tube 22 may be about 3-F. For delivery of a medium stent into the renal or carotid arteries, for example, the size of tube 22 may be about 5-F. The length of tube 22 may range from 80 cm to about 120 cm depending on the application of the stent and the size of the stent. In an exemplary embodiment, for example, for delivery of an iliac artery stent from a contralateral approach, the length of the tubing may be about 90 cm. In another exemplary embodiment, for carotid artery stenting, the length of the tubing may be about 110 cm. The size of the stent may also have affect the length of tube 22. Thus, in an exemplary embodiment, the larger the stent diameter, the longer the stent is in its completely elongated state.

Figure 25:
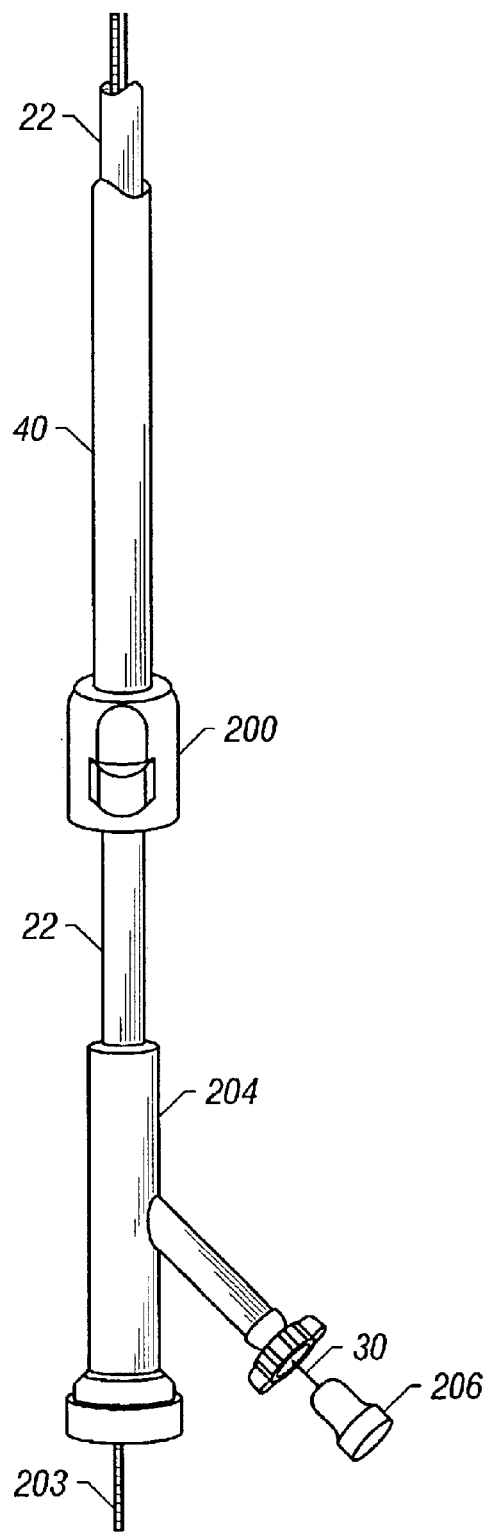
FIG. 25 is a front view of the proximal portion of a delivery system according to one embodiment of the present invention.

Tube 22 as well as tube 40 (discussed below) may be provided with a flange or hub near its proximal end so as to allow for control of the position of tube 22 during delivery of the stent. In an exemplary embodiment as shown in FIG. 25, a push button lock/release mechanism 200 (such as a FloSwitch®BP device from Meditech/Boston Scientific Corp., Watertown, Mass. or a CRICKETT device from Microvena in White Bear Lake, Minn.) may be utilized for securing tube 40 to tube 22 when necessary. As further illustrated in FIG. 25, an end fitting 204 with a side arm may be utilized with a Luer-lock mechanism and/or tightening screws for further facilitating delivery of the stent. Although not shown, it will be understood by those of skill in the art, with the benefit of this disclosure, that the hub or flange that may be provided on the end of tube 22 may be used to facilitate the connection between end fitting 204 and tube 22. Similarly, although not shown, it will be understood by those of skill in the art, with the benefit of this disclosure, that the end of tube 40 may be provided with a hub or flange that may be used to facilitate the connection between push button lock/release mechanism 200 and tube 40. End fitting 204 may be equipped with separated lumens in a double channel system. One or more steerable guidewires 203 may be utilized in the lumen of tube 22 and in the lumen of end fitting 204 for facilitating delivery of the devices described herein.

It is to be understood that radiopaque markers may be placed on tube 22 at appropriate locations in a manner known in the art in order to better enable viewing of tube 22 using fluoroscopy during delivery of the stent.

As shown in FIG. 3, the distal, smaller caliber tube 22 is equipped with proximal hole 24 and distal hole 26. Distal hole 26 may be typically located between about 0.5 and about 3.0 cm from distal end 28 of tube 22, most typically about 1 cm. The location of the radiopaque markers on tube 22 may affect this distance. The distance between holes 24 and 26 may be typically about 3 to 8 mm, but most typically about 3 to 5 mm. This distance may be affected by the size of the securing wire 30. For example, the distance between the holes may decrease as the diameter of wire 30 decreases.

Securing wire 30 may be placed within the lumen of tube 22 (the dotted line indicates that securing wire 30 is located within tube 22), and may pass through holes 24 and 26 so as to form a small-profile, tight securing loop 32 between the two holes. Distal end 34 of securing wire 30 terminates at or near distal end 28 of tube 22. Proximal end of securing wire 30 may be connected to a handle 206 as shown in FIG. 25.

Securing loop 32 holds the small loops (6 and 106) or bends (8 and 108) of distal end (12 or 102) of body 10 or tapered body 100 in position during delivery (delivery being described in more detail below.) Advantageously, securing loop 32 also prevents premature delivery of the stent. Thus, prior to delivery of the stent, distal end 34 of securing wire 30 passes out through proximal hole 24, passes through the small loops or bends of the stent, and passes back into the lumen of tube 22 through distal hole 26, terminating prior to distal end 28, thus securing the distal end of the stent to tube 22. It is to be understood that securing wire 30 may pass through one of the openings in the plain weave of body 10 or tapered body 100 other than the small loop (6 and 106) or bend (8 and 108).

In most applications, securing wire 30 ranges in size from about 0.006 inches to about 0.011 inches in diameter. However, the size of securing wire 30 in any given application depends upon several factors. For example, a larger (in terms of diameter) securing wire provides more resistance to the propensity of a stretched stent to contract than does a smaller wire. Additionally, when more than one securing wire is utilized, the size of the wires can be less than if only one securing wire were used. The securing wires of the present invention may be made of any of the shape memory materials described above. In one embodiment, the securing wires of the present invention are made of nitinol. In another embodiment, the securing wires of the present invention may be formed of nitinol having about 55 to 56% Nickel and about 45 to 44% Titanium (commercially available from Shape Memory Applications). In an embodiment in which the securing wires of the present invention are nitinol (including wires 30 and 46, discussed below), the nitinol securing wires may be heat treated as described herein or purchased from a manufacturer such that the superelastic properties of the nitinol may be utilized.

The proximal, larger caliber tube 40 is also equipped with proximal and distal holes 42 and 44 typically located in approximately the same location from distal end 41 of tube 40 as are holes 24 and 26 from distal end 28 of tube 22. The distance between holes 42 and 44 is also comparable to the distance between the holes in tube 22.

The size of the outer diameter of the proximal tube 40 may range from about 4.5-F to about 10-F depending on the application of the stent, the size of the stent, and the number of securing wires that may be used to secure the proximal end of the stent to tube 40 (to be discussed below). For coronary applications, for example, the size of tube 40 may be about 5-F. In an exemplary embodiment, for carotid artery stenting, the size of tube 40 may be about 7 to about 8-F. The length of tube 40 may range from about 70 cm to about 110 cm depending on the application of the stent and the size of the stent. In an exemplary embodiment, the length of tube 40 may typically be about 10 cm to about 20 cm shorter than the length of tube 22. It is to be understood that the proximal end of tube 22 may extend beyond the proximal end of tube 40, just as distal end 28 of tube 22 extends beyond distal end 41 of tube 40 as shown in FIG. 3. In an exemplary embodiment, the factor that may primarily influence the length of the delivery system (i.e., tubes 22 and 40) is the distance of the stented region from the access site (typically the femoral artery). As with tube 22, tube 40 may be provided with a flange or hub near its proximal end so as to allow for control of the position of tube 40 during delivery of the stent.

It is to be understood that radiopaque markers may be placed on tube 40 at appropriate locations in a manner known in the art in order to better enable viewing of tube 40 using fluoroscopy during delivery of the stent.

Securing wire 46 is positioned with the lumen of tube 40, and forms small-profile, tight securing loop 48 in the manner above described. Securing loop 48 holds closed structures (4 and 104) of proximal end (2 and 112) of body 10 and tapered body 100 in position during delivery, and advantageously prevents premature delivery of the stent. It is to be understood that securing wire 46 may pass through one of the openings of the plain weave of body 10 or tapered body 100 other than the closed structures. The closed structures are secured using the manner described above for the loops or bends.

Securing wire 46 and securing wire 30 may be formed from the same materials as the wires making up the stent. Additionally, securing wire 46 may be approximately the same size as securing wire 30, and the same types of factors discussed above should be considered in sizing securing wire 46.

In FIG. 3, although only one securing loop is shown on either tube, it is to be understood that more than one securing loop may be utilized on each tube to secure the proximal and distal ends of the stent. More securing loops may be achieved with the same securing wire, or by using more securing wires. As discussed above, the number of securing wires that may be used may depend on several factors, such as the amount of force needed to elongate or constrain the stent prior to delivery. For example, the more resistant the stent is to elongation, the more securing wires may be used in order to facilitate the stretching or elongation of the stent on the delivery system. By this means, the ends of the stent can be suspended evenly around the tubes and the friction between tubes and the profile of the elongated stent can be reasonably decreased. An additional factor affecting the number of securing wires may be the use of a guidewire (described below). In an exemplary embodiment of the delivery system according to the present invention, a guidewire may be utilized during delivery (described below). As a result, the use of a guidewire will affect the amount of space within tube 22 available for the use of the securing wire or wires. It is also to be understood that securing wires having tapered distal ends may be used no matter how many securing wires are used.

Body 700 may be secured to the delivery systems of the present invention the delivery system depicted in FIG. 3, in the same manner in which body 10 and tapered body 100 may be secured to these delivery systems as above described. In one embodiment in which the ends of body 700 are secured to tubes 22 and 40, one small-profile, tight securing loop may be used to secure each end.

Figure 4:
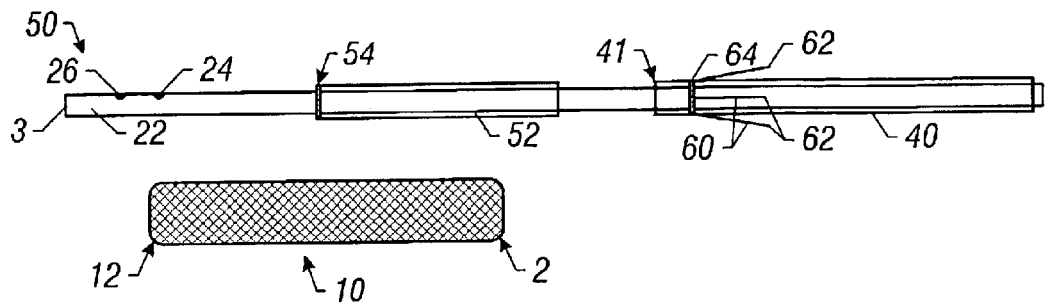
FIG. 4 is a side view of a delivery system according to one embodiment of the present invention.

With reference to another illustrative embodiment of the delivery system according to the present invention shown in FIG. 4, delivery system 50 has tube 22 equipped with proximal and distal holes 24 and 26 in the manner above described. As shown, delivery system 50 may consist of thin-walled sheath 52 arranged coaxially with tube 22. Sheath 52 may be formed of materials comparable to those from which tubes 22 and 40 are formed. Sheath 52 may be about 1 cm to about 2.5 cm in length, but typically about 1.5 cm. The distal end 54 of sheath 52 is connected or attached to tube 22 by gluing, melting, heating or any other suitable means at a location typically between about 8 cm to about 20 cm from distal end 28 of tube 22, but most typically about 15 cm.

As shown in FIG. 4, delivery system 50 may consist of inverse tabs 60 which are connected to or engaged with the distal end of tube 40. Inverse tabs 60 are connected to or engaged with tube 40 by any suitable means, including the use of a metal ring friction fitted around tube 40, to which tabs 60 may be soldered, welded, or integrally formed. Inverse tabs 60 are connected or engaged with tube 40 at a location that may be determined based on the completely stretched length of the stent. Inverse tabs 60 may be made of any suitable material, including those from which the wires of the stent may be made, and further including stainless steel and other similar materials.

The following description applies to both body 10 and tapered body 100. However, reference is made only to body 10 by way of example. Inverse tabs 60 secure proximal end 2 of body 10 in the following general manner. Inverse tabs 60 are placed within the lumen of body 10. Proximal ends 62 of inverse tabs 60 are then "threaded" through closed structures 4 or other holes located near the proximal end 2 of body 10. Tube 40 is then moved in a proximal direction until closed structures 4 (or other holes) are secured by the inverse tabs. The space created between sheath 52 and tube 22 may be used to house inverse tabs 60 as below described.

Delivery of the Stents, Stent Grafts and Occluders

Body 10 and tapered body 100 (including biodegradable versions thereof), and body 700 may be delivered in a similar manner. Thus, the following description of methods of delivery for the stents and occluders references only body 10 by way of example.

Prior to delivery, a stent in the form of body 10 may be manually secured to tubes 22 and 40. This may be accomplished by using either securing loops in the manner described above with reference to FIG. 3 (hereinafter "version 1"), or by securing loop 32 and inverse tabs 60 in the manner described above with reference to FIG. 4 (hereinafter "version 2").

In either version, a stent is first stretched so as to reduce its diameter by an amount appropriate to allow delivery to occur. Thus, the stent may be stretched maximally or just to an extent such that it may be inserted into a vessel or non-vascular structure, and may pass through the lumen of the vessel or non-vascular structure as the stent is being positioned prior to being delivered into the vessel or non-vascular tubular structure. When delivering the single wire embodiment discussed above, it should be noted that the ratio of the constrained length of the body to the unconstrained length of the body may be significantly greater in this embodiment than in the embodiments that utilize multiple wires. Therefore, the single wire embodiment may require a greater length within the vessel or non-vascular structure in which to be manipulated and prepared for delivery than may other embodiments that utilize multiple wires.

Figure 5A:
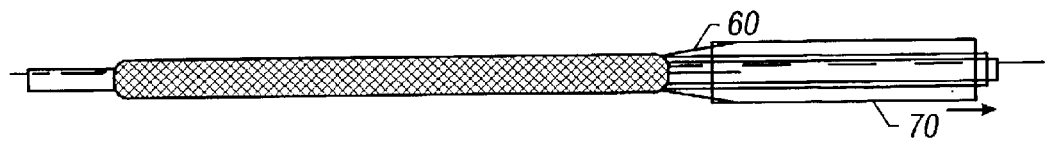

The stent to be delivered may be stretched by increasing the distance between the distal ends of tubes 22 and 40. This may be accomplished by moving or sliding tube 40 in a proximal direction over tube 22 while holding tube 22 stationary, or by moving or sliding tube 22 in a distal direction while holding tube 40 stationary, or by moving or sliding the tubes in the aforementioned directions simultaneously. Once the stent has been appropriately stretched, tubes 22 and 40 may be locked together in a manner well known in the art, such as with the use of tightening screws or push button mechanisms which are easily lockable and unlockable. If version 2 is used, an outer sheath 70 as shown in FIG. 5A may be used to cover inverse tabs 60.

In an illustrative embodiment, it is preferable to use a guidewire placed through the lumen of tube 22 for use in guiding the stent to its proper location in a manner well known in the art. The guidewire may be formed of any material from which the wires forming the stent may be made. The guidewire may be between about 0.014 inches and about 0.035 inches in diameter. In one embodiment, the guidewire may be made of nitinol (commercially available from Microvena). In another illustrative embodiment, a hollow covering such as a sheath may be placed over a stent secured to tubes 22 and 40 so as to prevent contact between the stent and the vessel or non-vascular structure during delivery of the stent.

The first step of inserting either delivery system into the body is to establish an access (arterial or venous). After puncturing the vessel using an adequate needle, a guidewire is inserted into the body. The needle is removed, and over the guidewire an introducer sheath with a check-flow adapter and preferably with a side-port is advanced. The guidewire is then removed. This introducer sheath, the size of which is determined by the size of the delivery system to be used, serves as an access for the intervention.

In version 1, when the stent, still stretched on delivery system 20, is positioned in the desired location of the vessel or non-vascular tubular structure to be stented, the sheath covering the stent may be withdrawn, and the tubes may be unlocked. The stent may be positioned and then shortened so as to achieve its unconstrained diameter in a variety of manners. In an exemplary embodiment, the distal end of the stent may be positioned in its final location prior to shortening the stent. Then, while maintaining the position of the distal end of the stent, tube 40, to which the proximal end of the stent is secured, may be moved distally over tube 22. As a result, the distance between the two ends of the stent will be shortened and the diameter of the stent will approach, and may reach, its unconstrained, preformed diameter. In another embodiment, the proximal end of the stent may be positioned in its final location prior to shortening the stent. As such, tube 40 may be held steady and tube 22 may be moved proximally within tube 40 in order to shorten the stent. In another embodiment, the middle of the stent may be positioned in its final location prior to shortening, and tubes 22 and 40 may be moved toward each other by equivalent distances. The many manners in which the stent may be positioned and subsequently shortened during delivery thereof benefit the operator by providing him or her with the versatility necessary to deliver stents within a variety of anatomical structures.

The ability to compress the woven devices disclosed herein with the present delivery systems prior to releasing them is advantageous for several reasons. Not only does it assist the operator in achieving adequate contact between the woven device and the wall of the anatomical structure such that the woven device is anchored as securely as possible, it also allows the compressed device to occupy the least amount of space along the length of the anatomical structure as possible. When using the present occluders, for example, care should be taken to limit the space along the length of the structure where occlusion is taking place so as to avoid potential complications like the undesired occlusion of side branches, and the prevention of the formation of collateral vessels supplying the structures not affected by the treated lesion. Further, when using the present filters, for example, the space along the vessel available for filter placement may be limited by the presence of the thrombotic disease and/or other anatomical considerations, such as the proximity of renal veins in the IVC, the short, free segment of the SVC, etc.

Another advantage afforded by the present delivery system relating to the ability of an operator to manipulate either or both ends of the woven body being delivered prior to releasing those ends is the ability afforded the operator to position the present woven devices accurately in irregularly diseased anatomical structures. Anatomical structures are frequently irregularly stenosed; the distensibility or enlargeability of the diseased segment may be irregular due to the presence of tough scar tissue or a tumor, for example; and lengthy vessels are naturally tapered. Because both ends of one of the present woven devices may be simultaneously manipulated while using the middle of the woven device as a point of reference prior to release, the operator may be able to position the mid-portion of the device (such as a stent) proximate the mid-portion of the diseased segment of the vessel and maintain that relationship while simultaneously withdrawing tube 22 and advancing tube 40 so as to accurately position the stent along the diseased segment. Further, by increasing the ability of the operator to accurately position the woven device and, correspondingly, reducing the possibility that the woven device will need to be resheathed and reinserted, the present delivery systems allow the operator's job of delivery less potentially disruptive to the diseased segment of the patient.

Additionally, another advantage flowing from the fact that the present delivery systems allow for compression of woven devices lies in the resulting ability of the operator delivering a stent graft having a relatively non-stretchable graft material like PTFE to achieve a mesh tightness that, in turn, may serve to create better contact between both the woven stent and the graft material as well as between the stent graft and the wall of the anatomical structure.

One of the benefits of using the present stents with the present delivery systems is that the anatomical structure being treated can always be overstented. The diameter of an anatomical structure that is "overstented" is slightly smaller than the unconstrained diameter of the stent delivered therein. In contrast, overstenting is not necessarily achievable using delivery systems that do not possess the present delivery systems' capability to manipulate the distance between the ends of the device being delivered prior to stent release. Stents that are released using such delivery systems may remain elongated within the anatomical structure into which they are delivered and, as a result, may not have a radial force sufficient to resist outer compression, which in turn could compromise the patency of the structure. Further, insufficient radial force could lead to stent migration. With the present delivery system, however, the present stents, for example, may be chosen such that their diameter is significantly greater than one hundred and ten percent of the anatomical structure being stented (110% being the norm for balloon-expandable stents, for example), such as one hundred and twenty percent, for example. Consequently, the present stents may be delivered so as to be slightly elongated within the anatomical structure in which they may be delivered (i.e., the mesh tightness of the stent may be less than the tightest achievable), yet may retain enough expansile force to keep the structure patent, withstand outer compressive forces and be unlikely to migrate.

The overdistention or overstenting of an anatomical structure using one of the present stents that is substantially or completely compressed may be beneficial for several reasons. For example, the overstenting helps ensure that the stent will remain fixed in its original location and will not likely migrate. The inventors have discovered that when the present woven bodies are compressed prior to being released, they contact the anatomical structure more securely than if they are released without first being compressed. Further, as the overstenting may be achieved using a substantially or maximally compressed stent, the near-maximum or maximum radial force of the stent may also increase the stent's ability to withstand greater outer compressive forces without elongating and thereby compromising the patency of the structure being stented. Although overstenting is described above, those of skill in the art will understand with the benefit of the present disclosure that the same principle applies with equal force to the woven filters and occluders disclosed herein, and the single wire embodiments of each, and may be achieved in the same manner.

Figure 5B:
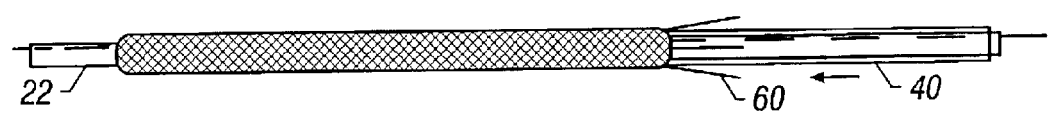

The Wallsten patent discloses a delivery system for the WALLSTENT that allows the distance between the ends thereof to be manipulated prior to the release of the WALL-STENT. However, this delivery system (depicted in FIGS. 5 and 6 of the Wallsten patent) suffers from a number of shortcomings that are overcome by the present delivery systems. For example, the Wallsten delivery system involves a number of intricate parts (such as annular members, latches, rings, cables for displacing the rings, and a casing) that version 1 does not utilize and that would likely be time-consuming and expensive to manufacture and assemble. In contrast, the simple design of version 1—i.e., two tubes and multiple securing wires—has few parts, and those parts are easily obtainable.

Another advantage afforded by the present delivery systems is that the device being delivered is clearly visible during delivery. No parts, once any delivery sheath has been removed from around the present delivery systems, obstruct the view of the location of the ends of the device being manipulated. Additionally, the profile of the present delivery systems is no greater than that of the device being delivered over tube 40 (the larger of the delivery tubes). This is advantageous because the smaller the profile of the delivery system, the less likely the diseased segment of the structure will be unnecessarily disrupted or traumatized during the positioning and delivery of the woven device.

It is possible to overstent anatomical structures utilizing the present delivery systems and present stents through the longitudinal movement of tubes 40 and 22 in both version 1 and version 2, the latter of which is described below. As described above, these tubes may be moved relative to each other such that the stent being delivered is compressed maximally or nearly maximally prior to being released.

If the stent is not in the desired location after reaching its preformed diameter, it can advantageously be restretched and repositioned by moving tube 40, proximally and locking tube 40 to tube 22 if so desired. After locking has occurred, the stent may be repositioned and the process above described may be repeated as needed. This process may be complete when the stent is positioned in the desired location, and the stent fits in the vessel or non-vascular tubular structure in a way that the stent is nearly maximally expanded and/or the tissue of the vessel or non-vascular tubular structure is stretched slightly.

After performing this process, the distal end of the stent may then be released from its secured position. The distal end of the stent may be so released by pulling securing wire 30 (or wires) back into the lumen of tube 22. If the stent is still in the proper position, the proximal end of the stent may be released in the same manner so as to deliver the stent into the vessel or non-vascular structure, and the delivery system may be withdrawn back into a sheath and out of the body. If the stent is no longer positioned in the desired location after releasing the distal end of the stent, the stent may be pulled proximally back into a sheath by proximally moving tube 40 to which the proximal end of stent is still secured and/or distally moving the sheath. After doing so, the stent and delivery system may be removed from the body.

It is to be understood that the proximal end of the stent may be released from its secured position prior to releasing the distal end of the stent. Upon doing so, however, the ability to withdraw the stent back into a sheath (if a sheath is used) as described above is no longer present. Therefore, typically, the proximal end may be released first when the desired location of the stent will likely be maintained after such release.

In version 2, the stretched stent may be positioned in the desired location of the vessel or non-vascular tubular structure to be stented. Then, prior to unlocking the tubes, a sheath used to cover the stent, if used, may be proximally withdrawn so as to expose the stretched stent. Also prior to unlocking the tubes, outer sheath 70 covering inverse tabs 60 may be moved proximally so that inverse tabs 60 are exposed (see FIG. 5A). In an exemplary embodiment, the outer sheath 70 may be withdrawn but not removed. The tubes may then be unlocked. It is to be understood that the tubes may be unlocked prior to withdrawing either a sheath used to cover the stretched stent, or outer sheath 70. Once this has occurred, either the distal end or proximal end of the stent may be released from its secured position as follows. In an exemplary embodiment, it may be preferable to release the distal end of the stent first because the secured proximal end may offer the possibility of removing a misplaced stent as above described. It is to be understood, however, that because of the completely controlled nature of the delivery system of the present invention, the need to remove a misplaced stent may be very low, and, therefore, the proximal end of the stent may be released first without great risk.

When the distal end is to be released first, tube 40 may be moved distally over tube 22 (see FIGS. 5B and C) until the distal end of tube 40 reaches a pre-determined point located on tube 22, which in an exemplary embodiment, may be denoted through the use of a radiopaque marker. The point is located along tube 22 such that the proximal end of the stent will not be unhooked from inverse tabs 60 when the distal end of tube 40 reaches it. When the point is reached by the distal end of tube 40, the tubes are locked together. Additionally, another marker may also be used on the proximal shaft of tube 22 to denote the same point. If the stent is no longer in its ideal position at this point, outer sheath 70 may be moved distally and/or tube 40 may be moved proximally to cover inverse tabs 60, and the delivery system and the stent may be withdrawn into a sheath and removed from the body. If the proper position has been achieved, the distal end of the stent may then be released in the manner above described. Next, the proximal end of the stent may be released by unlocking the tubes, and moving tube 40 distally over tube 22 until inverse tabs 60 release the openings or closed structures through which they were threaded. Tube 40 may then be further advanced distally until inverse tabs 60 are hidden or housed within sheath 52 as shown in FIG. 5D. At this point, the tubes may be locked together to maintain the position of the inverse tabs within sheath 52. After both ends of the stent have been released (see FIG. 5E), delivery system 50 may be withdrawn into a sheath and removed from the body.

Figure 5C:
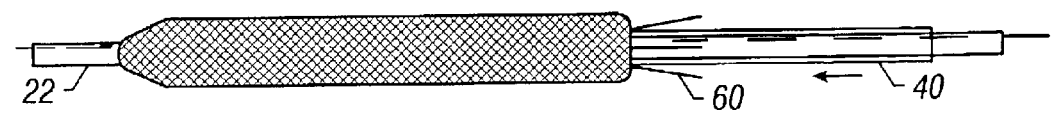

In version 2, if the proximal end of the stent is to be released first, the sequence of events just described may occur (including the ability of the stent to be restretched and repositioned), except that the distal end of tube 40 may extend distally beyond the predetermined point such that inverse tabs 60 unhook the proximal end of the stent and then go on to being hidden or housed within sheath 52 as shown in d. of FIG. 5. After the proximal end has been released, the distal end of the stent may be released in the manner above described. At this point, the tubes may be locked together to maintain the position of the inverse tabs within sheath 52. Delivery system 50 may then be withdrawn from the body as above described.

The delivery of the present stent grafts that utilize graft material that is stretchable as described above may be achieved with the same delivery systems and in the same manner as the delivery of the present "naked" stents. When a graft material that is formed from relatively non-stretchable material, such as PTFE, is utilized, however, although the same delivery systems may be utilized, the manner in which the stent graft may be delivered is slightly different from the manner in which the naked stents may be delivered in terms of the manner in which the stent graft may be repositioned, if necessary.

For example, if after releasing the distal end of the stent graft, whether the graft material is attached to the stent at the proximal or distal end thereof, the stent may be restretched over the delivery tubes and the stent's completely elongated position may be secured using the proximal lock mechanism. Then, the introducer sheath may be advanced over the proximal end of the stent graft, possibly as it is rotated, in order to recapture the graft material and the stent itself. Attaching the graft material to the stent at the proximal end thereof may make it easier to re-sheath the graft material using the process just described, and thus may facilitate repositioning, if necessary, because the graft material may take on a funnel shape prior to the release of the proximal end of the stent graft.

Delivery of Stents in Side-by-Side Relationship

Figure 26:
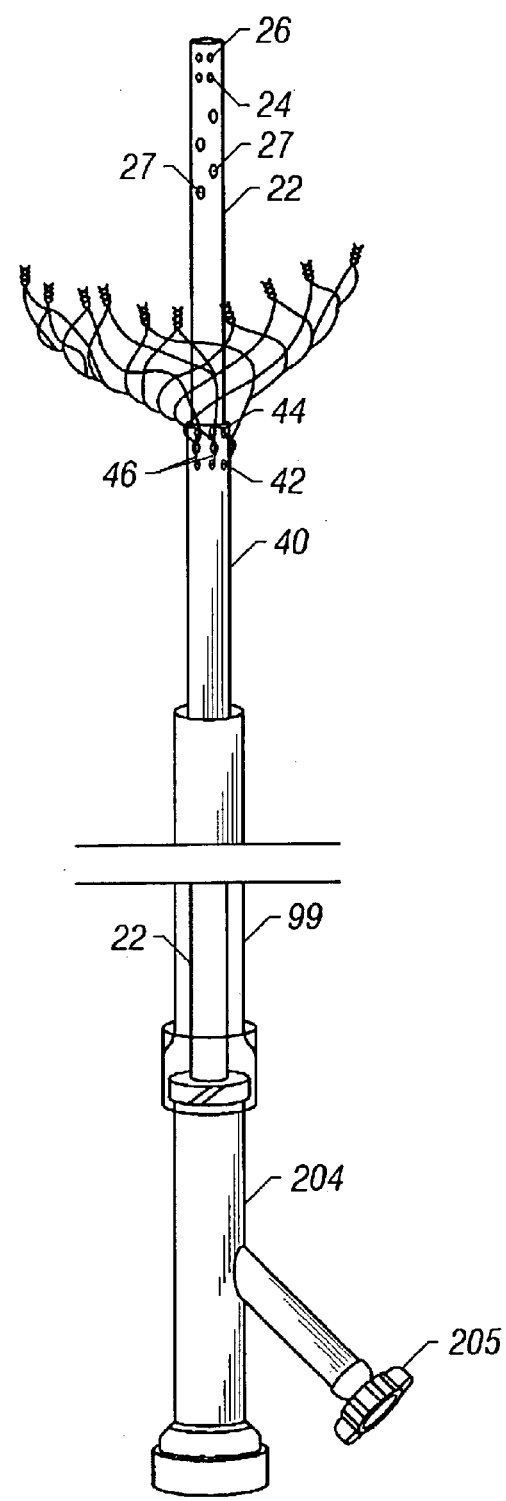
FIG. 26 is a front view of a delivery system for a temporary filter according to one embodiment of the present invention.
Figure 58A:
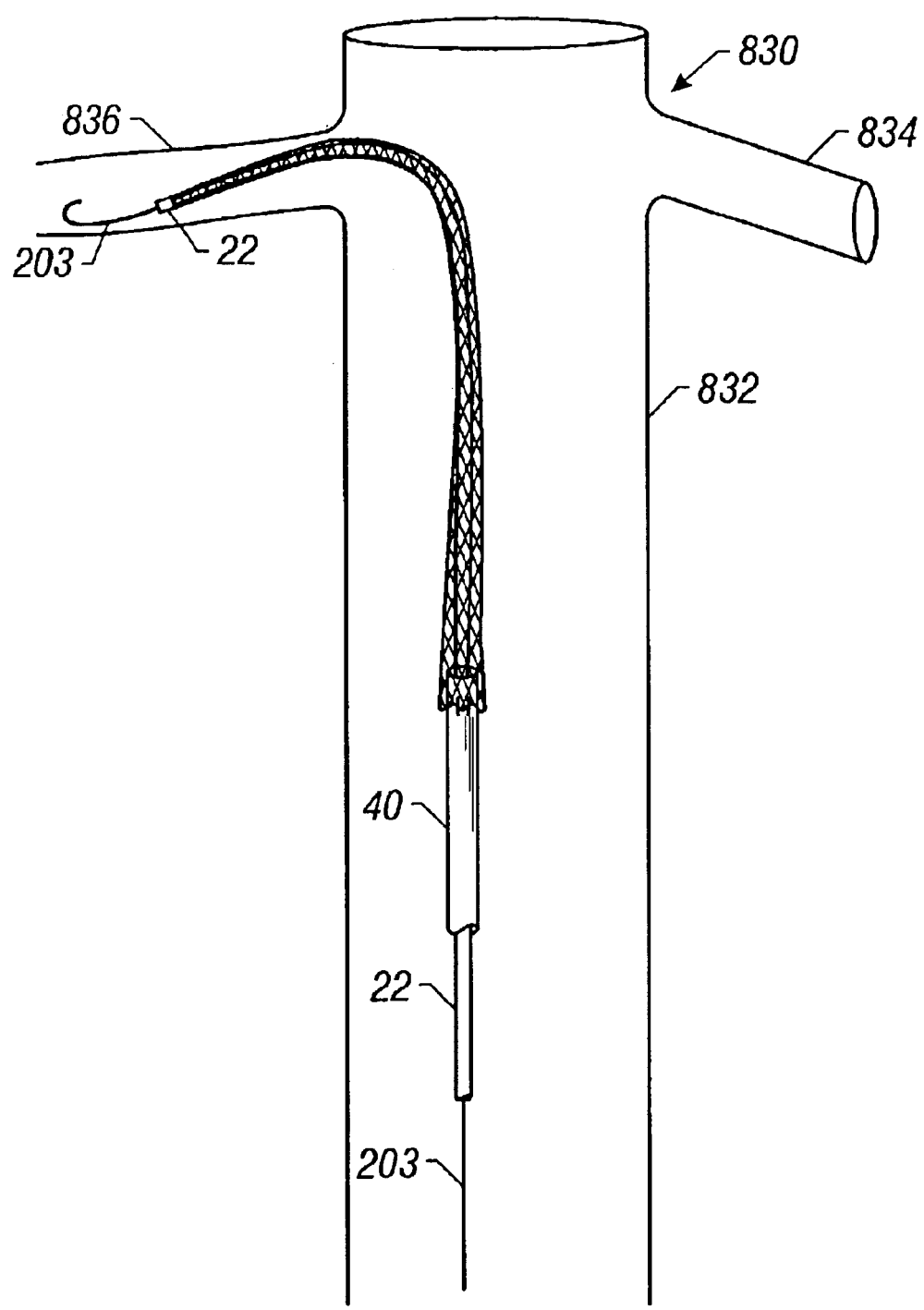
FIGS. 58A–D show stages in the delivery of one stent of a pair of stents in the aorto-renal junction according to one embodiment of the present invention.
Figure 58B:
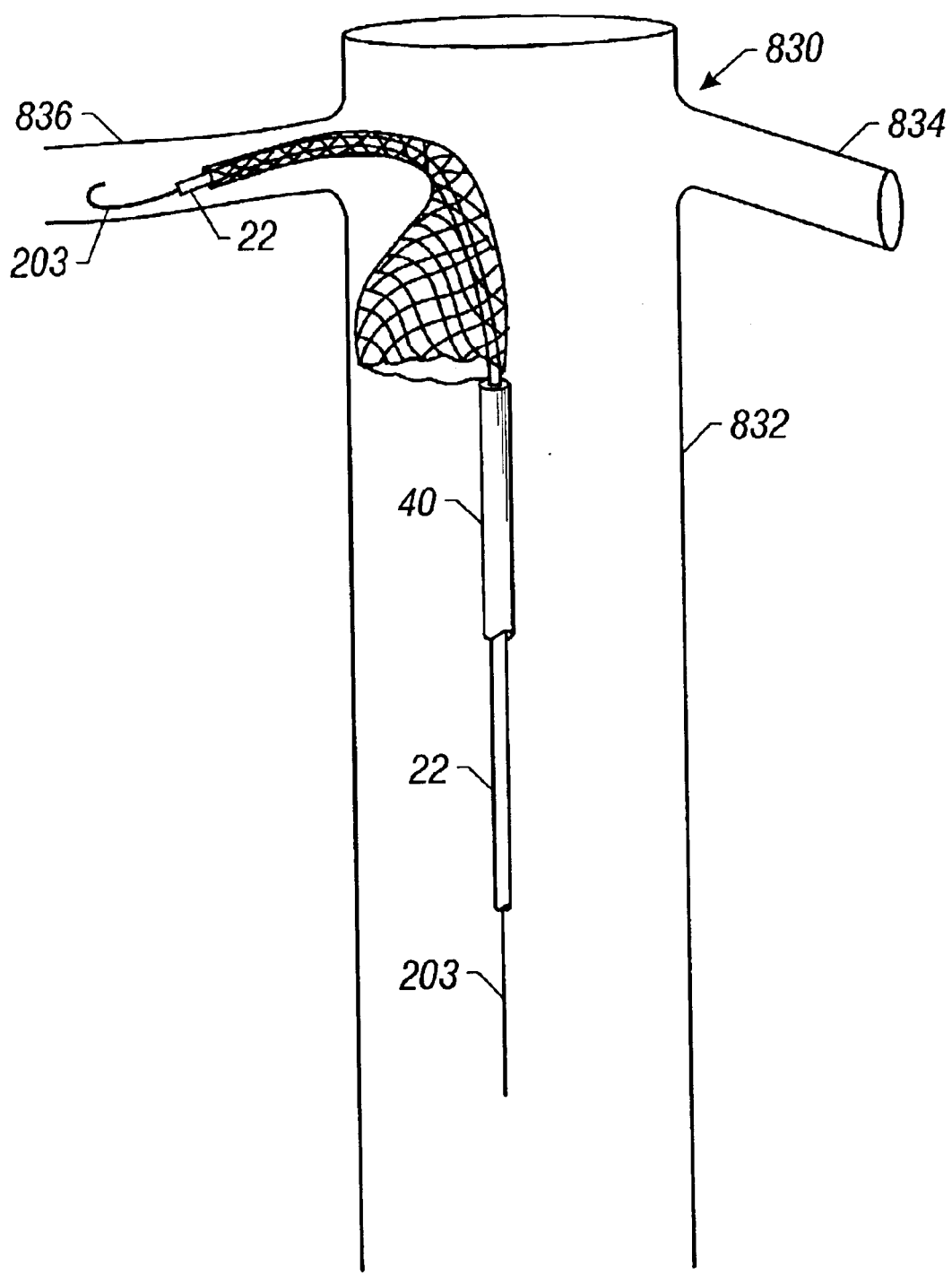
Figure 58C:
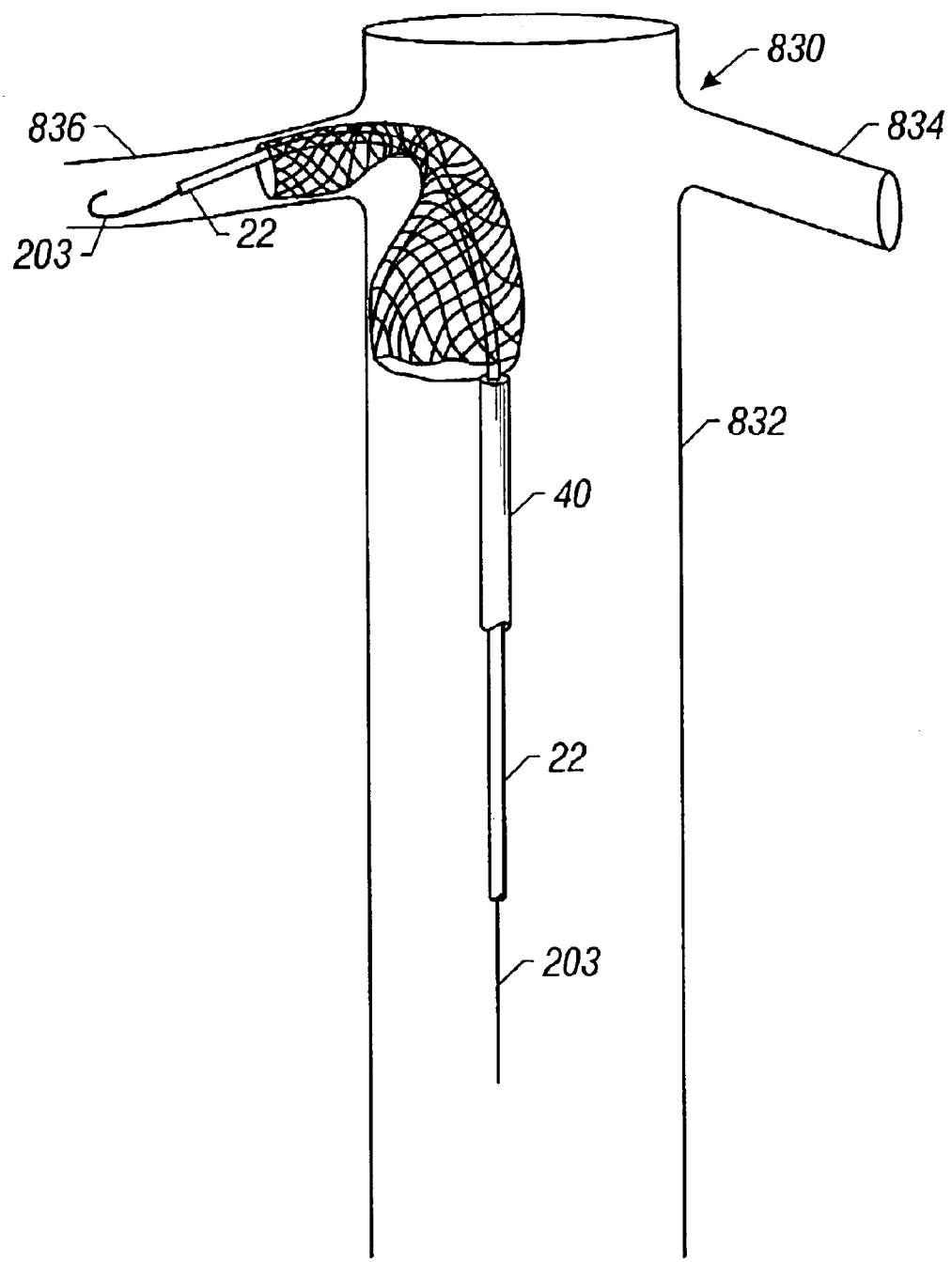
Figure 58D:
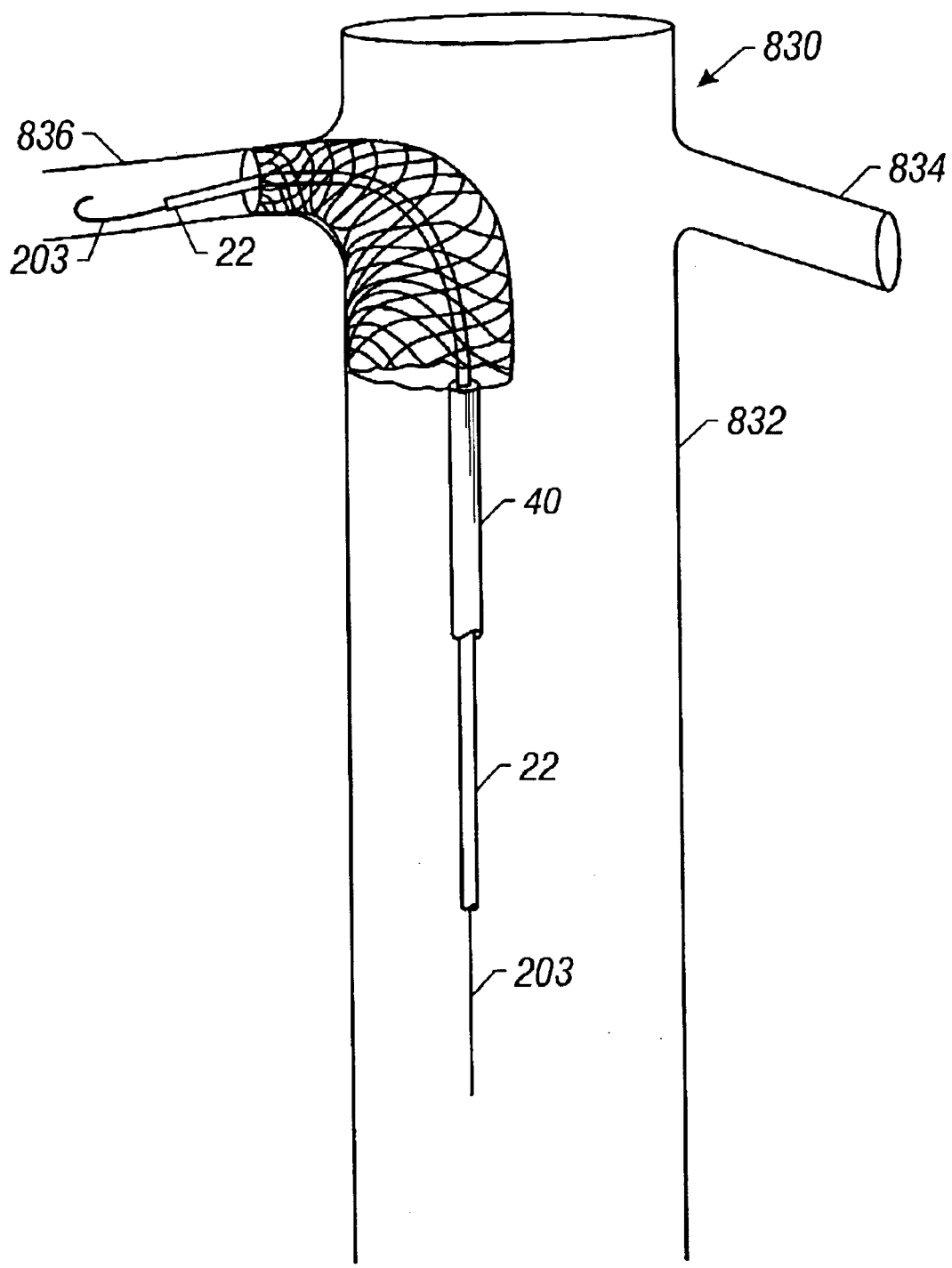

The delivery of these stents may be accomplished relatively simultaneously, such that neither stent occupies more space within the aorta than does the other. Initially, the stents may be secured to either version of the delivery systems described above using the methods described above. As illustrated in FIGS. 58A–D, in addition to securing the ends of the stent to tubes 22 and 40, the stent may also be secured to either tube (tube 22 as shown, for example) near the portion of the stent that will be positioned near the bilateral aorto-renal junction 830, which consists of aorta 832, left renal artery 834 and right renal artery 836. FIGS. 58A–D illustrate only one stent being delivered, but it will be understood to those of skill in the art, with the benefit of this disclosure, that, as stated above, two stents may be released and delivered relatively simultaneously in the fashion described below. As shown, guidewire 203 may be utilized to enhance the maneuverability of the delivery system. (The fittings that may be used to secure tubes 22 and 40 to each, which are illustrated in FIGS. 25 and 26, are not illustrated in FIGS. 58A–D for the sake of simplicity.) This third secured portion may be achieved using the low-profile, tight securing loops described above. After stretching the stent on the delivery system and positioning the distal end of the stent in right renal artery 836 in the manner described above (FIG. 58A), the release and delivery of the stent may take place by first releasing the proximal end of the stent (FIG. 58B), then the distal end (FIG. 58C), and finally the portion of the stent near junction 830 (FIG. 58D). Tubes 22 and 40 and guidewire 203 may then be withdrawn from the patient. It will be understood to those of skill in the art, with the benefit of this disclosure, that the release of the various secured portions of the stents may take place in any order suited to the anatomical structure in question.

Combined Treatment of Aneurysms Consisting of Stent Placement and Transcatheter Embolization In one embodiment of the present invention, the straight stent may be used for aneurysm treatment without being equipped with a graft material. In this embodiment, the "naked" stent may serve as a scaffold for developing an endothelial layer on the newly formed vessel lumen, while the aneurysmal sac may be excluded from circulation by transcatheter embolization.

Figure 36:
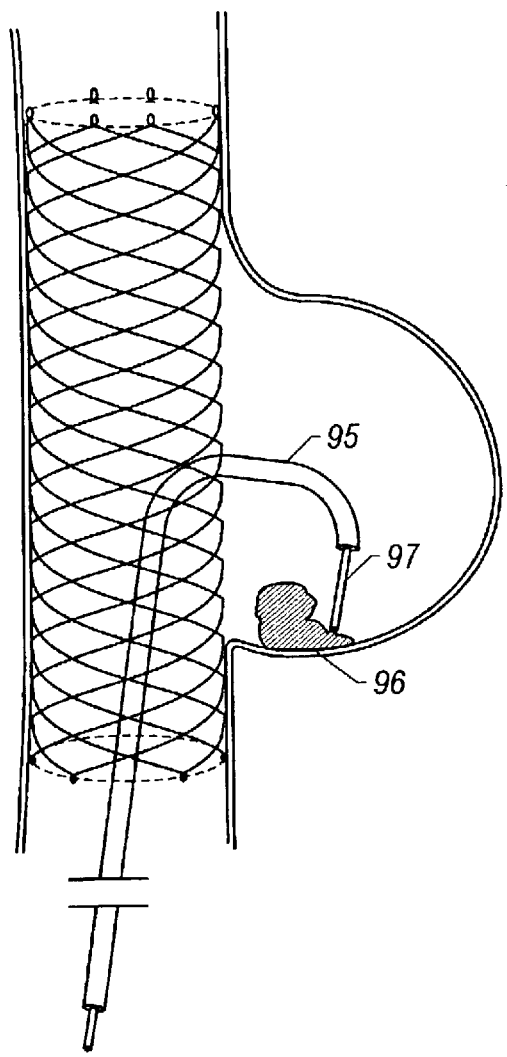
FIG. 36 is a front view of an aneurysm being treated by transcatheter embolization according to one embodiment of the present invention.

Generally, the stent may be delivered into place, and an embolic agent 96 may be inserted into the surrounding aneurysmal sac as shown in FIG. 36.

As shown in FIG. 36, once the stent is in the appropriate position, an angiographic catheter 95 (5-French to 7-French) that is chemically compatible with the embolic agent (and not made from polyurethane when the embolic agent contains DMSO) may be inserted and advanced into the lumen of the stent. In advancing the angiographic catheter into the lumen of the stent, one may use the same guidewire which may have been used in delivering the stent. However, one may advance the angiographic catheter without the use of a guidewire. An adequately sized microcatheter 97 (2-French to 4-French) that is also chemically compatible with the embolic agent may then be advanced through the angiographic catheter, on an appropriate size guidewire (0.014-inches to 0.025-inches). The tip of the microcatheter may then be led through the weave of the stent into the aneurysmal sac. If the openings in the weave of the stent are approximately 2.0 to 2.5 mm, angiographic catheter 95 may also be advanced into the aneurysmal sac. An embolic agent 96 may then be inserted into the aneurysmal sac through the microcatheter. Embolic agent 96 may be chosen so as to be: non-toxic, non-irritant/reactive to the tissues; easily handled; suitable for continuous injection; adequately radiopaque; capable of filling the space contiguously without leaving unoccupied spaces; and non-fragmented, thereby not getting back through the stent's weave into the newly formed lumen which could result in peripheral embolization.

Although, several fluid embolic materials (alcohol, polyvinyl alcohol, cyanoacrylates, Ethibloc etc.,) are available for transcatheter vessel occlusion, none of them is considered ideal or even suitable for this purpose. Recently, a nonadhesive, liquid embolic agent, ethylene vinyl alcohol copolymer (EVAL), has been used clinically for treatment of cerebral AVMs in Japan (Taki, AJNR 1990; Terada, J Neurosurg 1991). The co-polymer was used with metrizamide to make the mixture radiopaque and may serve as the embolic agent for the present invention.

Very recently, a new embolic agent (similar to EVAL), EMBOLYX E (ethylene vinyl alcohol copolymer) (MicroTherapeutics Inc., San Clemente, Calif.) was developed which was designed for aneurysm treatment (Murayama, Neurosurgery 1998), and may be utilized as an embolic agent in one embodiment of the present invention. The embolic agent is composed of a random mixture of two subunits, ethylene (hydrophobic) and vinyl alcohol (hydrophilic). Micronized tantalum powder is added to it to obtain an appropriate radiopacity, and DMSO (di-methyl sulfoxide) is used as an organic solvent. When the polymer contacts aqueous media, such as blood, the solvent should rapidly diffuse away from the mixture causing in situ precipitation and solidification of the polymer, with formation of a spongy embolus and without adhesion to the vascular wall. Any kind of material with characteristics similar to those of EMBOLYX E may be used as an embolic agent for the present invention.

The method just described may be utilized when the stent is covered as well. In such an embodiment, angiographic catheter 95, which may be 5-F in size, and microcatheter 97, which may be 3-F in size, may advanced into the lumen of the covered stent as described above. A trocar, such as one having a 0.018-inch pencil-point or diamond-shaped tip and made of any suitable material such as stainless steel or nitinol, may then be inserted into the lumen of microcatheter 97. The sharp tip of the trocar may extend beyond the tip of microcatheter 97 by about 2 to 4 mm. The proximal ends of microcatheter 97 and the trocar may be locked together using a Luer lock mechanism. By doing so, a sheath-needle unit (well known in the art) may be created, which may then be used to puncture the graft material and the stent mesh. Thereafter, using fluoroscopy and/or CT in guiding the sheath-needle unit, the sheath-needle unit may be safely advanced into the aneurysmal sac. The trocar may then be removed, and microcatheter 97 may be used for injecting the embolic agent as described earlier.

Both abdominal and thoracic abdominal aneurysms may be treated as above described. In some other locations (e.g., external iliac artery), pesudoaneurysm and/or tumor-induced corrosive hemorrhage may also be treated as above described.

The size of the delivery system that may be used to deliver a stent without a graft cover may be sufficiently small, such that insertion of the stent into the vessel may take place following a percutaneous insertion. The delivery system would also be well-suited to negotiating through tortuous vascular anatomy. The treatment described above may be performed using interventional radiology techniques, thereby eliminating the need for surgery. The embolization may occlude the lumbar arteries from which the excluded aneurysmal sac is frequently refilled. As a result of using the treatment described above, the endoleak from the patent lumbar arteries may be eliminated.

2. Filters

Low-Profile Woven Cava Filters

The wires of the cava filters of the present invention may be made of the same materials as the wires of the stents. The same number of wires may be used in forming the cava filters as are used to form the stents. However, in an exemplary embodiment, less wires are preferably used for the cava filters than for the stents. As with the stents, in an exemplary embodiment, as few as 5 wires may be used to form the cava filters for any given application except the single wire embodiment, which utilizes only one wire.

The cava filters may be created with a relatively loose weave allowing the blood to flow freely. In an exemplary embodiment, it is preferable that the distal end of the cava filters is not completely closed. See FIGS. 6–8. Instead, the bent ends of the wires (FIG. 7 and FIG. 8 show small closed loops, but bends may also be used) or the coupled ends of the wires (FIG. 6) are arranged to form a relatively round opening with a diameter of about 2 to 5 mm. The size of the wires that may be used for forming the cava filters other than the barbless stent filter (discussed below) ranges from between about 0.009 inches and about 0.013 inches, but is most typically about 0.011 inches. The size of the wires that may be used for forming the barbless stent filter ranges from between about 0.008 inches and about 0.015 inches, but is most typically about 0.011 inches.

As with the stents of the present invention, the angle between the crossing wires of the cava filters is preferably obtuse. Similarly, at the proximal end (e.g., FIG. 6) of the filter, either a loop or bend may be formed by bending the wires as above described. When such closed structures are made at the distal end of the filters, the angle formed may be acute as shown in FIGS. 7, 8 and 9A. At the distal (e.g., FIG. 6) or proximal end (e.g., FIG. 7 and FIG. 8) of the cava filters, the wire ends may be coupled together to form closed structures as above described.

Figure 59:
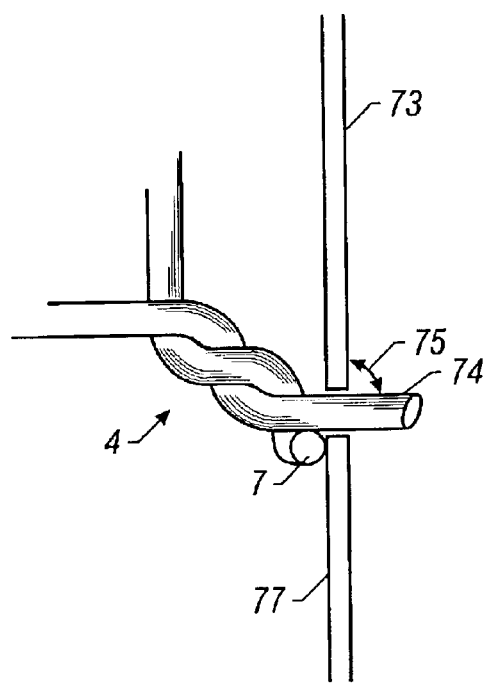
FIG. 59 is a front view of a barb (of a filter) that is penetrating a vessel wall according to one embodiment of the present invention.

Advantageously, the portions of the wires forming the closed structures may be bent outwardly into multiple barbs to anchor the filter, when located at the proximal ends of the cava filters (e.g., FIG. 7 and FIG. 8). As used herein, "barbs" are portions of the ends of the wires that may be used to form the cava filter. By carefully selecting the size, orientation and shape of the barbs, they may penetrate the vessel wall in order to better anchor the filter during use, but they may also be disengaged from the vessel wall as the filter is being retrieved but prior to the filter being withdrawn such that the possibility of causing any damage to the vessel wall is minimal. As illustrated in FIG. 59, barb 74 of closed structure 4 is penetrating vessel wall 73 at an angle 75 that is acute. Although angle 75 may be obtuse, the inventors have found that barb 74 generally anchors the filters more securely when angle 75 is acute rather than when it is obtuse. Beginning at side 77 of vessel wall 73 and extending to the end of barb 74, barb 74 may be about 1 to 2 mm long. As shown, wire end 7 may be oriented at an angle that is roughly perpendicular to the angle of barb 74 such that barb 74 is prevented from more deeply penetrating vessel wall 73. Another example of suitably shaped barbs may also be found on the RECOVERY filter, which is commercially available from C. R. Bard, Inc. (www.crbard.com; Murray Hill, N.J., 800 367–2273).

Figure 51:
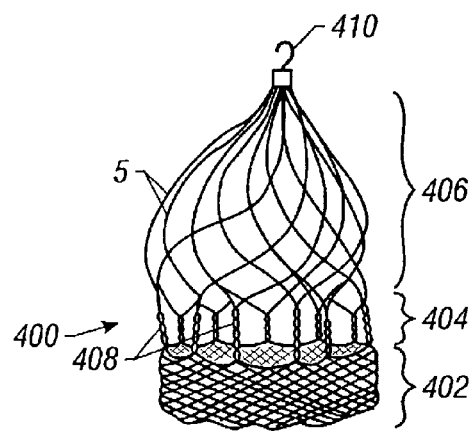
FIG. 51 is a perspective view of a barbless stent filter according to one embodiment of the present invention.

The cava filters of the present invention may be formed by plain weave using the methods described above for forming the stents. Of course, an appropriately shaped template may be chosen. Shapes for the cava filters include a cone (FIG. 6 and FIG. 7), a dome (FIG. 8), an hourglass shape (FIG. 9), and the shape of the barbless stent filter (FIG. 51). The cava filters may also be heated as the stents are, and may be allowed to cool as the stents are. Additionally, in an exemplary embodiment, as with the tapered stent, the filters may be woven on a cylindrical template, heated and allowed to cool, then the body formed may be remodeled and then reheated on another template. In an exemplary embodiment of the hourglass filter, for example, the body formed by weaving may be heated and cooled, and then may be remodeled into the shape of an hourglass by narrowing the central portion using a material suitable for reheating such as copper/brass wire; then the hourglass shaped body may be reheated.

In an exemplary embodiment of the cava filters of the present invention, it may be preferable to flare and compress the woven structure near the proximal end of a conical or dome shape filter or near both the proximal and distal ends of an hourglass filter, forming a cylindrical portion with a relatively tight weave (see portions 140 in FIG. 6, FIG. 7 and FIG. 9) prior to heating. The diameter over this portion may be virtually constant. In an exemplary embodiment, this portion may be formed using the above-described method of heating and cooling a filter that may not possess the desired portion, reconstraining or remodeling the filter to achieve the desired shape of the portion, securing the given portion of the filter in the desired shape and heating and cooling the constrained filter again.

In an exemplary embodiment, this constant-diameter portion and/or the flared ends of the cava filters may be advantageously used for anchoring. By achieving strong contact between the filter and the vessel wall, the filter's intraluminal position can be further secured. The expansile force of the cava filter (which depends partly on the number and size of the wires which are used for making the structure) may be chosen so as to ensure such strong contact. The use of the flared portions as well as the suitable barbs may virtually eliminate the possibility of migration.

The cava filters of the present invention will be further described in more detail below by the way of specific examples.

a. Conical Filter—FIGS. 6 and 7

With reference to the illustrative embodiments shown in FIGS. 6 and 7, there are shown conical filters for insertion and delivery into vascular anatomical structures. The conical filters include a plurality of wires which may be arranged in a plain weave as described above so as to define an elastically deformable body 150. As shown in FIGS. 6 and 7, body 150 has a wide and/or flared proximal end 142 and a distal end 144. The diameter of body 150 is larger at proximal end 142 than at distal end 144. The diameter of body 150 decreases from proximal end 142 to distal end 144. Distal end 144 may be formed in such a way that almost no opening is left through which fluid might flow. As discussed above, however, in an exemplary embodiment, it is preferable to leave a relatively round opening with a diameter of about 2 to 5 mm.

b. Dome Filter—FIG. 8

With reference to the illustrative embodiment shown in FIG. 8, there is shown a dome filter for insertion and delivery into a vascular anatomical structure. The dome filter includes a plurality of wires which may be arranged in a plain weave as described above so as to define an elastically deformable body 152. As shown in FIG. 8, body 152 like body 150, may have a wide and/or flared proximal end 142 and a distal end 144. The diameter of body 150 is larger at proximal end 142 than at distal end 144. The diameter of body 150 decreases from proximal end 142 to distal end 144. The degree of the decrease in the diameter from the proximal to the distal end is not as steep as in the conical version, however. As a result, body 152 more resembles a hemisphere than a cone. Because of its hemispherical shape, the dome filter may occupy less longitudinal space within the cava than other filters.

c. Hourglass Filter—FIG. 9

With reference to the illustrative embodiment shown in FIG. 9, there is shown an hourglass filter for insertion and delivery into a vascular anatomical structure. The hourglass filter includes a plurality of wires which may be arranged in a plain weave as described above so as to define an elastically deformable body 154. As shown in FIG. 9, body 154 has two conical or dome portions 146 bridged by a narrow portion 148. The diameter of distal and proximal ends 144 and 142 is larger than the diameter of portion 148. In an exemplary embodiment, distal end 144 is preferably not equipped with barbs. The closed structures of proximal end 142 may be bent outwardly to form barbs. The lumen size of narrow portion 148 may be selected so as not to close the lumen of the filter completely. The hourglass filter shown in FIG. 9 has multiple filtrating levels; in an exemplary embodiment there may be almost no difference in the filtrating capacity between the filtrating capacity of the center of the filter and the filtrating capacity of the periphery of the filter because the blood may be filtered by the peripheral weave of both the proximal and distal portions 146. FIG. 10 shows an hourglass filter placed in the IVC.

d. Barbless Stent Filter—FIG. 51

With reference to the illustrative embodiment shown in FIG. 51, there is shown a barbless stent filter for insertion and delivery into a vascular anatomical structure. The barbless stent filter includes a plurality of wires which may be arranged in a plain weave as described above so as to define body 400, which, like all the other bodies in this disclosure, is suitable for implantation into an anatomical structure. As shown in FIG. 51, body 400 may consist of base 402, mid-portion 404, and dome 406.

Base 402 may be made as a straight stent (as described above) with a given diameter. As a result, base 402 may serve to anchor the filter within a vessel and may not participate in blood filtration. In another embodiment of this filter, base 402 may also be made with a changing diameter. For example, its lumen may be slightly tapered from base 402 to mid-portion 404. The mesh tightness of base 402 may approach the maximum-achievable tightness (i.e., 180°). Accordingly, the radial force of the anchoring portion (base 402) will increase as the mesh tightness increases.

Additionally, by carefully selecting the diameter of base 402, body 400 may be configured to retain its position within a vessel without the use of barbs. As a result, the task of carefully selecting the size, orientation, and shape of the barbs that could otherwise be used such that those barbs may be elevated from the caval wall so as to greatly reduce the possibility of damaging the vessel wall during resheathing (as a result of repositioning or removing the filter) may be eliminated. In an exemplary embodiment of the barbless stent filter, the diameter of base 402 may be 26–30 mm, which represents operable diameters in ninety-five percent of the population, which has an inferior vena cava of less than 28 mm in diameter. In an exemplary embodiment of the barbless stent filter, the length of base 402 may not exceed 10–15 mm.

As shown in FIG. 51, mid-portion 404 of the barbless stent filter includes struts 408, which are formed of twisted wires 5. Struts 408 are arranged so as to be oriented in substantially parallel relationship with the axis of the portion or segment of the vessel in which they are delivered or released. Struts 408 may serve to further stabilize the barbless stent filter within the vessel or non-vascular structure into which the filter is delivered. For example, in the embodiment of the barbless stent filter shown in FIG. 52, struts 408 may be slightly bent or bowed outward so as to increase the frictional forces between the delivered filter and the vessel wall. As a result, the self-anchoring capability of the filter may be increased. In an exemplary embodiment of the barbless stent filter, the length of mid-portion 404 may be about 5–10 mm.

Turning to the third portion of the barbless stent filter, as shown in FIG. 51, the mesh tightness of dome 406 may be loose. In one embodiment of this filter, the top portion of the dome may be equipped with hook 410 to facilitate the removal of the filter. In such an embodiment, hook 410 may be small and made of metal or any other suitable material, and may be firmly and permanently attached to wires 5. Similarly, although not illustrated, with the benefit of the present disclosure one of ordinary skill in the art will understand that hook 410 may also be provided on the proximal ends of the other cava filters disclosed herein. Additionally, the hooks on these filters may be used during the possible repositioning or retrieval of such filters in the same way as may be used on the barbless stent filter, described below in greater detail.

In another embodiment, the barbless filter may be provided with two filtration levels. As shown in FIG. 53, such a filter is composed of two domes 406 (arranged inversely), a mid-portion 404 having a tight stent mesh similar to the mesh of base 402 in the embodiments in FIGS. 51 and 52, and two, intermediate segments 412 having short, struts 408 between domes 406 and mid-portion 404. In one version of this embodiment, both the top and bottom portions of the domes may be equipped with hook 410 to facilitate the removal of the filter. Alternatively, either the top or bottom may be equipped with hook 410.

Figure 52:
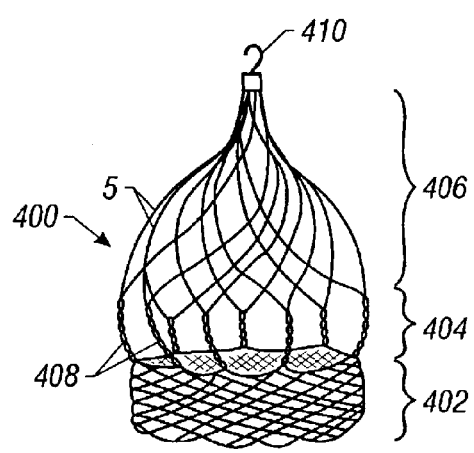
FIG. 52 is a perspective view of a barbless stent filter having bent longitudinal segments according to one embodiment of the present invention.
Figure 53:
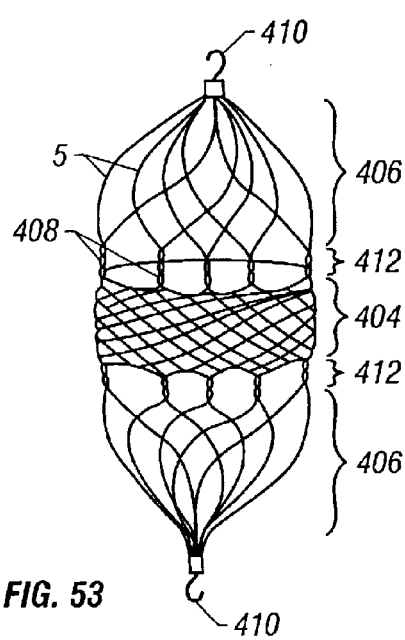
FIG. 53 is a perspective view of a barbless stent filter having two filtrating levels according to one embodiment of the present invention.

The end of the barbless stent filters located proximate hook 410 depicted in FIGS. 51–53 may be positioned so as to achieve a variety of configurations. For example, the end may be stretched such that the shape of domes 406 is closer to a triangle than the shape depicted in FIGS. 51–53, or the end may be compressed.

The shape of the barbless stent filters may be formed using the methods described above for forming the stents and other cava filters. For example, the barbless stent filter may be woven on an appropriately shaped template. Then the filter and template may be heated and cooled as above described. Alternatively, the barbless stent filter may be woven on a cylindrical template and heated and allowed to cool. Alternatively, prior to heating and cooling, certain portions such as the mid-portion and dome may be reconstrained or remodeled, and the remodeled portion of the filter may then be secured and heated and cooled again.

e. Biodegradable Filters

As indicated above, all of the filters of the present invention (including the BI filter discussed below) may be formed with filaments made of biodegradable material so as to form self-expanding, self-anchoring, bioabsorbable, biodegradable filters that may, in addition to functioning as filters, function as drug or nutrient delivery systems as a result of the material used. In one embodiment, the biodegradable filters of the present invention may be provided with reinforcement wires as above described.

The factors that may be considered in choosing the materials from which to form the biodegradable stents, the materials themselves, the methods of forming the biodegradable stents and reinforcing the stents with wires, apply to the filters as well. In addition, one may also consider the following: the flow conditions of the vessel into the biodegradable filters are placed (e.g., high flow conditions within the vena cava), to better ensure that the material and weave of the filter are chosen such that the filter may anchor properly within the vessel; the rate of degradation of the chosen material as well as the time at which the degradation will begin so that if the filter is used as a temporary filter (as described below), the entrapped thrombi may be attended to before the filter degrades to an extent that the entrapped thrombi could be released back into the bloodstream.

Any of the cava filter embodiments disclosed herein may be made from both wires 5, (wires 5 may be made from any of the materials described above, such as nitinol) and appropriate biodegradable filaments 540. Although the barbless stent filter is described below in this regard, it is by way of example only, and with the benefit of the present disclosure, one having skill in the art will understand that wires 5 and biodegradable filaments 540 may be connected to each other as hereinafter described for the other embodiments of the cava filters disclosed herein.

Base 402 may be formed from wires 5, while dome 406 may be formed from filaments 504, which may be formed from an appropriate biodegradable material, such as one described above in greater detail. In this embodiment, the transition between the two materials may be created in mid-portion 404. The connection between each nitinol wire and the corresponding filament may be made by using any suitable means such as glue, heat, by wrapping the filament around the wire, or any combination of thereof. After biodegradation of dome 406 has taken place, base 402 may, like a self-expanding stent, be left behind in the body.

f. Single-Wire Embodiment Filter

Figure 15:
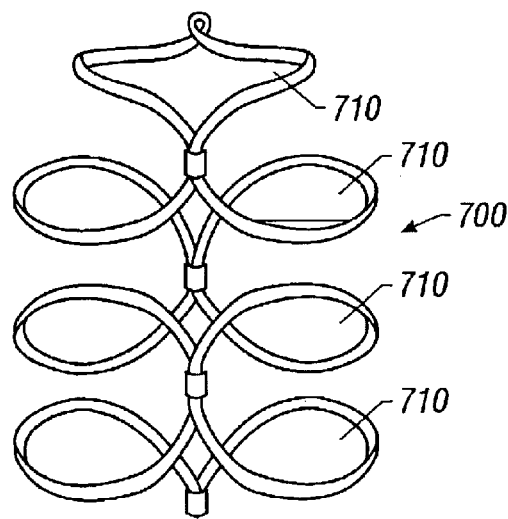
FIG. 15 is a perspective view of a single wire embodiment filter according to one embodiment of the present invention.
Figure 60:
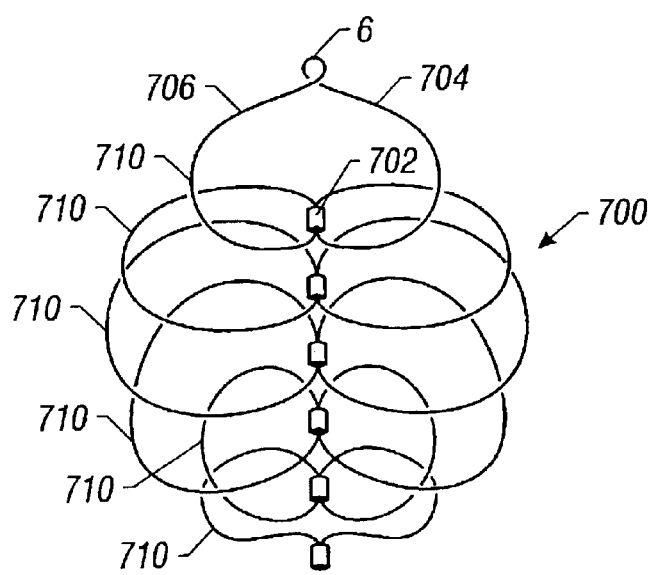
FIG. 60 is a perspective view of a single wire embodiment filter according to another embodiment of the present invention.

As with the occluders, the single wire embodiment may also be utilized as a structure for filtering thrombi within a vessel. The single wire embodiment filters may be formed in the same manner as the single wire embodiment occluders are formed. Moreover, the single wire embodiment filters are simply the single wire embodiment occluders without any thrombogenic agents attached to the body of the single wire embodiment filters. In this regard, FIG. 60 illustrates body 700 of a single wire embodiment filter. The body has first segment 704 and second segment 706 separated by a bend in the wire that is in the form of closed loop 6. The body is provided with multiple collars 702, which hide multiple loop-defining locations where the segments are positioned adjacent to each other. (Adjacent has the same meaning with respect to the single wire embodiment filters as it has with respect to the single wire embodiment occluders.) The segments 704 and 706 extend between the loop-defining locations so as to form multiple loops 710, which are designated in FIG. 60 by the segments that outline them. Another embodiment of the present single wire filters is illustrated in FIG. 15. As illustrated in both FIGS. 60 and 15, loops 710 of bodies 700 possess compressed shapes.

Delivery System of the Cava Filters

Version 1 shown in FIG. 3 may be used as the delivery system for the cava filters (including each of the versions described above) according to the present invention.

Delivery of the Cava Filters

Figure 28:
FIG. 28 is a front view of a conical filter in a fully stretched position according to one embodiment of the present invention.

Prior to insertion and delivery, a cava filter in the form of a body 150, 152, 154, 400 (or biodegradable versions thereof), or body 700 may be manually secured to tubes 22 and 40 of version 1 as above described. The cava filter may then be stretched as described above so as to reduce the diameter of its largest portion by an amount appropriate such that the filter may be inserted into a vessel (preferably with the use of an access sheath), and may pass through the lumen of the vessel as the filter is being positioned prior to being delivered into the vessel. FIG. 28 shows a filter secured to a delivery system in a completely stretched state.

In one embodiment of the method for delivering the cava filters of the present invention, a hollow covering such as a guiding sheath may be placed over the filter secured to the delivery system to prevent contact between the filter and the vessel wall as the filter is inserted and positioned for delivery. In another embodiment, a short, introducer sheath with a check-flo adapter may be used at the access site to prevent contact between the filter and the vessel into which the filter may be inserted during insertion of the filter; in such an embodiment the introducer sheath may or may not be used to cover the filter beyond the access site of the vessel.

The cava filters of the present invention may be stretched completely on the delivery system, reducing their diameters as much as possible, as shown in FIG. 28, for example. In one embodiment, after being secured to the delivery system and stretched to some extent, a filter may be delivered into the inferior vena cava ("UVC"). In such an embodiment, the filter may be inserted into either the right or the left femoral vein, allowing for a femoral approach. In such an embodiment, the filter may be inserted into the internal jugular vein, allowing for a jugular approach. In such an embodiment, a filter and delivery system with a relatively small profile, such as 7-F, for example, may be inserted into a peripheral vein (pl. antecubital vein), allowing for a peripheral approach, if the system is sufficiently flexible. As discussed above with regard to the delivery of the stents, the construction of the delivery system enables one to use a guidewire in the lumen of tube 22 for delivery of the filter, in an exemplary embodiment of the present invention. It is to be understood however, that a guidewire may not be utilized at times.

Each of the cava filters may be delivered into place in the manner described above with regard to the delivery of the stents using version 1 (see, Delivery of the Stents). All the advantages described above with regard to repositionability, etc., including the advantage of being able to compress the filter being delivered and achieve as tight a mesh in the cylindrical portions thereof (such as base 402 of the barbless stent filter) as possible, apply equally to the delivery of the cava filters. Further, in instances in which one of the present cava filters is delivered in the IVC, for example, the elasticity of the IVC wall allows the operator to achieve an even tighter mesh than the mesh originally created after the annealing process. That is, a filter configured with an angle a of 155° may be compressed during delivery until angle a is 170°, and, if the filter is properly oversized, the elasticity of the IVC wall may maintain angle a at very close or equal to 170°. The ability of the present delivery system to achieve this scenario is especially advantageous when the filter is created without barbs so as to maintain its position within the vessel into which it may be delivered by virtue of the radial force between the filter and the vessel wall.

The weave of the present filters (including those discussed below) is especially suitable to advantageously allow mechanical thrombus-suction to remove the entrapped clots without the risk of dislodging the thrombi and allowing them to travel to the systemic and pulmonary circulation. In so doing, an adequately sized catheter with a large lumen may be inserted into the filter's lumen and used to suck the thrombi out. This method may be used in combination with thrombolysis.

a. Non-Permanent Cava Filter Applications

All of the woven cava filters, particularly the conical, dome, and barbless stent filters, may be used in temporary applications. A basic need exists to remove entrapped thrombi safely and successfully before removal of a temporary filter. The emboli entrapped by any kind of temporary filter can be dealt with in a variety of ways, such as thrombolysis, placement of a permanent filter, or allowing small thrombi to embolize to the lungs. The woven structure of the cava filters of the present invention seems favorable to prevent escape of the entrapped clots during thrombolysis. As a result, there is probably no need to place another filter above the woven temporary filter. This would otherwise be impossible if the temporary filter is delivered from a jugular approach. The temporary applications of the cava filters include both temporary and retrievable filter designs.

Temporary filters may be attached to a catheter or sheath, a tube or a guidewire that may project from the insertion site (e.g., using a hub with a cap which is sutured to the skin for fixation), so as to allow for easy removal of the filter. Retrievable filters are permanent filters that have a potential to be removed.

Both the temporary and the retrievable filters may be delivered via a jugular approach. It is to be understood, however, that these filters may also be delivered via a femoral or antecubital approach.

In one embodiment, a temporary filter may be created by manually securing a cava filter to two tubes in the manner described above. The outer tube to which the proximal end of the filter may be secured may comprise a catheter or sheath, or it may comprise a tube such as tube 40 described above. Being a low profile design, the temporary filter typically does not require an outer tube larger than 7 French.

Figures 27A, 27B:
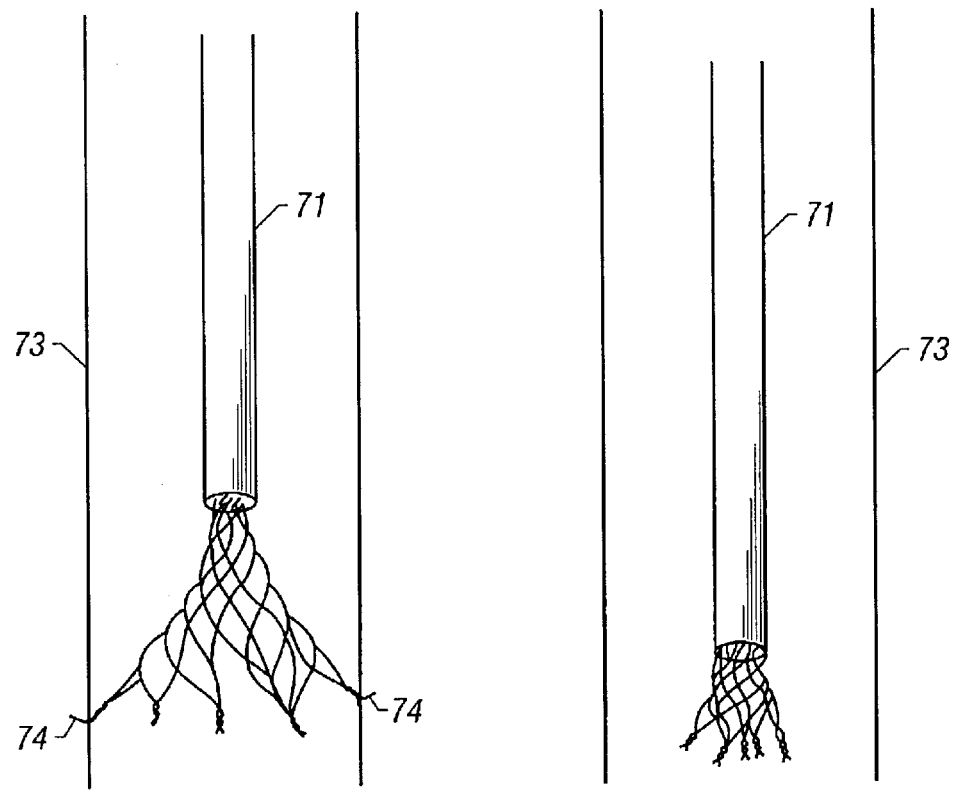
FIGS. 27A and B illustrate stages in the removal of a filter from a vessel according to one embodiment of the present invention.

After properly positioning the temporary filter, the distal end of the temporary filter may be released using the above described method. If the temporary filter is no longer in the proper position, the filter may be withdrawn as shown in FIGS. 27A and B. FIGS. 27A and B illustrate tube 71 (which may, for example, be any suitably-sized catheter or sheath) being advanced over a filter such that barbs 74 of the filter that penetrate vessel wall 73 are disengaged from vessel wall 73 as tube 71 is advanced and the filter is held stationary. A monofilament (not shown) may be threaded through one or more of the bends or closed loops defining the proximal end of the filter. Both ends of the monofilament may be positioned in an easily accessible location (such as exterior of the patient). The operator can then advance tube 71 over the ends of the monofilament (as described below with respect to monofilament loop 172 depicted in FIG. 12) while holding the monofilament steady to disengage barbs 74 from vessel wall 73 prior to the withdrawal of the filter.

After releasing the distal end of the filter, the holes in the superelastic tubing through which the securing wire or wires were threaded may be used for injection of some urokinase or tissue plasminogen activator (TPA) to lyse entrapped thrombi within the mesh. FIG. 26 depicts the situation in which the distal end of the filter has been released. As shown in FIG. 26, openings 27 may be provided in tube 22, in addition to proximal and distal holes 24 and 26, through which urokinase or TPA may as just described. FIG. 26 also depicts introducer sheath or catheter 99, which may be utilized in conjunction with the present delivery system to facilitate the insertion of the delivery system, including tubes 22 and 40, into the patient. (Note that push button lock/release mechanism 200 shown in FIG. 25 as connecting tube 40 and 22 is not depicted in FIG. 26.) Introducer catheter 99 may be attached to end fitting 204, as shown in FIG. 26, with a Luer connection. FIG. 26 also illustrates that multiple securing wires 46 may be utilized for securing the proximal end of the filter to tube 40. In this regard, although not shown, it will be understood to those of skill in the art, with the benefit of this disclosure, that securing wires 46 may be controlled by creating openings in tube 40 near the proximal end of tube 40 and threading the proximal ends of securing wires 46 through those holes. In this way, the proximal end of the filter or other device may be released by pulling the proximal ends of securing wires 46. Tightening screw 205 may be provided on the end of the side arm of end fitting 204, as shown in FIG. 26, for fixing the relative positions of securing wires 30 (not shown). Additionally, although not shown, it will be understood to those of skill in the art, with the benefit of this disclosure, that a tightening screw may be provided on the end of end fitting 204 for fixing or securing the relative position of any guidewires that are utilized as well.

In this embodiment of the invention, there may be no need to apply barbs/tabs at the distal end of the temporary filter. For example, the barbless stent filter, by nature, will not be equipped with barbs. However, such barbs or tabs may be supplied as shown in FIG. 27A to the other filters. The proximal end of the outer tube may be secured to the skin using surgical sutures. When the filter is to be removed, the temporary filter may be withdrawn into a catheter/sheath (such as tube 71) and the device may be withdrawn from the body.

An additional manner in utilizing the barbless stent filter as a temporary filter exists that does not involve leaving an outer tube in the body. In one embodiment, hook 410 may be used as a tool for removing a temporary filter. At the appropriate time, a foreign body snare, such as the Amplatz Goose Neck snare (Microvena Corp., White Bear Lake, Minn.) may be used to grasp hook 410 and retract the filter into an appropriately sized thin-walled sheath for removal from the body. The snared end of the filter may be held stationary and an appropriately-sized sheath (approximately 2-French sizes larger than the delivery system) may be advanced over the shaft of the foreign body snare to capture the filter.

For the retrievable filter, the distal end may be equipped with barbs/tabs. At the proximal end of the retrievable filter, a monofilament loop is threaded through the small closed loops (or bends) created from the bent wires such that the small closed loops become interconnected by the monofilament loop (see, e.g., FIG. 12); thus, pulling on the monofilament loop will result in drawing the small closed loops together thus reducing the diameter of the stent at the proximal end. The retrievable filter may be secured to the same delivery system used for delivery of the temporary filter in the same way.

Delivery may also be carried out in the same way. In an exemplary embodiment, the filter may be delivered from a right jugular approach. It is to be understood that if the delivery system is small enough, an antecubital approach may be acceptable, especially for a short time filtration. It is to be understood that delivery from a femoral approach may require the filter to be positioned inversely. After delivery of the retrievable filter from a jugular approach, for example, the delivery system may be removed and only the monofilament loop may be left within the vasculature. The very proximal end of the loop may be attached to the skin as above described. In this form, the retrievable filter may be used as a temporary filter. Both the flared base with the tighter mesh and the barbs/tabs may serve to anchor the retrievable filter within the cava. In the case of the barbless stent filter, base 402 may serve the function of the flared base of the other filters, which may or may not be provided with barbs or tabs. If it is necessary to convert the temporary filter into a permanent one, the monofilament loop may be severed and removed from the small closed loops of the filter as well as from the body.

If a decision is made to remove a retrievable filter, a short metal straightener may be advanced over the proximal end of the monofilament loop. A short introducer sheath may then be inserted in the access vein over the straightener. Through the introducer, an adequate size sheath may be advanced to the distal end of the filter. Stretching the monofilament loop, the sheath may be advanced over the filter. As a result, the barbs/tabs, if utilized, will be retracted from the caval wall, and the filter's removal can be achieved without causing injury to the vessel wall.

The time period for leaving a temporary filter in a patient will vary from case to case, but, generally, temporary filters may be left in place for no more than about two to three weeks. Leaving them in place for a longer period of time may result in the formation of a neointimal layer on the temporary filter, which would impede its removal. To increase the period of time during which these filters may be left in the body without being embedded into the neointimal layer, the filters may be coated with some biologically active materials (e.g., cytostatics, fibroblast growth factor [FGF-1] with heparin, Taxol, etc.) or the metal of the filter may be rendered β-particle-emitting producing a low-rate radiation at the site of the filter placement (Fischell, 1996).

The main advantage of the retrievable filter is that if the conversion from temporary to permanent filtration is necessary, there is no need to remove the temporary filter and deploy a permanent one. Both versions are suitable for intraluminal thrombolysis both from a jugular or a femoral approach or possibly an antecubital approach.

The retrievable filter provides additional advantages in that they are easily retrievable, they possess equal filtering capacity in the center and at the periphery of the cava, they provide safe thrombolysis, they are self-centering and self-anchoring, and unless hook 410 is utilized in conjunction with the barbless stent filter, it is unnecessary to use a foreign-body retrieval device which might involve lengthy manipulations. However, it is to be understood that, in some embodiments, small tabs may be coupled to the ends of the filters of the present invention for facilitating the removal of the filter with a foreign body retrieval device.

The cava filters of the present invention provide the advantage of improved filtration. The extended coverage of the filtering level comes with an improved thrombus capturing capacity of the cava filters. The presence of a thrombus in a traditional conical filter decreases the capture rate for a second embolus (Jaeger, 1998). The succeeding thrombus will not be able to get into the apex of the cone and has a higher chance of passing through the filter (Kraimps, 1992). The flow velocity, and therefore, the hydrodynamic force are increased at the stenotic site of the filter. Because conical filters predominantly capture thrombi in the apex of the cone, the site of increased velocity is located at the periphery of the filter. As long as the diameter of the thrombi is smaller than or equal to that of the stenotic opening, the locally increased velocity and hydrodynamic force will push the thrombi through the filter periphery.

Using the cava filters of the present invention, the thrombi will be primarily captured by the distal end of the conical and dome filters and by the dome of the barbless stent filter; in the case of the hourglass filter, the first filtration level is the narrow portion of the proximal end of the filter. Any subsequent emboli will be diverted to the periphery of the cava where the filter has approximately the same filtration capacity as in the center of the filter.

Figure 29:
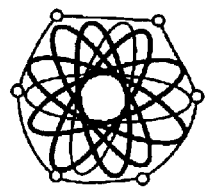
FIG. 29 is a projected cross section of an hourglass filters taken across the middle portion of the filter according to one embodiment of the present invention.

The filtration capacity of a filter can be estimated by looking at it from the top or below. The wires/mesh arrangement in the projected cross-section of the filtered segment of the IVC gives a good estimate about the "coverage" of the IVC by the filter. For example, FIG. 29 depicts a projected cross section of one of the present hourglass filters taken across the middle portion of the filter. In the case of the hourglass filter, the blood is primarily filtered by the proximal half of the filter, similar to the case using the dome or conical filter. The blood which is going proximally alongside the caval wall will be filtered the peripheral mesh of both the proximal and the distal "dome". As a result, as in the case of the barbless stent filter, there is virtually no difference in filtration capacity of the filter in the center and at the periphery of the vessel. Additionally, with respect to each of the filters, the immediate opening and symmetric arrangement of the bases of the filters serves to self-center them and prevent them from being tilted. Some filter designs (especially the Greenfield-filter) are sensitive to intraluminal tilting, which negatively affects their filtration capability.

The flexibility of the mesh of the cava filters, as is the case with all the woven intravascular devices of the present invention, makes it possible to advance the delivery system through tortuous vessels. This feature together with the small size of the delivery system enables one to deliver these filters via every possible access site of the body. Further, as with all the intravascular devices of the present invention, the plain weave of the cava filters allows for the production of one coherent element, which does not possess any kind of joints.

The cava filters according to the present invention may possess (depending on the material used to form the wires thereof) a non-ferromagnetic character making them, as well as stents formed therefrom, MRI compatible.

The cava filters of the present invention are also suitable for intravascular thrombolysis. After placement of any kind of filtering device, the development of caval thrombosis/occlusion frequently occurs (Crochet, 1993). In acute cases, a possible therapeutic option is to recanalize the IVC by pharmaco-mechanical thrombolysis. Doing so in the presence of the currently available filters poses a high risk of developing pulmonary emboli, because large fragments of the IVC thrombus can break off and be carried away in an uncontrolled way after urokinase/TPA treatment. One of the acceptable options in that situation is to place another filter above the thrombosed filter to avoid pulmonary embolism due to thrombolysis. Unlike other designs, the cava filters according to the present invention may offer the possibility of a safe and successful thrombolysis without the need for the placement of two filters.

Bi-Iliac Tube Filter

The wires of the BI filter according to the present invention may be made of the same materials as the wires of the stents. The same number of wires may be used in forming the BI filter as are used to form the stents. However, in an exemplary embodiment, less wires are preferably used for the BI filter than for the stents. It is to be understood that although only 4 wires appear in FIGS. 11–13, 2 more wires are not shown. The BI filter may be created with a relatively loose mesh allowing the blood to flow freely. The size of the wires that may be used for forming the BI filter ranges from between about 0.008 inches and about 0.011 inches, but is most typically about 0.009 inches.

Figure 11:
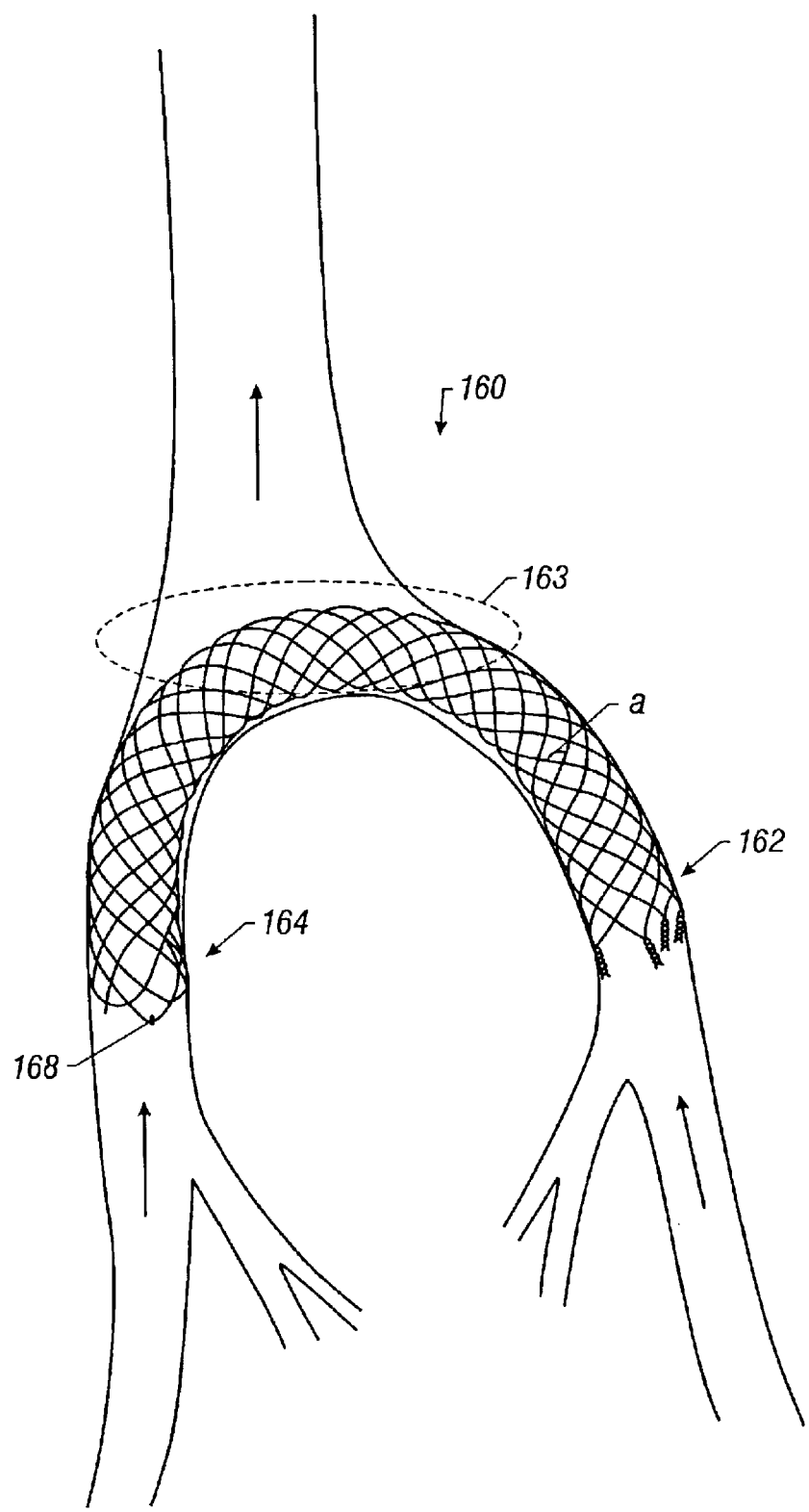
FIG. 11 is a front view of a bi-iliac filter according to one embodiment of the present invention placed in the iliac veins.
Figure 12:
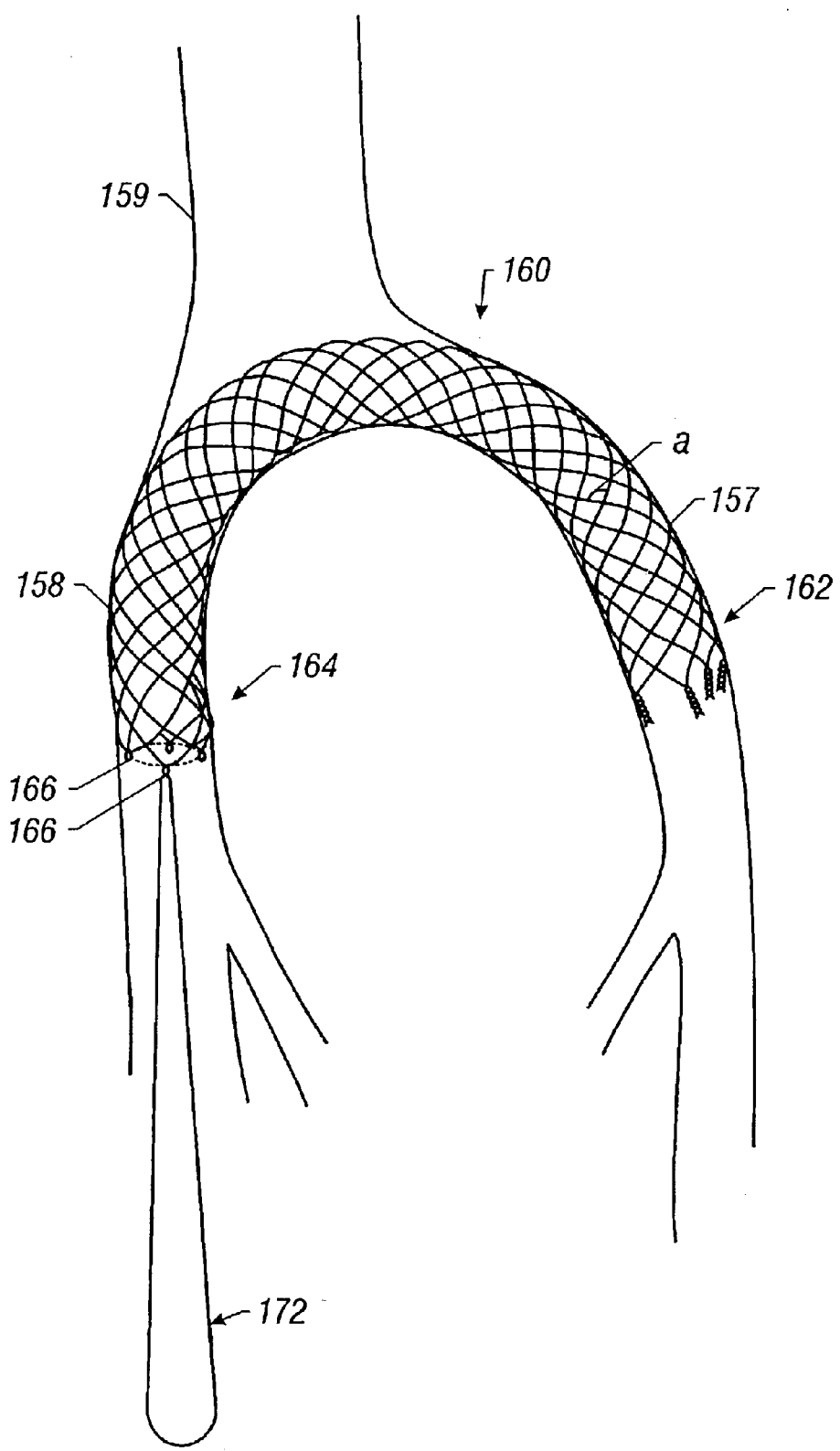
FIG. 12 is a front view of a bi-iliac filter having a retrieval loop according to one embodiment of the present invention placed in the iliac veins.
Figure 13:
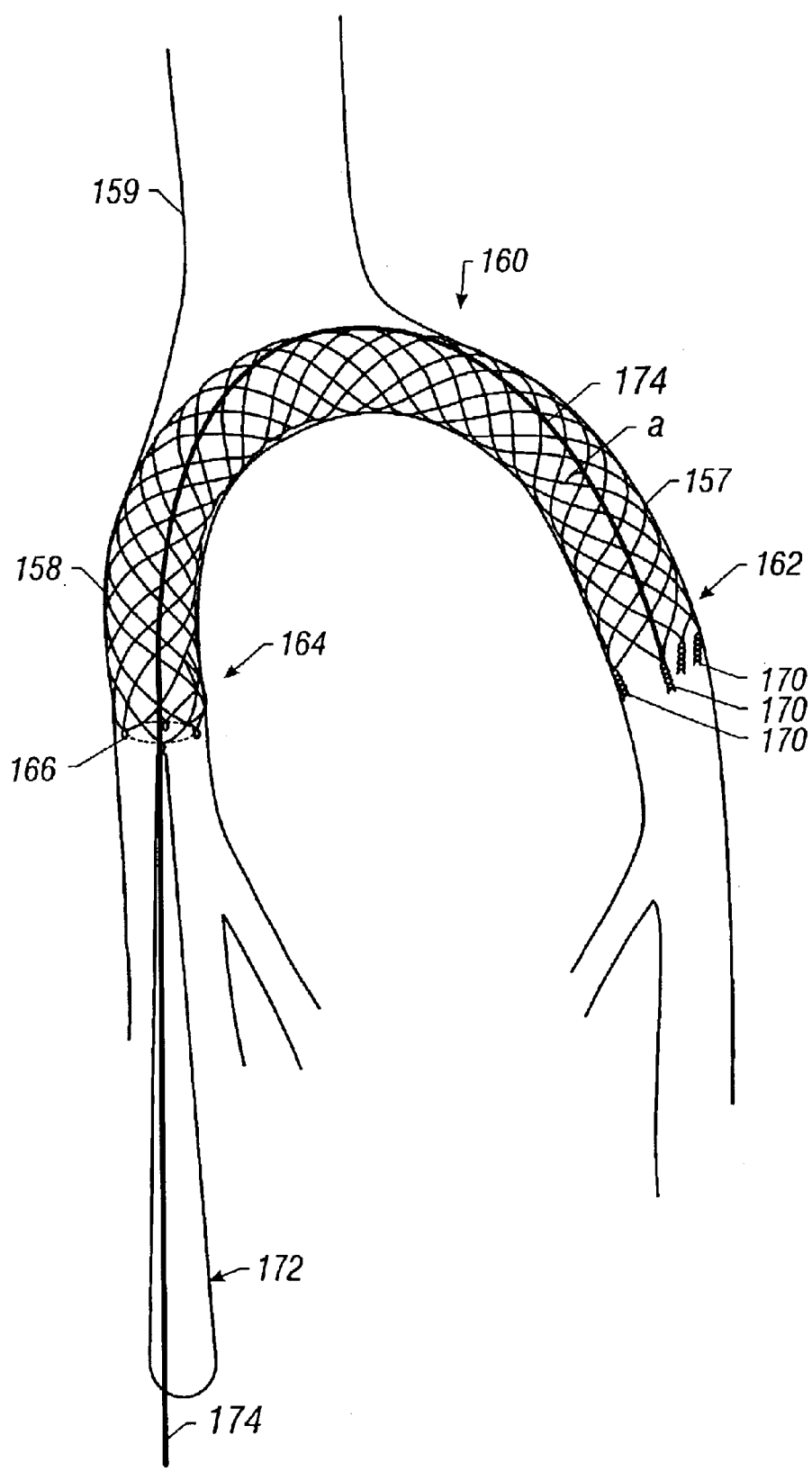
FIG. 13 is a front view of a bi-iliac filter having a retrieval loop and a stabilizing wire according to one embodiment of the present invention placed in the iliac veins.

The BI filter according to the present invention may be formed using the above described methods for forming the stents. Of course, an appropriately shaped template may be chosen. In weaving body 160 of the BI filter, as shown in FIGS. 11–13, the angle a between the crossing wires is preferably obtuse. It is to be understood that angle a may also be less than or equal to 90°. End 164 may have a plurality of closed structures which may be small closed loops 166 (FIGS. 12 and 13) or bends 168 (FIG. 11), like the above stents and filters. The angles of those closed structures may be similar to the angles for the closed structures of the stents as above described. The wire ends at 162 of body 160 may be coupled together in the manner above described.

Body 160 of the BI filter may also be heated as the stents are, and may be allowed to cool as the stents are.

In one embodiment, the mid-portion of the BI filter may be constructed with a larger diameter than that of the ends which are used for fixation. This may be achieved in a variety of ways using the remodeling methods above described. For example, one may weave a straight stent with a caliber useful for filtration (larger lumen). Then, smaller caliber ends may be formed by remodeling the filter on a smaller caliber template. In such a case, the weave of the filtering level will be looser than those of the legs. In another embodiment, the weave of the filtering level may be tighter than those of the legs by weaving the BI filter is on a template sized for the legs, and then remodeling the filter by ballooning the mid-portion of the filter outward. Many variations in shape are thus possible.

The BI filter of the present invention may be stretched completely on the delivery system, reducing its diameter as much as possible. It may be delivered in that stretched state into the inferior vena cava ("IVC"). It is to be understood that it may also be delivered into the IVC in a state that is not completely stretched. The filter may be inserted from either femoral vein and placed into both iliac veins forming an inverse U-shape bridging over the confluence of these veins. Unlike traditional IVC filters, the filtration according to the present invention will substantially take place through the cephalad surface 163 of the weave at about the mid-portion of body 160 located at the junction of the iliac veins, as shown in FIG. 11.

The BI filter is suitable for temporary filtration. In this embodiment of the present invention shown in FIG. 12, the coupled wire ends form the distal end of the filter, while the multiple small closed loops 166 located proximally are connected by a monofilament loop 172 as described above and shown in FIGS. 12 and 13. FIGS. 12 and 13 illustrate Bi-filter 160 delivered within left iliac vein 157 and right iliac vein 158, beneath the inferior vena cava 159. Using a contralateral approach, the filter may be inserted from either femoral vein and its front end may be positioned into the contralateral iliac vein. After delivery of the filter, the monofilament loop may be led outside the body and secured to the skin. When there is no further need for the filter, it may be withdrawn by pulling it back by the monofilament loop through an advanced sheath.

In another possible embodiment of this invention shown in FIG. 13, a flexible, superelastic wire or microtubing 174 made from nitinol (or similar superelastic/shape memory material described above) is led through the lumen of the BI filter. The distal end of the nitinol wire/microtubing is attached or coupled to one twisted wire-end 170 of the filter by any suitable means, including soldering, point welding, wrapping of fibers, and the like. The proximal end of the wire/microtubing may be attached to the skin (along with the monofilament loop). When the BI filter is being withdrawn, the wire/microtubing may be held steadily, while the monofilament loop is pulled. As a result, the BI filter will be partially stretched facilitating the filter's removal. The BI filter may also be removed in the fashion described above for removing the temporary filter.

As discussed above, given the design of the BI-filter, one may catheterize the lumen of the filter and, using an adequate size catheter, thrombus-suction may be easily performed before filter removal.

Delivery System of the BI Filter

Version 1 shown in FIG. 3 may be used as the delivery system for the BI filter (including a biodegradable version) according to the present invention.

Delivery of the BI Filter

A preferably preformed guiding catheter or a guiding sheath (Balkin sheath-type) (FIG. 3) may be used for insertion of the delivery system for the embodiments discussed above. The BI filter may be secured to and stretched out on the surface of the delivery system in a manner described above, and may be delivered from the ipsilateral femoral/iliac vein through the caval junction into the contralateral iliac vein. As discussed above with regard to the delivery of the stents, the construction of the delivery system enables one to use a guidewire in the lumen of tube 22 for delivery of the filter, which is preferable in an exemplary embodiment of the present invention. It is to be understood however, that a guidewire may not be utilized if a preformed sheath is in place.

The BI filter may be delivered into place in the manner described above with regard to the delivery of the stents using version 1. All the advantages described above with regard to repositionability, etc., apply equally to the delivery of the BI filter. In an exemplary embodiment of the delivery method for the BI filter, the distal end of the BI filter may be released first.

Advantageously, the BI filter according to the present invention may offer the possibility of a safe and successful thrombolysis, like the cava filters above discussed.

All of the methods and apparatus disclosed and claimed herein can be made and executed without undue experimentation in light of the present disclosure. While the methods and apparatus of the present invention have been described in terms of illustrative embodiments, it will be apparent to those of skill in the art that variations may be applied to apparatus and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ben-Menachem, Coldwell, Young, Burgess, "Hemorrhage associated with pelvic fractures: causes, diagnosis, and emergent management," AJR, 157:1005–1014, 1991.

Bing, Hicks, Figenshau, Wick M, Picus D. Darcy M D, Clayman R V. "Percutaneous ureteral occlusion with use of Gianturco coils and gelatine sponge, Part I. Swine model" JVIR; 3:313–317, 1992 (a)

Bing, Hicks, Picus, Darcy. "Percutaneous ureteral occlusion with use of Gianturco coils and gelatine sponge, Part II. Clinical Experience," JVIR; 3:319–321, 1992 (b)

Cambier, Kirby, Wortham, Moore, "Percutaneous closure of the small (<2.5 mm) patent ductus arteriosus using coil embolization," Am. J. Cardiol., 69:815–816, 1992.

Crochet, Stora, Ferry et al., "Vena Tech-LGM filter: long-term results of a prospective study," Radiology, 188:857–860, 1993.

Dorfman, "Percutaneous inferior vena cava filters," Radiology, 174:987–992, 1990.

Dutton, Jackson, Hughes et al., "Pulmonary arteriovenous malformations: results of treatment with coil embolization in 53 patients," AJR, 165:1119–1125, 1995.

Fischell, Carter, Laird, "The β-particle-emitting radiosotope stent (Isostent): animal studies and planned clinical trials," Am. J. Cardiol., 78(Suppl 3A):45–50, 1996.

Furuse, Iwasaki, Yoshino, Konishi, Kawano, Kinoshita, Ryu, Satake, Moriyama, "Hepatocellular carcinoma with portal vein tumor thrombus: embolization of arterioportal shunts," Radiology, 204:787–790, 1997.

Gianturco, Anderson, Wallace, "Mechanical device for arterial occlusion," AJR, 124:428–435, 1975.

Grassi, "Inferior vena caval filters: Analysis of five currently available devices," AJR, 156:813–821, 1991.

Grifka, Vincent, Nihill, Ing, Mullins, "Transcatheter patent ductus arteriosus closure in an infant using the Gianturco Grifka vascular occlusion device," Am. J. Cardiol., 78:721–723, 1996.

Guglielmi, Vinuela, Duckwiler, Dion, Stocker, "Highflow, small-hole arteriovenous fistulas: treatment with electro-detachable coils," AJNR, 16:325–328, 1995.

Hammer, Rousseau, Joffre, Sentenac, Tran-van, Barthelemy, "In vitro evaluation of vena cava filters," JVIR, 5:869–876, 1994.

Hendrickx, Orth, Grunert, "Long-term survival after embolization of potentially lethal bleeding malignant pelvic turnouts," Br. J. Radial., 68:1336–1343, 1995.

Hijazi and Geggel, "Results of anterograde transcatheter closure of patent ductus arteriosus using single or multiple Gianturco coils," Am. J. Cardiol., 74:925–929, 1994.

Hijazi and Geggel, "Transcatheter closure of patent ductus arteriosus using coils," Am. J. Cardiol., 79:1279–1280, 1997.

Hosking, Benson, Musewe, Dyck, Freedom, "Transcatheter occlusion of the persistently patent ductus arteriosus," Circulation, 84:2313–2317, 1991.

Jaeger, Kolb, Mair, Geller, Christmann, Kinne, Mathias, "In vitro model for evaluation of inferior vena cava filters: effect of experimental parameters on thrombus-capturing efficacy of the Vena Tech-LGM filter," JVIR, 9:295–304, 1998.

Kato, Semba, Dake, "Use of a self-expanding vascular occluder for embolization during endovascular aortic aneurysm repair," JVIR, 8:27–33, 1997.

Katsamouris, Waltman, Delichatsios, Athanasoulis, "Inferior vena cava filters: In vitro comparison of clot trapping and flow dynamics," Radiology, 166:361–366, 1988.

Kónya, Wright, Wallace, "Anchoring coil embolization in a high-flow arterial model," JVIR, 9:249–254, 1998.

Kónya, Wright, "Preliminary results with a new vascular basket occluder in swine. JVIR, 10:1043–1049, 1999.

Koran, Reed, Taylor, Pantecost, Teitelbaum, "Comparison of filters in an oversized vena caval phantom: intracaval placement of a Bird's Nest filter versus biiliac placement of Greenfield, Vena-Tech-LGM, and Simon nitinol filters," JVIR, 3:559–564, 1992.

Krichenko, Benson, Burrows, Moes, McLaughlin, Freedom, "Angiographic classification of the isolated, persistently patent ductus arteriosus and implications for percutaneous catheter occlusion," Am. J. Cardiol., 63:877–880, 1989.

Latson, "Residual shunts after transcatheter closure of patent ductus arteriosus," Circulation, 84:2591 2593, 1991.

Levey, Teitelbaum, Finck, Pentecost, "Safety and efficacy of transcatheter embolization of auxiliary and shoulder arterial injuries," JVIR, 2:99–104, 1991.

Lipton et al., "Percutaneous Retrieval of two Wallstent endoprostheses from the heart through a single jugular sheath," JVIR, 6:469472, 1995.

Lloyd, Fedderly, Mendelsohn, Sandhu, Beekman, "Transcatheter occlusion of patent ductus arteriosus with Gianturco coils," Circulation, 88:1412–1420, 1993.

Magal, Wright, Duprat, Wallace, Gianturco, "A new device for transcatheter closure of patent ductus arteriosus: a feasibility study in dogs," Invest. Radiol., 24:272–276, 1989.

Marks, Chee, Liddel, Steinberg, Panahian, Lane, "A mechanically detachable coil for the treatment of aneurysms and occlusion of blood vessels," AJNR, 15:821–827, 1994.

Masura, Walsh, Thanopoulous, Chan, Bass, Gousous, Gavora, Hijazi, "Catheter closure of moderate to large sized patent ductus arteriosus using the new Amplatz duct occluder: immediate and short term results," J. Am. Coll. Cardiol., 31:878–882, 1998.

Milward, "Temporary and Retrievable inferior vena cava filters: Current status," JVIR, 9:381–387, 1998.

Murayama, Vinuela, Ulhoa, Akiba, Duckwiler, Gobin, Vinters, Greff, "Nonadhesive liquid embolic agent for cerebral arteriovenous malformations: Preliminary histopathological studies in swine rete mirabile," *Neurosurgery,* 43:1164–1175, 1998.

Nancarrow, Fellows, Lock, "Stability of coil emboli: an in vitro study," *Cardiovasc. Intervent. Radiol.,* 10:226–229, 1987.

O'Halpin, Legge, MacErlean, "Therapeutic arterial embolization: report of five years' experience," *Clin. Radiol.,* 354:85–93, 1984.

Pozza, Gomes, Qian, Ambrozaitis, Kim, Amplatz, "Transcatheter occlusion of patent ductus arteriosus using a newly developed self-expanding device: evaluation in a canine model," *Invest. Radiol.,* 30:104–109, 1995.

Prahlow et al., "Cardiac perforation due to Wallstent embolization: a fatal complication of the transjugular intrahepatic portosystemic shunt procedure," *Radiology,* 205:170–172, 1997.

Prince, Salzman, Schoen, Palestrant, Simon, "Local; intravascular effects of the nitinol wire blood clot filter," *Invest. Radiol.,* 23:294–300, 1988.

Punekar, Prem, Ridhorkar, Deshmukh, Kelkar, "Postsurgical recurrent varicocele: efficacy of internal spermatic venography and steel-coil embolization," *Br. J. Urol.,* 77:12–128, 1996.

Rashkind, Mullins, Hellenbrand, Tait, "Nonsurgical closure of patent ductus arteriosus: clinical application of the Rushkind PDA occluder system," *Circulation,* 75:583–592, 1987.

Reidy and Qureshi, "Interlocking detachable platinum coils, a controlled embolization device: early clinical experience," *Cardiovasc. Intervent. Radiol.,* 19:85–90, 1996.

Sagara, Miyazono, Inoue, Ueno, Nishida, Nakajo, "Recanalization after coil embolotherapy of pulmonary arteriovenous malformations: study of long term outcome and mechanism for recanalization," *AJR,* 170:727–730, 1998.

Schmitz Rode, Timmermans, Uchida, Kichikawa, Hishida, Gunther, Rosch, "Self-expandable spindle for transcatheter vascular occlusion: in vivo experiments," *Radiology,* 188:95–100, 1993.

Schurmann et al., "Neointimal hyperplasia in low-profile nitinol stents, Palmaz stents, and Wallstents: a comparative experimental study," *Cardiovasc. Intervent. Radiol.* 19:248–254, 1996.

Schild, Mildenberger, Kerjes, "Effectiveness of platinum wire microcoils for venous occlusion: a study on patients treated for venogenic impotence," *Cardiovasc. Intervent. Radiol.,* 17:170–172, 1994.

Schwartz, Teitelbaum, Kantz, Pentecost, "Effectiveness of transcatheter embolization in the control of hepatic vascular injuries," *JVIR,* 4:359–365, 1993.

Selby Jr., "Interventional radiology of trauma," *Radiol. Clin. N. Am.,* 30:427–439, 1992.

Sharaffuddin, Gu, Cervera Ceballos, Urness, Amplatz, "Repositionable vascular occluder: experimental comparison with standard Gianturco coils," *JVIR,* 7:695 703, 1996.

Sharafuddin, Gu, Titus, Sakinis, Pozza, Coleman, Cervera-Ceballos, Aideyan, Amplatz, "Experimental evaluation of a new self expanding patent ductus arteriosus occluder in a canine model," *JVIR,* 7:877 887, 1996.

Simon, Rabkin, Kleshinski, Kim, Ransil, "Comparative evaluation of clinically available inferior vena cava filters with an in vitro physiologic simulation of the vena cava," *Radiology,* 189:769–774, 1993.

Sommer, Gutierrez, Lai, Parness, "Use of preformed nitinol snare to improve transcatheter coil delivery in occlusion of patent ductus arteriosus," *Am. J. Cardiol.,* 74:836–839, 1994.

Taki, Yonekawa, Iwata, Uno, Yamashita, Amemiya, "A new liquid material for embolization of arteriovenous malformations,' *AJNR,* 11:163–168, 1990.

Teitelbaum, Reed, Larsen, Lee, Pentecost, Finck, Katz, "Microcatheter embolization of non-neurologic traumatic vascular lesions," *JVIR,* 4:149–154, 1993.

Terada, Nakamura, Nakai et al., "Embolization of arteriovenous malformations with peripheral aneurysms using ethylene vinyl alcohol copolymer," *J. Neurosurg.,* 75:655–660, 1991.

Tometzki, Arnold, Peart et al., "Transcatheter occlusion of the patent ductus arteriosus with Cook detachable coils," *Heart,* 76:531–535, 1996.

Uzun, Hancock, Parsons, Dickinson, Gibbs, "Transcatheter occlusion of the arterial duct with Cook detachable coils: early experience," *Heart,* 76:269–273, 1996.

Vedantham, Goodwin, McLucas, Mohr, "Uterine artery embolization: an underused method of controlling pelvic hemorrhage," *Am. J. Obstet. Gynecol.,* 176:938–948, 1997.

Vesely et al., "Upper extremity central venous obstruction in hemodialysis patients: treatment with Wallstents," *Radiology,* 204:343–348, 1997.

Wallace, Granmayeh, deSantos, Murray, Romsdahl, Bracken, Jonsson, "Arterial occlusion of pelvic bone tumors," *Cancer,* 43: 322–328, 1979.

Wallsten, U.S. Pat. No. 4,655,771, 1987.

Wessel, Keane, Parness, Lock, "Outpatient closure of the patent ductus arteriosus," *Circulation,* 77:1068 1071, 1988.

White, Pollak, Wirth, "Pulmonary arteriovenous malformations: diagnosis and transcatheter embolotherapy," *JVIR,* 7:787–804, 1996.

Xian, Roy, Hosaka, Kvemebo, Laerum, "Multiple emboli and filter function: An in vitro comparison of three vena cava filters," *JVIR,* 6:887–893, 1995.

Yune, "Inferior vena cava filter: Search for an ideal device," *Radiology,* 172:15–16, 1989.

Zubillaga, Guglielmi, Vinuela, Duckwiler, "Endovascular occlusion of intracranial aneurysms with electrically detachable coils: correlation of aneurysm neck size and treatment results," *AJNR,* 15:815–820, 1994.

What is claimed is:

1. A method of creating a body suitable for implantation into an anatomical structure, the body having two ends, the method comprising:
   providing a weaving system comprising:
      a template having first template projections;
      bending shape memory wires around the first template projections to create bent portions in the shape memory wires, the bent portions being arranged to define one end of the body, each shape memory wire having two ends; and
      weaving the ends of the shape memory wires around the template to create the body such that the shape memory wires cross each other to form a plurality of angles, at least one of the angles being obtuse;
   wherein the value of the at least one obtuse angle may be increased by axially compressing the body.

2. The method of claim 1, wherein the first template projections comprise tabs.

3. The method of claim 1, wherein the first template projections comprise pins.

4. The method of claim 3, wherein the pins are attached to a ring engaged with the template.

5. The method of claim 1, wherein the weaving system further comprises a first weaving plate configured to rotate in a first direction during the weaving.

6. The method of claim 5, wherein the weaving system further comprises first bobbins arranged on the first weaving plate, one end of each shape memory wire being attached to each first bobbin prior to the weaving.

7. The method of claim 5, wherein the weaving system further comprises a second weaving plate configured to rotate in a second direction during the weaving, the second weaving plate being spaced apart from the first weaving plate.

8. The method of claim 7, wherein the weaving system further comprises second bobbins arranged on the second weaving plate, one end of each shape memory wire being attached to each second bobbin prior to the weaving.

9. The method of claim 1, further comprising securing the shape memory wires to the template.

10. The method of claim 1, further comprising forming closed structures with the ends of the shape memory wires, the closed structures being arranged to define the other end of the body.

11. The method of claim 1, further comprising heating the body and the template.

12. A method of creating a body suitable for implantation into an anatomical structure, the body having two ends, the method comprising:
   providing a weaving system comprising:
      a template having first template projections;
   bending shape memory wires around the first template projections to create bent portions in the shape memory wires, the bent portions being arranged to define one end of the body, each shape memory wire having two ends; and
   weaving the ends of the shape memory wires around the template to create the body such that the shape memory wires cross each other in non-interlocking fashion to form a plurality of angles, at least one of the angles being obtuse;
   where the value of the at least one obtuse angle may be increased by axially compressing the body.

13. The method of claim 12, where the first template projections comprise tabs.

14. The method of claim 12, where the first template projections comprise pins.

15. The method of claim 14, where the pins are attached to a ring engaged with the template.

16. The method of claim 12, where the weaving system further comprises a first weaving plate configured to rotate in a first direction during the weaving.

17. The method of claim 16, weaving system further comprises first bobbins arranged on the first weaving plate, one end of each shape memory wire being attached to each first bobbin prior to the weaving.

18. The method of claim 16, where the weaving system further comprises a second weaving plate configured to rotate in a second direction during the weaving, the second weaving plate being spaced apart from the first weaving plate.

19. The method of claim 18, where the weaving system further comprises second bobbins arranged on the second weaving plate, one end of each shape memory wire being attached to each second bobbin prior to the weaving.

20. The method of claim 12, further comprising securing the shape memory wires to the template.

21. The method of claim 12, further comprising forming closed structures with the ends of the shape memory wires, the closed structures being arranged to define the other end of the body.

22. The method of claim 12, further comprising heating the body and the template.

* * * * *